United States Patent
Kim et al.

(10) Patent No.: US 9,714,897 B2
(45) Date of Patent: Jul. 25, 2017

(54) HYDROGEL PARTICLES WITH TUNABLE OPTICAL PROPERTIES AND METHODS FOR USING THE SAME

(71) Applicant: SLINGSHOT BIOSCIENCES, INC., Emeryville, CA (US)

(72) Inventors: Jeffrey Kim, Berkeley, CA (US); Oliver Liu, San Francisco, CA (US); Jeremy Agresti, El Cerrito, CA (US); Anh Tuan Nguyen, San Jose, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

(21) Appl. No.: 15/018,769

(22) Filed: Feb. 8, 2016

(65) Prior Publication Data
US 2016/0258856 A1   Sep. 8, 2016

Related U.S. Application Data

(60) Provisional application No. 62/114,004, filed on Feb. 9, 2015, provisional application No. 62/184,192, filed on Jun. 24, 2015.

(51) Int. Cl.
*G01N 31/00* (2006.01)
*G01N 15/10* (2006.01)
(Continued)

(52) U.S. Cl.
CPC .......... *G01N 15/1012* (2013.01); *C12Q 1/04* (2013.01); *G01N 1/28* (2013.01); *G01N 15/1434* (2013.01);
(Continued)

(58) Field of Classification Search
None
See application file for complete search history.

(56) References Cited

U.S. PATENT DOCUMENTS 4,704,891 A   11/1987   Recktenwald et al.
4,774,189 A   9/1988   Schwartz
(Continued)

FOREIGN PATENT DOCUMENTS

WO   8910566   11/1989
WO   0008212   2/2000
(Continued)

OTHER PUBLICATIONS

Ugelstad, J. and Mork, P.C., "Swelling of Oligomer-Polymer Particles. New Methods of Preparation of Emulsions and Polymer Dispersions," Advances in Colloid and Interface Sciences, 13 (1980), pp. 101-140.
(Continued)

*Primary Examiner* — Robert Xu
(74) *Attorney, Agent, or Firm* — Cooley LLP; Nathan W. Poulsen

(57) ABSTRACT

Hydrogel particles and their use in cytometic applications are described. The hydrogel particles described herein are selectively tunable to have at least one optical property substantially similar to the at least one optical property of a target cell. In this regard, the hydrogel particles provided herein in one aspect, are used as a calibration reagent for the detection of a target cell in a sample.

26 Claims, 13 Drawing Sheets

(51) Int. Cl.
*C12Q 1/04* (2006.01)
*G01N 1/28* (2006.01)
*G01N 15/14* (2006.01)
*G01N 15/00* (2006.01)

(52) U.S. Cl.
CPC . *G01N 15/1459* (2013.01); *G01N 2001/2893* (2013.01); *G01N 2015/0065* (2013.01); *G01N 2015/1006* (2013.01); *G01N 2015/1018* (2013.01); *G01N 2015/149* (2013.01)

(56) References Cited

U.S. PATENT DOCUMENTS

| | | | |
|---|---|---|---|
| 5,093,234 A | 3/1992 | Schwartz | |
| 5,283,079 A | 2/1994 | Wang et al. | |
| 5,395,688 A | 3/1995 | Wang et al. | |
| 5,820,879 A | 10/1998 | Fernandez et al. | |
| 6,586,176 B1 | 7/2003 | Trnovsky et al. | |
| 6,806,058 B2 | 10/2004 | Jesperson et al. | |
| RE39,542 E | 4/2007 | Jain et al. | |
| 7,314,584 B2 | 1/2008 | Tsutsui et al. | |
| 8,030,095 B2 | 10/2011 | Harriman | |
| 8,187,885 B2 | 5/2012 | Purvis, Jr. | |
| 8,415,173 B2 | 4/2013 | Harriman | |
| 8,704,158 B2 | 4/2014 | Haberstroh et al. | |
| 2003/0132538 A1 | 7/2003 | Chandler | |
| 2005/0176056 A1 | 8/2005 | Sammak et al. | |
| 2006/0240560 A1 | 10/2006 | Bakker et al. | |
| 2007/0054119 A1 | 3/2007 | Garstecki et al. | |
| 2007/0259415 A1 | 11/2007 | Zigova et al. | |
| 2009/0148961 A1 | 6/2009 | Luchini et al. | |
| 2010/0234252 A1 | 9/2010 | Moradi-Araghi et al. | |
| 2010/0285594 A1* | 11/2010 | Purvis, Jr. .......... | G01N 15/1012 436/10 |
| 2011/0318820 A1 | 12/2011 | Hinz et al. | |
| 2012/0309651 A1* | 12/2012 | Pregibon ............. | C12Q 1/6816 506/16 |
| 2013/0177973 A1 | 7/2013 | Kondo | |
| 2015/0177115 A1 | 6/2015 | Kim et al. | |

FOREIGN PATENT DOCUMENTS

| | | |
|---|---|---|
| WO | 0132829 | 5/2001 |
| WO | 03000014 A2 | 1/2003 |
| WO | 2008115653 A2 | 9/2008 |
| WO | 2010025988 A1 | 3/2010 |
| WO | 2011098407 A1 | 8/2011 |
| WO | 2012033811 A1 | 3/2012 |

OTHER PUBLICATIONS

Lee, Ki-Chang and Lee, Sang-Yun, "Preparation of Highly Cross-Linked, Monodisperse Poly (methyl methacrylate) Microspheres by Dispersion Polymerization; Part II Semi-continuation Processes," Macromolecular Research, vol. 16, No. 4, (2008) pp. 293-302.

Jin-Woong Kim, Andrew S. Utada, Alberto Fernandez-Nieves, Zhibing Hu, and David A.Weitz, "Fabrication of Monodisperse Gel Shells and Functional Microgels in Microfluidic Devices," Angew. Chem. Int. Ed. (2007) 46, pp. 1819-1822.

International Search Report and Written Opinion for International Patent Application No. PCT/US2016/017029, mailed May 19, 2016.

Patanarut, Alexis, et al. "Synthesis and characterization of hydrogel particles containing Cibacron Blue F3G-A." Colloids and Surfaces A: Physicochemical and Engineering Aspects 362.1 (2010): 8-19.

Luchini, Alessandra, et al. "Smart hydrogel particles: biomarker harvesting: one-step affinity purification, size exclusion, and protection against degradation." Nano letters 8.1 (2008): 350-361.

Bele, Marjan, Olavi Siiman, and Egon Matijevic. "Preparation and flow cytometry of uniform silica-fluorescent dye microspheres." Journal of colloid and interface science 254.2 (2002): 274-282.

Proff, Guenther, et al. "Potential of label-free detection in high-content-screening applications." Journal of Chromatography A 1161.1 (2007): 2-8.

Hasegawa, Urara, et al. "Nanogel-quantum dot hybrid nanoparticles for live cell imaging." Biochemical and biophysical research communication 331.4 (2005): 917-921.

Tomczak, Nikodem, et al. "Designer polymer-quantum dot architectures."Progress in Polymer Science 34.5 (2009): 393-430.

* cited by examiner

A)

B)

A

B

C ing of side scattering independent of forward scattering.
HYDROGEL PARTICLES WITH TUNABLE OPTICAL PROPERTIES AND METHODS FOR USING THE SAME

CROSS REFERENCE TO RELATED APPLICATIONS

This application claims priority from U.S. Provisional Application No. 62/114,004, filed Feb. 9, 2015 and U.S. Provisional Application No. 62/184,192, filed Jun. 24, 2015, the disclosure of each of which is incorporated by reference herein in their entireties.

BACKGROUND OF THE INVENTION

Flow cytometry is a technique that allows for the rapid separation, counting, and characterization of individual cells and is routinely used in clinical and laboratory settings for a variety of applications. The technology relies on directing a beam of light onto a hydrodynamically-focused stream of liquid. A number of detectors are then aimed at the point where the stream passes through the light beam: one in line with the light beam (Forward Scatter or FSC) and several perpendicular to it (Side Scatter or SSC). FSC correlates with the cell volume and SSC depends on the inner complexity of the particle (e.g., shape of the nucleus, the amount and type of cytoplasmic granules or the membrane roughness). As a result of these correlations, different specific cell types exhibit different FSC and SSC, allowing cell types to be distinguished in flow cytometry.

The ability to identify specific cell types, however, relies on proper calibration of the instrument, a process that has relied on the use of purified cells of the cell type of interest. Obtaining these purified cells can require costly, laborious procedures that are prone to batch-to-batch variation. Therefore, there is a need in the art for synthetic compositions with tunable optical properties that can mimic specific cell types in devices such as flow cytometers.

SUMMARY OF THE INVENTION

In one aspect of the invention, a hydrogel particle comprising a polymerized monomer and having at least one surface is provided. The hydrogel particle has at least one optical property that is substantially similar to the at least one optical property of a target cell. The optical property in one embodiment, is a side scatter profile (SSC), forward scatter profile (FSC), a fluorescence emission profile, or a combination thereof. The target cell can be any target cell that the user specifies. For example, in one embodiment, the target cell is an immune cell, stem cell or cancer cell.

In another aspect, a method for calibrating a cytometric device for analysis of a target cell, is provided. In one embodiment, the method comprises inserting into the device a hydrogel particle having at least one optical property substantially similar to a target cell, wherein the hydrogel particle comprises a polymerized monomer and has at least one surface. The method further comprises measuring the at least one optical property of the hydrogel particle using the cytometric device. The at least one optical property in one embodiment, is used as a reference to detect a target cell in a sample.

In yet another aspect, a method for detecting a target cell in a sample is provided. The method comprises inserting into in the device a hydrogel particle having at least one optical property substantially similar to a target cell, wherein the hydrogel particle comprises a polymerized monomer. The method further comprises measuring the at least one optical property of the hydrogel particle using the cytometric device. A sample comprising a plurality of cells is inserted into the cytometric device, and the at least one optical property of individual cells of the plurality are measured. Finally, a determination is made, based on the optical property measurement, whether the target cell or plurality thereof is present in the sample.

In one embodiment of the methods provided herein, the hydrogel particle comprises a biodegradable monomer. In a further embodiment, the biodegradable monomer is a monosaccharide, disaccharide, polysaccharide, peptide, protein, or protein domain. In even a further embodiment, the biodegradable monomer is functionalized with acrylamide or acrylate.

DETAILED DESCRIPTION OF THE INVENTION

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

Several critical calibration measurements for flow cytometers require precise time resolution, such as setting the offset time between lasers, and calculating the delay time between detection and sorting of an object. Due to the fluidic conditions within the instrument, precise setting of these timing parameters requires the use of calibration particles that are the same size as the cells to be analyzed. Timing calibrations are typically performed using polystyrene beads with variable fluorescent intensities to calibrate the response of an excitation source and to set the inter-laser timing delay and sorting delay. Flow cytometers can also be calibrated using forward and side scatter signals which are general measures of size and granularity or complexity of the target sample. These calibrations are crucial for the accurate performance of the cytometer and for any downstream analysis or sorting of cell populations. The disclosed hydrogel particles exhibit tuned scatter properties and are suitable for use as calibration reagents for a range of mammalian or bacterial cell types. Scattering is a standard metric for distinguishing cell types in heterogeneous mixtures for clinical, food safety, and research purposes.

Figure 1:
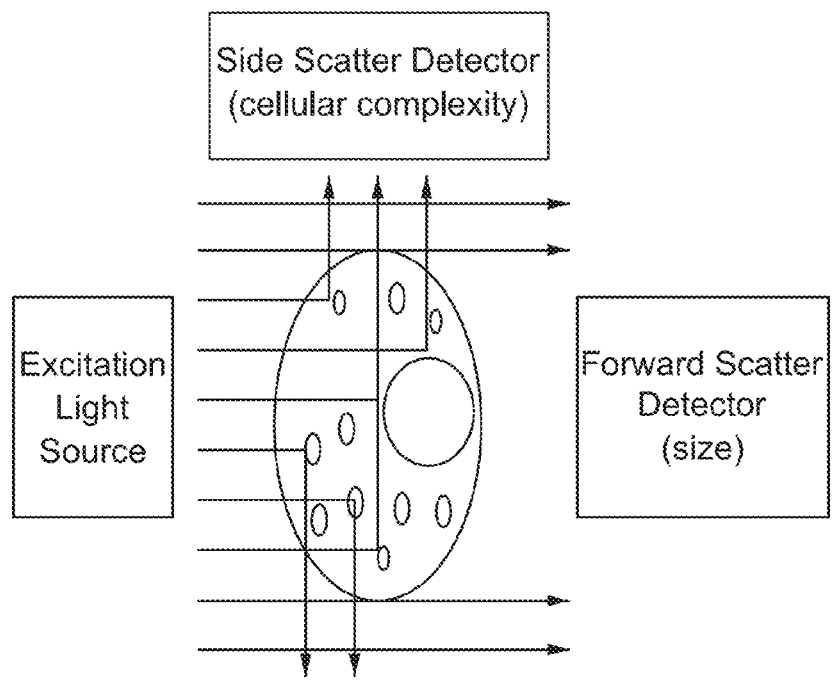
FIG. 1 illustrates the optical properties of disclosed hydrogel particles compared to polystyrene beads.
Figure 1:
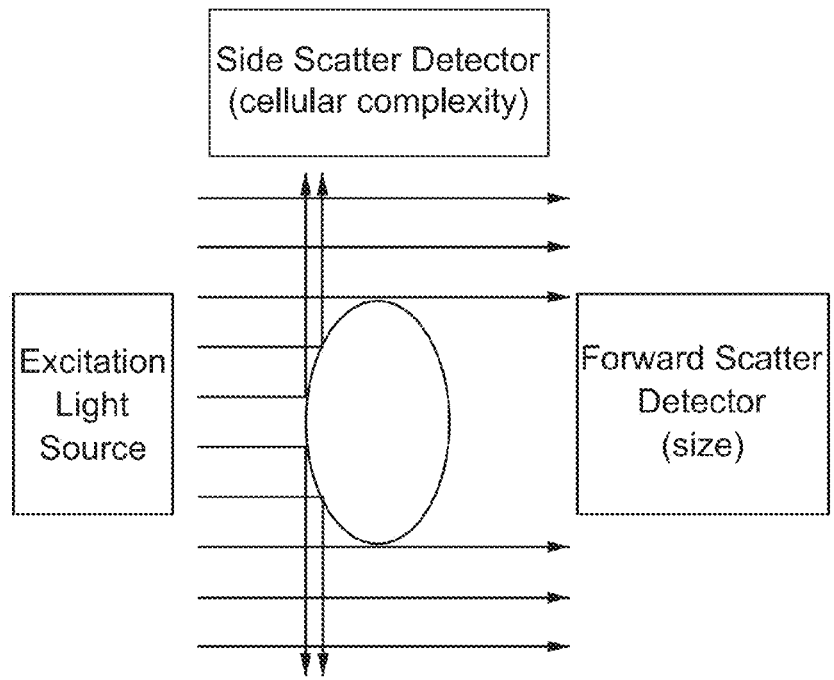

Although polystyrene particles can be used to set inter-laser and sorting delays for some applications, many eukaryotic cell types fall outside of the size range of commercially available polystyrene particles (1-20 µm) making it nearly impossible to accurately calibrate a flow cytometer for these targets. Also, as shown in FIG. 1, polystyrene particles are fundamentally limited in the optical properties that can possess such as side scattering, which is a general measure of cellular complexity. Polystyrene particles are therefore limited in the two most important passive optical measurements used in flow cytometry: FSC (forward scattering), and SSC (side scattering) which measure the size and complexity of the target respectively. Due to these limitations of polystyrene, users must rely on purified cell lines to calibrate fluorescent intensity, inter-laser delay, sort delays, size and cellular complexity for experiments. This is a lengthy and labor-intensive process that increases the cost of flow cytometry validation and research pipelines significantly. More importantly, these calibration cell lines introduce biological variation, causing disparities in the interpretation of data.

Moreover, quality control (QC) for calibration of flow cytometers is also a crucial consideration when these instruments are used for clinical applications, for example, to isolate human T-regulatory cells or stem cells for downstream cellular therapies. The FDA mandates that the sterility, identity, purity, and potency of a cell therapy product be demonstrated before administration to patients (Riley et al. (2009). Immunity 30, pp. 656-665). Contamination of a cellular population with polystyrene QC particles could therefore be problematic, as polystyrene has been implicated in certain cancers. Additionally, a cellular population that is contaminated with a QC standard that is enzymatically degraded or digested internally after administration to a patient potentially overcomes contamination issues, should they arise.

The present invention addresses these and other needs, as discussed below.

Figure 10:
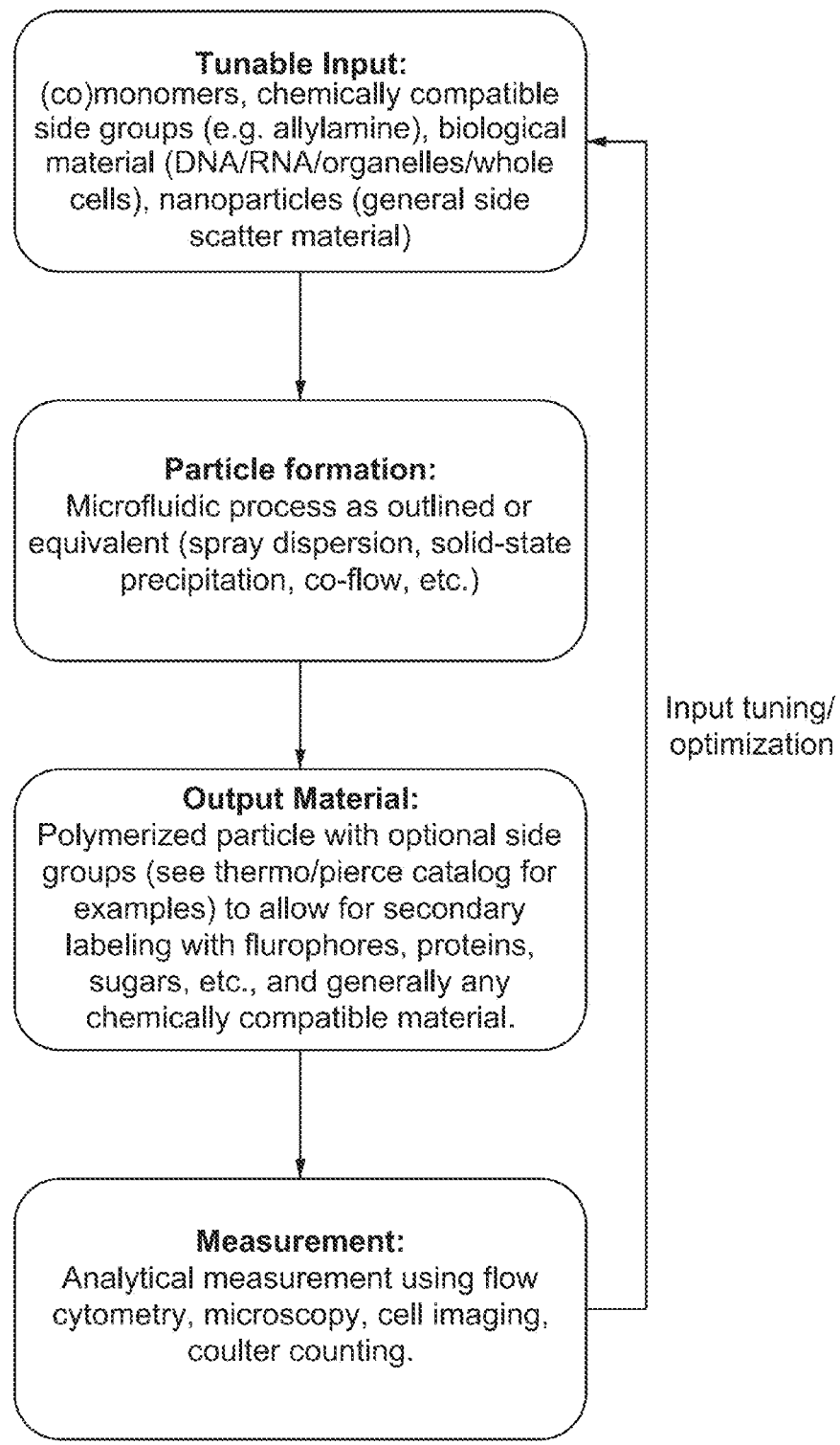
FIG. 10 shows one embodiment of hydrogel parameter tuning to match and/or mimic desired cell population metrics.

In one aspect, a composition comprising a plurality of hydrogel particles is provided, wherein the individual hydrogel particles of the plurality each has one or more optical properties substantially similar to one or more optical properties of a target cell. Each of the individual hydrogel particles of the plurality independently comprises a hydrogel which is synthesized by polymerizing one or more monomers, i.e., to form a homopolymer or copolymer. As discussed further below, the use of bifunctional monomers allows for the further derivatization of hydrogels, e.g., with fluorescent dyes, cell surface markers or epitope binding fragments thereof, or a combination thereof. An example of hydrogel parameter tuning to meet/match desired cell subpopulation metrics is provided at FIG. 10. Methods for tuning the properties of a hydrogel are described herein. The ability to adjust a range of parameters including hydrogel components and concentration of the same allows for the ability to tune a particle to mimic a wide range of cells, for example one of the cell types described herein.

As provided above, in one aspect, the present invention provides individual hydrogel particles each having one or more optical properties substantially similar to one or more optical properties of a target cell. In one embodiment, the one or more optical properties, is a side scatter profile, a forward scatter profile or a secondary marker profile, such as a fluorescence marker profile, for example a fluorescence marker profile of a fluorescently-labeled antibody that binds to the surface of the hydrogel particle. "Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

The present invention is based in part on the unexpected discovery that one or more optical properties of a hydrogel particle can be independently modulated by altering the composition of the hydrogel particle, for example, by altering the amount of initial monomer (or co-monomer) in the composition, by altering the surface functionalization, by altering the amount of a polymerization initiator or by altering the amount of crosslinker. For example, side scattering (SSC) can be modulated without substantially affecting forward scattering (FSC), and vice versa. Furthermore, the optical properties (e.g. refractive index) of hydrogel particles can be tuned without having a substantial effect on density of the particle. This is a surprising and useful feature, as hydrogel particles that serve as surrogates for cells in cytometric methods such as flow cytometry or (fluorescence-activated cell sorting) FACS require a minimal density in order to function in those assays.

In another aspect, a method for producing a hydrogel particle is provided, wherein the hydrogel particle has one or more optical properties substantially similar to the optical properties of one or more target cells. In one embodiment, the hydrogel particle has pre-determined optical properties. The optical property, in one embodiment, is SSC, FSC, fluorescence emission, or a combination thereof.

In yet another aspect, a method of calibrating a cytometric device for analysis of a target cell is provided. In one embodiment, the method comprises (a) inserting into the device a hydrogel particle having optical properties substantially similar to the optical properties of the target cell; b) measuring the optical properties of the hydrogel particle using the cytometric device, thereby calibrating the cytometric device for analysis of the target cell. Cytometric devices are known in the art, and include commercially available devices for performing flow cytometry and FACS.

As provided above, in one aspect of the invention, compositions comprising a plurality of hydrogel particles are provided. A hydrogel is a material comprising a macromolecular three-dimensional network that allows it to swell when in the presence of water, to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. Synthetically prepared hydrogels can be prepared by polymerizing a monomeric material to form a backbone and cross-linking the backbone with a crosslinking agent. As referred to herein, the term "hydrogel" refers to the macromolecular material whether dehydrated or in a hydrated state. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

In one embodiment, a hydrogel particle disclosed herein comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water. In another embodiment, a hydrogel particle has a water content of about 10 percent by weight to about 95 percent by weight, or about 20 percent by weight to about 95 percent by weight, or about 30 percent by weight to about 95 percent by weight, or about 40 percent by weight to about 95 percent by weight, or about 50 percent by weight to about 95 percent by weight, or about 60 percent by weight to about 95 percent by weight, or about 70 percent by weight to about 95 percent by weight, or about 80 percent by weight to about 95 percent by weight.

The hydrogels provided herein, in the form of particles, are synthesized by polymerizing one or more of the monomers provided herein. The synthesis is carried out to form individual hydrogel particles. The monomeric material (monomer) in one embodiment is polymerized to form a homopolymer. However, in another embodiment copolymers of different monomeric units (i.e., co-monomers) are synthesized and used in the methods provided herein. The monomer or co-monomers used in the methods and compositions described herein, in one embodiment, is a bifunctional monomer or includes a bifunctional monomer (where co-monomers are employed). In one embodiment, the hydrogel is synthesized in the presence of a crosslinker. In a further embodiment, embodiment, the hydrogel is synthesized in the presence of a polymerization initiator.

The amount of monomer can be varied by the user of the invention, for example to obtain a particular optical property that is substantially similar to that of a target cell. In one embodiment, the monomeric component(s) (i.e., monomer, co-monomer, bifunctional monomer, or a combination thereof, for example, bis/acrylamide in various crosslinking ratios, allyl amine or other co-monomers which provide chemical functionality for secondary labeling/conjugation or alginate is present at about 10 percent by weight to about 95 percent weight of the hydrogel. In a further embodiment, the monomeric component(s) is present at about 15 percent by weight to about 90 percent weight of the hydrogel, or about 20 percent by weight to about 90 percent weight of the hydrogel.

Examples of various monomers and cross-linking chemistries available for use with the present invention are provided in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes. For example, hydrazine (e.g., with an NHS ester compound) or EDC coupling reactions (e.g., with a maleimide compound) can be used to construct the hydrogels of the invention.

In one embodiment, a monomer for use with the hydrogels provided herein is lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof.

In one embodiment, one or more of the following monomers is used herein to form a hydrogel of the present invention: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate or a combination thereof.

In another embodiment, one or more of the following monomers is used herein to form a tunable hydrogel: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl)methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, as described in U.S. Pat. No. 6,657,030, which is incorporated by reference in its entirety herein for all purposes.

Both synthetic monomers and bio-monomers can be used in the hydrogels provided herein, to form synthetic hydrogels, bio-hydrogels, or hybrid hydrogels that comprise a synthetic component and a bio-component (e.g., peptide, protein, monosaccharide, disaccharide, polysaccharide, primary amines sulfhydryls, carbonyls, carbohydrates, carboxylic acids present on a biomolecule). For example, proteins, peptides or carbohydrates can be used as individual monomers to form a hydrogel that includes or does not include a synthetic monomer (or polymer) and in combination with chemically compatible co-monomers and crosslinking chemistries (see for example, the Thermo Scientific Crosslinking Technical Handbook entitled "Easy molecular bonding crosslinking technology," available at tools.lifetechnologies.com/content/sfs/brochures/1602163-Crosslinking-Reagents-Handbook.pdf, the disclosure of which is incorporated by reference in its entirety for all purposes.). Compatible crosslinking chemistries include, but are not limited to, amines, carboxyls, and other reactive chemical side groups. Representative reactive groups amenable for use in the hydrogels and monomers described herein are provided in Table 1, below.

TABLE 1

Crosslinker reactive groups amenable for bio-monomer conjugation

| Reactivity class | Target functional group | Reactive chemical group |
|---|---|---|
| Amine reactive | —NH$_2$ | NHS ester |
| | | Imidoester |
| | | Penafluorophenyl ester |
| | | Hydroxymethyl phosphine |
| Carboxyl-to-amine reactive | —COOH | Carbodiimide (e.g., EDC) |
| Sulfhydryl-reactive | —SH | Maeleimide |
| | | Haloacetyl (bromo- or iodo-) |
| | | Pyridylisulfide |
| | | Thiosulfonate |
| | | Vinylsulfonate |
| Aldehyde-reactive (oxidized sugars, carbonyls) | —CHO | Hydrazine |
| | | Alkoxyamine |
| Photo-reactive, i.e., nonselective, random insertion | Random | Diazirine |
| | | Aryl azide |
| Hydroxyl (nonaqueous)-reactive | —OH | Isocyanate |
| Azide-reactive | —N3 | phosphine |

In general, any form of polymerization chemistry/methods commonly known by those skilled in the art, can be employed to form polymers. In some embodiments, polymerization can be catalyzed by ultraviolet light-induced radical formation and reaction progression. In other embodiments, a hydrogel particle of the disclosure is produced by the polymerization of acrylamide or the polymerization of acrylate. For example, the acrylamide in one embodiment is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In one embodiment, an acrylate-functionalized poly(ethylene) glycol monomer is used as a hydrogel monomer. For example, the PEG in one embodiment is an acrylate or acrylamide functionalized PEG.

In some embodiments, a hydrogel particle comprises a monofunctional monomer polymerized with at least one bifunctional monomer. One example includes, but is not limited to, the formation of poly-acrylamide polymers using acrylamide and bis-acrylamide (a bifunctional monomer). In another embodiment, a hydrogel particle provided herein comprises a bifunctional monomer polymerized with a second bifunctional monomer. One example include, but is not limited to, the formation of polymers with mixed composition containing compatible chemistries such as acrylamide, bis-acrylamide, and bis-acrylamide structural congeners containing a wide range of additional chemistries. The range of chemically compatible monomers, bifunctional monomers, and mixed compositions is obvious to those skilled in the art and follows chemical reactivity principles know to those skilled in the art. (reference Thermo handbook and acrylamide polymerization handbook). See, for example, the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf) and the Polyacrylamide Emulsions Handbook (SNF Floerger, available at snf.com.au/downloads/Emulsion_Handbook_E.pdf), the disclosure of each of which is incorporated by reference in its entirety for all purposes.

In one embodiment, a hydrogel particle provided herein comprises a polymerizable monofunctional monomer and is a monofunctional acrylic monomer. Non-limiting examples of monofunctional acrylic monomers for use herein are acrylamide; methacrylamide; N-alkylacrylamides such as N-ethylacrylamide, N-isopropylacrylamide or N-tertbutylacrylamide; N-alkylmethacrylamides such as N-ethylmethacrylamide or Nisopropylmethacrylamide; N,N-dialkylacrylamides such as N,N-dimethylacrylamide and N,N-diethylacrylamide; N-[dialkylamino)alkyl]acrylamides such as N-[3dimethylamino) propyl]acrylamide or N-[3-(diethylamino)propyl]acrylamide; N-[(dialkylamino) alkyl]methacrylamides such as N-[3-dimethylamino)propyl]methacrylamide or N-[3-(diethylamino) propyl]methacrylamide; (dialkylamino)alkyl acrylates such as 2-(dimethylamino) ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore or cell surface receptor (or domain thereof).

In some embodiments, a bifunctional monomer is selected from the group consisting of: allyl amine, allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'methylene bismethacrylamide, N,N'-ethylene bisacrylamide, N,N'-ethylene bismethacrylamide, N,N'propylenebisacrylamide and N,N'-(1,2-dihydroxyethylene) bisacrylamide.

Higher-order branched chain and linear co-monomers can be substituted in the polymer mix to adjust the refractive index while maintaining polymer density, as described in U.S. Pat. No. 6,657,030, incorporated herein by reference in its entirety for all purposes.

In some embodiments, a hydrogel comprises a molecule that modulates the optical properties of the hydrogel. Molecules capable of altering optical properties of a hydrogel are discussed further below.

In one embodiment, an individual hydrogel particle or a plurality thereof comprises a biodegradable polymer as a hydrogel monomer. In one embodiment, the biodegradable polymer is a poly(esters) based on polylactide (PLA), polyglycolide (PGA), polycaprolactone (PCL), and their copolymers. In one embodiment, the biodegradable polymer is a carbohydrate or a protein, or a combination thereof. For example, in one embodiment, a monosaccharide, disaccharide or polysaccharide, (e.g., glucose, sucrose, or maltodextrin) peptide, protein (or domain thereof) is used as a hydrogel monomer. Other biodegradable polymers include poly(hydroxyalkanoate)s of the PHB-PHV class, additional poly(ester)s, and natural polymers, for example, modified poly(saccharide)s, e.g., starch, cellulose, and chitosan. In another embodiment, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma Aldrich (St. Louis, Mo.).

The protein in one embodiment comprises only natural amino acids. However, the invention is not limited thereto. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). The biodegradable polymer in one embodiment, is used as a co-monomer, i.e., in a mixture of monomers. The biodegradable polymer in one embodiment is a bifunctional monomer.

The biomonomer, in one embodiment, is functionalized with acrylamide or acrylate. For example, in one embodiment, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In one embodiment, an acrylamide or acrylate functionalized monosaccharide, disaccharide or polysaccharide is used as a polymerizable hydrogel monomer. In one embodiment, a structural polysaccharide is used as a polymerizable hydrogel monomer. In a further embodiment, the structural polysaccharide is an arabinoxylan, cellulose, chitin or a pectin. In another embodiment, alginic acid (alginate) is used as a polymerizable hydrogel monomer. In yet another embodiment, a glycosaminoglycan (GAG) is used as a polymerizable monomer in the hydrogels provided herein. In a further embodiment, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

Biocompatible monomers for use with the hydrogels described herein include in one embodiment, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in this invention include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan in one embodiment is used as a hydrogel monomer (either as a single monomer or as a co-monomer). Hyaluronan in one embodiment, is functionalized, for example with acrylate or acrylamide. Hyaluronan is a high molecular weight GAG composed of disaccharide repeating units of N-acetylglucosamine and glucuronic acid linked together through alternating $\beta$-1,4 and $\beta$-1,3 glycosidic bonds. In the human body, hyaluronate is found in several soft connective tissues, including skin, umbilical cord, synovial fluid, and vitreous humor. Accordingly, in one embodiment, where one or more optical properties of a skin cell, umbilical cord cell or vitreous humor cell is desired to be mimicked, in one embodiment, hyaluronan is used as a hydrogel monomer. Methods for fabricating hydrogel particles are described in Xu et al. (2012). Soft Matter. 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed $\beta$-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein in one embodiment is functionalized with acrylate or acrylamide.

In one embodiment, an individual hydrogel particle or a plurality thereof comprises a peptide, protein, a protein domain, or a combination thereof as a hydrogel monomer or plurality thereof. In a further embodiment, the protein is a structural protein, or a domain thereof, for example, such as silk, elastin, titin or collagen, or a domain thereof. In one embodiment, the protein is an extracellular matrix (ECM) component (e.g., collagen, elastin, proteoglycan). In even a further embodiment, the structural protein is collagen. In yet a further embodiment, the collagen is collagen type I, collagen type II or collagen type III or a combination thereof. In another embodiment, the hydrogel monomer comprises a proteoglycan. In a further embodiment, the proteoglycan is decorin, biglycan, testican, bikunin, fibromodulin, lumican, or a domain thereof.

In another embodiment, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In a further embodiment, the acrylate functionalized structural protein hydrogel monomer comprises a proteoglycan, e.g., decorin, biglycan, testican, bikunin, fibromodulin, lumican, or a domain thereof.

In one embodiment PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). *Proc. Natl. Acad. Sci. U.S.A.* 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). *Biomaterials* 30, 1089; Martino et al. (2011). *Sci. Trans. Med.* 3, 100ra89; Hu and Messersmith (2003). *J. Am. Chem. Soc.* 125, 14298, each of which is incorporated by reference in its entirety for all purposes.

In one embodiment, recombinant DNA methods are used to create proteins, designed to gel in response to changes in pH or temperature, for example, by the methods described by Petka et al. (1998). *Science* 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

Common cross linking agents that can be used to crosslink the hydrogels provided herein include but are not limited to ethylene glycol dimethacrylate (EGDMA), tetraethylene glycol dimethacrylate, and N,N'-15 methylenebisacrylamide. The range of additional crosslinking chemistries which can be used are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

In one embodiment, polymerization of a hydrogel is initiated by a persulfate or an equivalent initiator that catalyzes radical formation. The range of compatible initiators are known to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The persulfate can be any water-soluble persulfate. Non-limiting examples of water soluble persulfates are ammonium persulfate and alkali metal persulfates. Alkali metals include lithium, sodium and potassium. In some embodiments, the persulfate is ammonium persulfate or potassium persulfate. In a further embodiment, polymerization of the hydrogel provided herein is initiated by ammonium persulfate.

Polymerization of a hydrogel can be accelerated by an accelerant which can catalyze the formation of polymerization-labile chemical side groups. The range of possible accelerants is known to those skilled in the art and follow general chemical reactivity principles see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

The accelerant in one embodiment, is a tertiary amine. The tertiary amine can be any water-soluble tertiary amine. In one embodiment, an accelerant is used in the polymerization reaction and is N,N,N',N'tetramethylethylenediamine, 3-dimethylamino) propionitrile, or N,N,N',N'tetramethylethylenediamine (TEMED). In another embodiment, an accelerant is used in the polymerization reaction and isazobis (isobutyronitrile) (AIBN).

Figure 2:
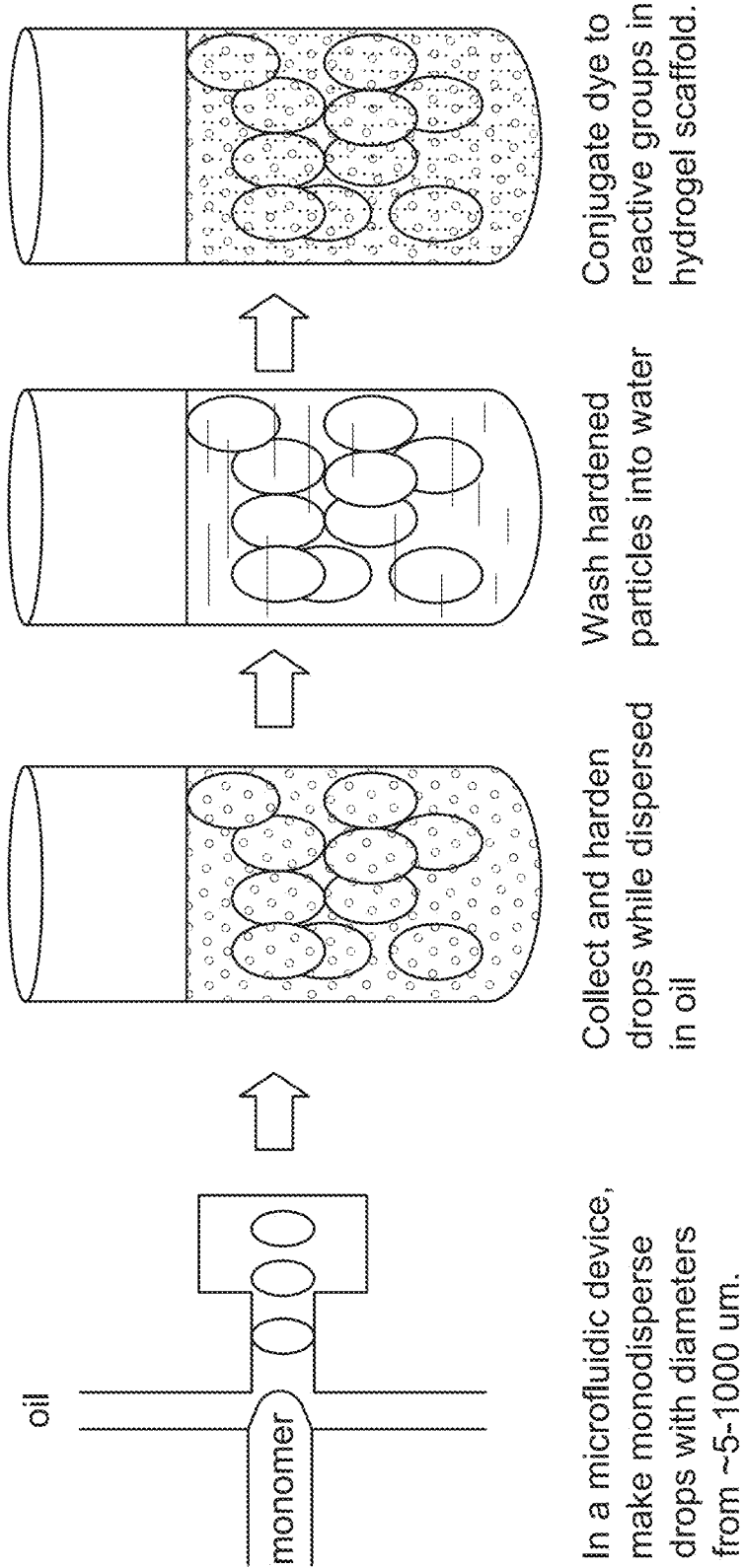
FIG. 2 depicts the process of producing labeled hydrogel particles of the disclosure.

As discussed above, the hydrogel for use in the compositions and methods described herein can include any of the monomeric units and crosslinkers as described herein, and in one aspect, are produced as hydrogel particles by polymerizing droplets (see, e.g., FIG. 2). Microfluidic methods of producing a plurality of droplets, including fluidic and rigidified droplets, are known to those of ordinary skill in the art, and described in US Patent Publication No. 2011/0218123 and U.S. Pat. No. 7,294,503, each incorporated herein by reference in their entireties for all purposes. Such methods provide for a plurality of droplets containing a first fluid and being substantially surrounded by a second fluid, where the first fluid and the second fluid are substantially immiscible (e.g., droplets containing an aqueous-based liquid being substantially surrounded by an oil based liquid).

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets. Average diameters of the particles can be measured, for example, by light scattering techniques. Average diameters of hydrogel particles in one embodiment, are tailored, for example by varying flow rates of the fluid streams of the first and second fluids within the channel(s) of a microfluidic device, or by varying the volume of the channel(s) of the microfluidic device.

Accordingly, the disclosure provides population of hydrogel particles comprising a plurality of hydrogel particles, wherein the population of hydrogel particles is substantially monodisperse.

The term microfluidic refers to a device, apparatus or system including at least one fluid channel having a cross-sectional dimension of less than 1 mm, and a ratio of length to largest cross-sectional dimension perpendicular to the channel of at least about 3:1. A micro fluidic device comprising a micro fluidic channel is especially well suited to preparing a plurality of mono disperse droplets.

Non-limiting examples of microfluidic systems that may be used with the present invention are disclosed in U.S. Patent Application Publication No. 2006/0163385; U.S. Patent Application Publication No. 2005/0172476; U.S. Patent Application Publication No. 2007/000342; International Patent Application Publication No. WO 2006/096571; U.S. Patent Application Publication No. 2007/0054119; U.S. Pat. No. 7,776,927; and International Patent Application Publication No. WO 2006/078841, each incorporated herein by reference in their entireties for all purposes.

Droplet size is related to microfluidic channel size. The micro fluidic channel may be of any size, for example, having a largest dimension perpendicular to fluid flow of less than about 5 mm or 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In some embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in some embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In some embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in diameter. In one embodiment, a hydrogel particle has a diameter in the range of 5 µm to 100 µm.

In some embodiments, a hydrogel particle of the disclosure is spherical in shape.

In some embodiments, a hydrogel particle of the disclosure does not comprise agarose.

Hydrogel particles in one embodiment, is carried by suspension polymerization, which is also referred to in the art as pearl, bead or granular polymerization (see Elbert (2011). *Acta Biomater.* 7, pp. 31-56, incorporated by reference herein in its entirety for all purposes). In suspension polymerization, the monomer is insoluble in the continuous phase, for example an aqueous monomer solution in a continuous oil phase. In suspension polymerization, polymerization initiation occurs within the monomer-rich droplets and with greater than one radical per droplet at any time. The monomer phase in one embodiment includes a monomer which can be a bifunctional monomer or a plurality of monomer species (co-monomers, which can be a plurality of bifunctional monomers. The monomer phase in one embodiment, includes an initiator and/or a crosslinking agent.

Emulsion polymerization can also be used to form the hydrogel particles described herein. In emulsion polymerization, the monomer has poor solubility in the continuous phase, similar to suspension polymerization, however, polymerization initiation occurs outside the monomer droplets (see Elbert (2011). *Acta Biomater.* 7, pp. 31-56, incorporated by reference herein in its entirety for all purposes). In emulsion polymerization embodiments, the initiator causes chain growth of the monomer (or co-monomers) dissolved in the continuous phase or monomer contained in micelles if surfactants are present.

In another embodiment, hydrogel particles are formed by precipitation polymerization, for example as described in Elbert (2011). *Acta Biomater.* 7, pp. 31-56, incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in one embodiment, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in one embodiment, results in a narrow size distribution of particles. Additional methods include but are not limited to lithographic particle formation (Helgeson et al. (2011). Curr. Opin. Colloid. Interface Sci. 16, pp. 106-117, incorporated by reference herein in its entirety for all purposes) membrane emulsification (e.g., by the micosieve emulsification technology techniques described by Nanomi B.V. (Netherlands)) and microchannel emulsification (Sugiura et al. (2002). Languimir 18, pp. 5708-5712, incorporated by reference herein in its entirety) and bulk emulsification (SNF Floerger, available at snf.com.au/downloads/Emulsion_Handbook_E.pdf, incorporated by reference herein in its entirety).

In one embodiment, hydrogel particles are formed within a microfluidic device having two oil channels that focus on a central stream of aqueous monomer solution. In this embodiment, droplets form at the interface of the two channels and central stream to break off droplets in water-in-oil emulsion. Once droplets are formed, in one embodiment, they are stabilized prior to polymerization, for example, by adding a surfactant to the oil phase. However, in another embodiment, droplets are not stabilized prior to polymerization. Polymerization of the monomer in one embodiment is triggered by adding an accelerator (e.g., N,N,N',N'tetramethylethylenediamine) to one or both of the oil channels after initial droplets are formed.

The aqueous monomer solution as provided above can include a single monomer species or a plurality of monomer species. The aqueous monomer solution can include co-monomers, a bifunctional monomer or a combination thereof. In one embodiment, the monomer or plurality of monomers can includes a bifunctional monomer, for example, one of the monomers described above. As described below, co-monomers can be used to modulate forward scatter or side scatter, for example, by adjusting the refractive index of the hydrogel particle.

In one embodiment, the central stream of aqueous monomer solution comprises a cross-linker, for example, N,N'-bisacrylamide. In a further embodiment, the central stream of aqueous monomer solution comprises a cross-linker and an accelerator, in addition to the monomer. In yet a further embodiment, the aqueous monomer solution comprises an initiator, for example an oxidizing agent such as ammonium persulfate.

Figure 11:
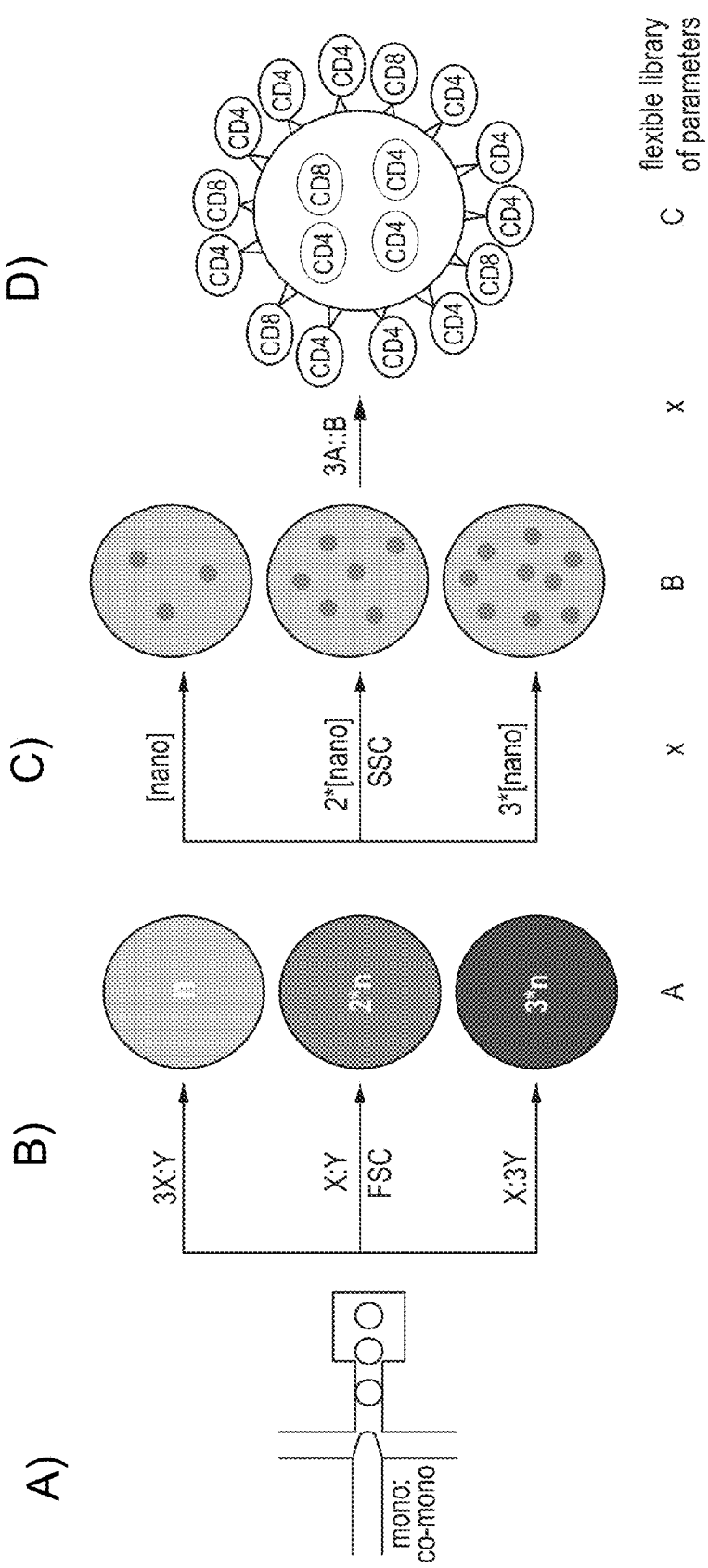
FIGS. 11 and 12 are diagrams showing embodiments of how to adjust the forward scatter, side scatter and surface properties of a hydrogel particle.
Figure 12:
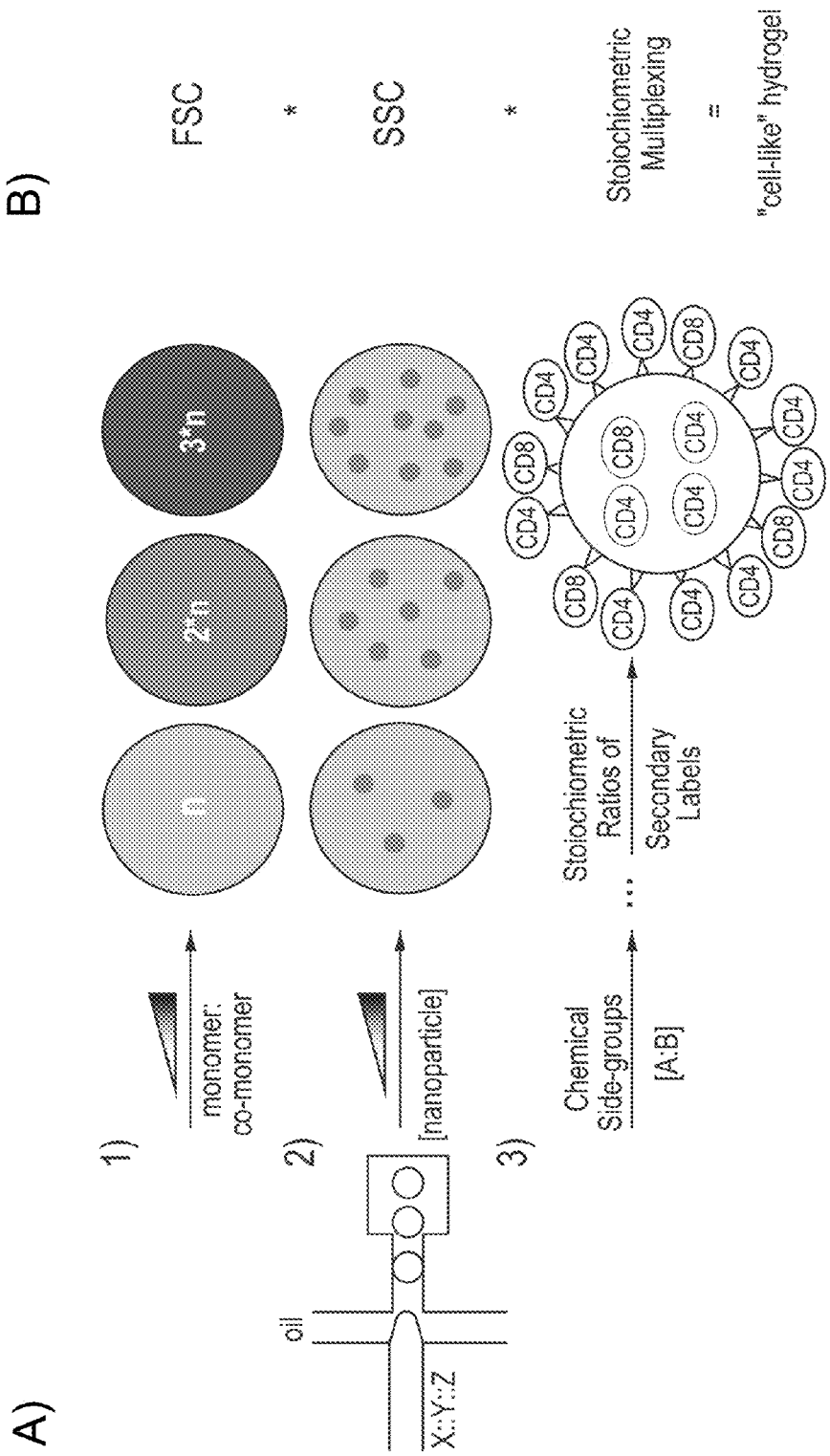

Forward scatter was modulated by adjusting the refractive index of the gel by adding co-monomers allyl acrylate and allyl methacrylate (see also FIGS. 11 and 12). Forward scatter can also be modulated with side scattering nanoparticles containing sufficient optical resolution/size/density including, but not limited to, higher density colloidal suspensions of silica and/or PMMA particles. Side scattering of the droplets was tuned by adding a colloidal suspension of silica nanoparticles and/or PMMA (poly(methyl methacrylate)) particles (~100 nm) to the central aqueous phase prior to polymerization (FIGS. 11 and 12).

In one embodiment, a bead, plurality of beads, biomolecule, or plurality of biomolecules is embedded (encapsulated) within the hydrogel particle. An encapsulated bead or biomolecule, in one embodiment, is employed to mimic one or more intracellular organelles of a target cell, or a cell after it engulfs a particle. In one embodiment, encapsulating or embedding a bead or biomolecule is accomplished at the time of hydrogel particle formation. For example, beads can be suspended in the appropriate concentration to allow for an average of one bead to be embedded/encapsulated in a single hydrogel particle. The bead suspension can be included, for example, within the aqueous solution of monomer. Similarly, a biomolecule or mixture of biomolecules can be incorporated into the aqueous solution of monomer to encapsulate the biomolecule or biomolecules.

Alternatively, once a hydrogel particle is formed, for example by the methods described above, in one embodiment, it can be further manipulated, for example, by embedding a bead, plurality of beads, biomolecule or plurality of biomolecules within the hydrogel particle.

Accordingly, in one aspect of the invention, a hydrogel comprising an embedded substance is provided.

In one embodiment, the embedded substance is an embedded molecule, for example a biomolecule. The biomolecule can be a single species or a plurality of different species. For example, a protein, peptide, carbohydrate, nucleic acid or combination thereof can be encapsulated within a hydrogel particle of the invention. Moreover, different nucleic acid molecules (e.g., of varying sequences or nucleic acid type such as genomic DNA, messenger RNA or DNA-RNA hybrids) can be encapsulated by the hydrogel particle of the invention. These can be comprised of any protein or nucleic acid as both forms of biological material contain labile chemical side-groups (or can be modified by commercial vendors (e.g., Integrated DNA Technology chemical side group modifications). Such side-groups are compatible with reaction chemistries commonly found in co-monomer compositions (e.g. acrylate chemistry, NETS-ester, primary amines, copper catalyzed click chemistry (Sharpless)). The range of possible embedded molecules which contain compatible chemistries is understood by those skilled in the art.

In one embodiment, different subpopulations of hydrogel particles are fabricated, each with a different concentration of biomolecule. In a further embodiment, the biomolecule is a nucleic acid, a protein, an intracellular ion such as calcium acid (or other biomolecule of the user's choosing, for example, calcium). In another embodiment, different subpopulations of hydrogel particles are fabricated, each with a different concentration of a drug substance. The drug substance in one embodiment is a biomolecule (i.e., a biologic, antibody, antibody drug conjugate, protein/enzyme, peptide, non-ribosomal peptide, or related molecule) or a small molecule synthetic drug (e.g., Type I/II/III polyketide, non-ribosomal peptide with bioactive properties, or other small molecule entity as generally classified by those skilled in the art).

In this regard, the present invention is particularly useful for determining assay resolution where cells are stained for their respective nucleic acid or protein content. In one embodiment, different populations of the hydrogel particles provided herein are encapsulated with known, differing amounts of an intracellular substance, e.g., nucleic acid or protein. Individual hydrogel particles are stained for the intracellular substance and fluorescence is measured via a cytometric device for the individual hydrogels of the various populations. This allows for a generation of a standard curve to establish the sensitivity and dynamic range of the intracellular assay. Once established, a sample can be run through the cytometer to detect target cell(s) if present, and to quantify the amount of intracellular substance in the respective target cell(s). In one embodiment, the embedded substance is an infectious disease biomarker, for example one of the infectious disease biomarkers in the Infectious Disease Biomarker Database (IDBD, see Yang et al. (2008) IDBD: Infectious Disease Biomarker Database. *Nucleic Acid Res.* 36, pp. D455-D460, incorporated by reference in its entirety for all purposes). In a further embodiment, the infectious disease biomarker is a biomarker of gastrointestinal infection, respiratory infection, neurological infection, urogenital infection, viral infection, hemorrhagic fever, zoonosis, arbovirus, antibiotics resistance or bioterrorism. In a further embodiment, the viral infection is an Ebola infection.

In one embodiment, the methods provided herein are used to determine the sensitivity and/or dynamic range of a cellular nucleic acid quantification assay. In this embodiment, a sample is interrogated for cell types within the sample (if present), and amount of cellular nucleic acid within the cell.

In another embodiment, the present invention provides a means for determining the resolution and/or sensitivity of an intracellular protein quantification assay. Hydrogel particles, in one embodiment, encapsulate known amounts of protein, at various concentrations, and subsequently stained with the appropriate protein antibody. Fluorescence is measured for the various particles to determine the sensitivity and/or dynamic range of the assay. The fluorescence values can then be compared to the values obtained from cells in a sample, to determine whether a target cell is present and whether it contains the intracellular protein, and the amount of the protein.

In one embodiment, individual hydrogel particles are tuned to have at least one optical property substantially similar to a circulating tumor cell or a fetal cell, present in maternal blood. The individual particles are embedded with known quantities of a biomolecule of interest. The particles are used to generate a standard curve for a biomolecule detection assay for the particular cell type.

As provided above, in one aspect of the invention, a hydrogel comprising an embedded substance is provided. In one embodiment, the embedded substance is a bead or plurality of beads. In one embodiment, a hydrogel particle is embedded with a single bead. In another embodiment, individual hydrogels the average number of embedded beads in a plurality of hydrogel particles is one.

In the case where a bead or plurality of beads are embedded into a hydrogel particle, in one embodiment, the optical properties of the bead or plurality of beads are used in combination with the FSC and SSC properties of the hydrogel particle for quality control of a flow cytometry assay. For example, the embedded bead in one embodiment is used as a control to calibrate the flow cytometer system, including the laser source, optics, and stream flow. In another embodiment, the embedded bead is used as a means for quantitating the amount of fluorescence in a sample, e.g., a particular cell. In this regard, embedded beads of various intensities can be used to generate a standard curve of fluorescence to determine whether a cell expresses a certain marker and at what level of expression.

In one embodiment, a bead with the diameter of about 1 μm to about 3 μm, about 2 μm to about 4 μm or about 3 μm to about 7 μm is embedded in a hydrogel provided herein. For example, in one embodiment, the bead has a diameter of about 3 μm to about 3.5 μm. In a further embodiment, the bead is a fluorescent bead. In another embodiment, the bead has a diameter of about 1 μm to about 2.5 μm or about 1.5 μm to about 3 μm. In a further embodiment, the bead is a fluorescent bead and can be stained either internally or at its surface. In even a further embodiment, the fluorescent bead is stained internally. Without wishing to be bound by theory, it is thought that internal staining insulates the fluorophores from environmental interactions that could cause variable fluorescence output.

As provided above, in one embodiment, the embedded bead is a fluorescence bead and in a further embodiment, the fluorescent bead is stained internally. It is within the skill in the art to select the appropriate fluorophore for use in conjunction with an embedded bead. In one embodiment, the bead is derivatized with one or more of the following fluorescent dyes: 6-carboxy-4',5'-dichloro-2',7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2 ', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and -6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4,4-difluoro-5,7-dimethyl-4-bora-3a,4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimefhyl-4-bora-3a,4a-diaza-s-indacene-3propionicacid; 4,4-difluoro-5,7-dimethyl-4-bora-3a,4adiaza-s-indacene-3-propionicacid succinimidyl ester; 4,4difluoro-5,7-dimefhyl-4-bora-3a,4a-diaza-s-indacene-3propionic acid; sulfosuccinimidyl ester or sodium salt; 6-((4,4-difluoro-5,7-dimethyl-4-bora-3a,4-diaza-s-indacene-3propionyl)amino)hexanoicacid; 6-((4,4-difluoro-5, 7 dimethyl-4-bora-3a,4a-diaza-s-indacene-3-propionyl)amino)hexanoic acid or succinimidyl ester; N-(4,4-difluoro 5,7-dimethyl-4-bora-3a,4a-diaza-s-indacene-3-propionyl) cysteic acid, succinimidyl ester or triethylammonium salt; 6-4,4-difluoro-1,3-dimethyl-5-(4-methoxyphenyl)-4-bora3a,4a4,4-difluoro-5,7-diphenyl-4-bora-3a,4a-diaza-sindacene-3-propionicacid; 4,4-difluoro-5, 7-diphenyl-4-bora3a, 4a-diaza-s-indacene-3-propionicacid succinimidyl ester; 4,4-difluoro-5-phenyl-4-bora-3a,4a-diaza-s-indacene-3-propionic acid; succinimidyl ester; 6-((4, 4-difluoro-5-phenyl-4 bora-3a,4a-diaza-s-indacene-3-propionyl)amino) hexanoicacid or succinimidyl ester; 4,4-difluoro-5-(4-phenyl-1,3butadienyl)-4-bora-3a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)amino-hexanoicacid or succinimidyl ester; 4,4-difluoro-5-styryl-4-bora-3a,4a-diaza-s-indacene-3-propionic acid; 4, 4-difluoro-5-styryl-4-bora-3a,4a-diaza-sindacene-3-propionic acid;

succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester; 4,4-difluoro-5-(2-thienyl)-4-bora-3a,4a-diaza-sindacene-3-propionic acid succinimidyl ester; 6-(((4-(4, 4-difluoro-5-(2-thienyl)-4-bora-3a,4adiazas-indacene-3-yl)phenoxy)acetyl)amino)hexanoic acid or succinimidyl ester; and 6#(4,4-difluoro-5-(2-thienyl)-4-bora-3a, 4a-diaza-s-indacene-3-yl)styryloxy)acetyl) aminohexanoic acid or succinimidyl ester, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid, cyanine dyes commercially available from Amersham-Pharmacia Biotech, including, but not limited to Cy3 NHS ester; Cy 5 NHS ester; Cy5.5 NHSester; and Cy7 NHS ester.

Other Fluorophores amenable for use with the present invention are provided in Table 2 below.

TABLE 2

| ID | NAME | Alternate Names | Excitation | Emission | Vendor/Source | ACS CAS# |
|---|---|---|---|---|---|---|
| ISAC148 | 6-carboxyfluorescein | | 492 | 518 | PubChem | 3301-79-9 |
| ISAC1 | 6-JOE | | 520 | 550 | LifeTechnologies | 82855-40-1 |
| ISAC2 | 7-AAD | | 545 | 647 | LifeTechnologies | 7240-37-1 |
| ISAC3 | Acridine Orange | | 503 | 525 | LifeTechnologies | 65-61-2 |
| ISAC4 | Alexa Fluor 350 | AF350; 2H-1-Benzopyran-6-sulfonic acid, 7-amino-3-[2-[(2,5-dioxo-1-pyrrolidinyl)oxy]-2-oxoethyl]-4-methyl-2-oxo-; 200554-19-4 | 343 | 442 | LifeTechnologies | 244636-14-4 |
| ISAC6 | Alexa Fluor 405 | AF405; C46H69N5O15S3 | 401 | 425 | LifeTechnologies | 791637-08-6 |
| ISAC7 | Alexa Fluor 430 | AF430; C32H42F3N3O9S | 433 | 541 | LifeTechnologies | 467233-94-9 |
| ISAC8 | Alexa Fluor 488 | AF488; C25H15Li2N3O13S2 | 496 | 519 | LifeTechnologies | 247144-99-6 |
| ISAC9 | Alexa Fluor 500 | AF500; CAS#798557-08-1 | 503 | 525 | LifeTechnologies | 798557-08-1 |
| ISAC10 | Alexa Fluor 514 | AF514; C31H27N3O13S2 | 517 | 542 | LifeTechnologies | 798557-07-0 |
| ISAC11 | Alexa Fluor 532 | AF532; 1H-Pyrano[3,2-f: 5,6-f']diindole-10,12-disulfonic acid, 5-[4-[[(2,5-dioxo-1-pyrrolidinyl)oxy]carbonyl]phenyl]-2,3,7,8-tetrahydro-2,3,3,7,7,8-hexamethyl-; 271795-14-3 | 532 | 553 | LifeTechnologies | 222159-92-4 |
| ISAC13 | Alexa Fluor 546 | AF546; C50H62Cl3N5O14S3 | 556 | 573 | LifeTechnologies | 247145-23-9 |
| ISAC14 | Alexa Fluor 555 | AF555 | 555 | 565 | LifeTechnologies | 644990-77-2 |
| ISAC15 | Alexa Fluor 568 | AF568 | 578 | 603 | LifeTechnologies | 247145-38-6 |
| ISAC16 | Alexa Fluor 594 | AF594 | 590 | 617 | LifeTechnologies | 247145-86-4 |
| ISAC17 | Alexa Fluor 610 | AF610; C58H77Cl3N6O14S3 | 612 | 628 | LifeTechnologies | 900528-62-3 |
| ISAC18 | Alexa Fluor 633 | AF633 | 632 | 647 | LifeTechnologies | 477780-06-6 |
| ISAC19 | Alexa Fluor 635 | AF635 | 633 | 647 | LifeTechnologies | 945850-82-8 |
| ISAC20 | Alexa Fluor 647 | AF647 | 650 | 665 | LifeTechnologies | 400051-23-2 |
| ISAC21 | Alexa Fluor 660 | AF660 | 663 | 690 | LifeTechnologies | 422309-89-5 |
| ISAC22 | Alexa Fluor 680 | AF680 | 679 | 702 | LifeTechnologies | 422309-67-9 |
| ISAC23 | Alexa Fluor 700 | AF700 | 702 | 723 | LifeTechnologies | 697795-05-4 |
| ISAC24 | Alexa Fluor 750 | AF750 | 749 | 775 | LifeTechnologies | 697795-06-5 |
| ISAC25 | Alexa Fluor 790 | AF790 | 784 | 814 | LifeTechnologies | 950891-33-5 |
| ISAC26 | AMCA | | 346 | 448 | SantaCruzBiotech | 106562-32-7 |
| ISAC27 | AmCyan | | 457 | 489 | BDBioscences | 1216872-44-4 |
| ISAC28 | APC | Allophycocyanin | 650 | 660 | SigmaAldrich | No names found |
| ISAC29 | APC-Alexa Fluor 680 | APC-AF680 | 655 | 704 | LifeTechnologies | No names found |
| ISAC30 | APC-Alexa Fluor 700 | APC-AF700 | 655 | 718 | LifeTechnologies | No names found |
| ISAC31 | APC-Alexa Fluor 750 | APC-AF750 | 650 | 775 | LifeTechnologies | No names found |
| ISAC32 | APC-Cy5.5 | Allophycocyanin-Cy5.5 | 650 | 695 | LifeTechnologies | No names found |
| ISAC33 | APC-Cy7 | Allophycocyanin-Cy7 | 650 | 767 | LifeTechnologies | No names found |
| ISAC34 | APC-eFluor 750 | eFluor750APC | 650 | 750 | eBioscience | No names found |
| ISAC35 | APC-eFluor 780 | eFluor780APC | 650 | 780 | eBioscience | 1472056-77-1 |
| ISAC36 | APC-H7 | H7APC | 650 | 765 | BDBioscences | 1366000-62-5 |
| ISAC37 | APC-Vio770 | Vio770APC | 652 | 775 | Miltenyl Biotech | No names found |
| ISAC38 | Atto488 | | 501 | 523 | ATTO-TEC | 923585-42-6 |
| ISAC39 | BIOTIN | | 0 | 0 | PubChem | 58-85-5 |
| ISAC40 | BODIPY FL | | 502 | 511 | SantaCruzBiotech | 165599-63-3 |
| ISAC41 | BODIPY R6G | 4,4-difluoro-5-phenyl-4-bora-3a,4a-diaza-s-indacene-3-propionic acid, succinimidyl ester; C22H18BF2N3O4 | 527 | 547 | LifeTechnologies | 335193-70-9 |
| ISAC43 | Brilliant Violet 421 | BV421 | 406 | 423 | Biolegend | 1428441-68-2 |
| ISAC44 | Brilliant Violet 510 | BV510 | 405 | 510 | Biolegend | No names found |
| ISAC45 | Brilliant Violet 570 | BV570 | 407 | 571 | Biolegend | 1428441-76-2 |
| ISAC46 | Brilliant Violet 605 | BV605 | 407 | 603 | Biolegend | 1632128-60-9 |
| ISAC47 | Brilliant Violet 612 | BV612 | 0 | 0 | Biolegend | 1428441-91-1 |
| ISAC48 | Brilliant Violet 650 | BV650 | 407 | 647 | Biolegend | No names found |
| ISAC49 | Brilliant Violet 711 | BV711 | 405 | 711 | Biolegend | No names found |
| ISAC50 | Brilliant Violet 785 | BV785 | 405 | 786 | Biolegend | 1613592-44-1 |
| ISAC53 | Calcein | CAS#: 1461-15-0 | 493 | 514 | LifeTechnologies | 1461-15-0 |
| ISAC51 | Calcein AM | | 496 | 517 | PubChem | 148504-34-1 |
| ISAC52 | Calcein Blue AM | | 360 | 445 | PubChem | 168482-84-6 |
| ISAC54 | Calcein Violet AM | | 400 | 452 | LifeTechnologies | No names found |

TABLE 2-continued

| ID | NAME | Alternate Names | Excitation | Emission | Vendor/Source | ACS CAS# |
|---|---|---|---|---|---|---|
| ISAC55 | Calcium Sensor Dye eFluor 514 | | 490 | 514 | eBioscience | No names found |
| ISAC56 | Cascade Blue | | 401 | 420 | PubChem | 1325-87-7 |
| ISAC57 | Cascade Yellow | | 400 | 550 | Synchem UG & Co. KG | 220930-95-0 |
| ISAC58 | Cell Proliferation Dye eFluor 450 | | 405 | 445 | eBioscience | No names found |
| ISAC59 | Cell Proliferation Dye eFluor 670 | | 652 | 672 | eBioscience | No names found |
| ISAC60 | CellTrace Violet Cell Proliferation | | 392 | 455 | LifeTechnologies | No names found |
| ISAC61 | CellVue Claret | | 655 | 657 | SigmaAldrich | 1042142-46-0 |
| ISAC62 | CFSE | | 492 | 525 | SantaCruzBiotech | 150347-59-4 |
| ISAC63 | CPC | O□cresolphthalein complexone | 488 | 660 | Chemical Book | 2411-89-4 |
| ISAC65 | Cy2 | | 492 | 507 | GElifesciences | 102185-03-5 |
| ISAC66 | Cy3 | | 552 | 566 | GElifesciences | 146368-16-3 |
| ISAC67 | Cy3.5 | | 581 | 598 | GElifesciences | 189767-45-1 |
| ISAC68 | Cy5 | | 633 | 670 | GElifesciences | 144377-05-9 |
| ISAC69 | Cy5.5 | | 677 | 695 | GElifesciences | 210892-23-2 |
| ISAC70 | Cy7 | | 743 | 767 | GElifesciences | 169799-14-8 |
| ISAC71 | Cychrome | | 565 | 667 | BDBioscences | 245670-67-1 |
| ISAC73 | CyQUANT DNA | | 502 | 522 | LifeTechnologies | No names found |
| ISAC74 | CyTRAK Orange | 1,5-bis{[2-(di-methylamino) ethyl]amino}-4,8-dihydroxyanthracene-9,10-dione | 514 | 609 | Abcam (eBioscience) | 1195771-25-5 |
| ISAC76 | DAPI | | 358 | 462 | PubChem | 47165-04-8 |
| ISAC77 | DCFH | | 505 | 525 | SigmaAldrich | 106070-31-9 |
| ISAC79 | DiA | DiA; 4-Di-16-ASP (4-(4-(Dihexadecylamino)styryl)-N-Methylpyridinium Iodide); C46H79IN2 | 455 | 586 | LifeTechnologies | 371114-38-4 |
| ISAC81 | DiD | DiD' solid; DiIC18(5) solid (1,1'-Dioctadecyl-3,3,3',3'-Tetramethylindodicarbocyanine, 4-Chlorobenzenesulfonate Salt); C67H103ClN2O3S | 647 | 669 | LifeTechnologies | 127274-91-3 |
| ISAC84 | DiI | DiI Stain (1,1'-Dioctadecyl-3,3,3',3'-Tetramethylindocarbocyanine Perchlorate ('DiI'; DiIC18(3))); C59H97ClN2O4; 3H-Indolium, 2-(3-(1,3-dihydro-3,3-dimethyl-1-octadecyl-2H-indol-2-ylidene)-1-propenyl)-3,3-dimethyl-1-octadecyl-, perchlorate/ | 550 | 568 | LifeTechnologies | 41085-99-8 |
| ISAC88 | DiO | DiO'; DiOC18(3) (3,3'-Dioctadecyloxacarbocyanine Perchlorate); C53H85ClN2O6; Benzoxazolium, 3-octadecyl-2-[3-(3-octadecyl-2(3H)-benzoxazolylidene)-1-propenyl]-, perchlorate/ | 489 | 506 | LifeTechnologies | 34215-57-1 |
| ISAC92 | DiR | DiR'; DiIC18(7) (1,1'-Dioctadecyl-3,3,3',3'-Tetramethylindotricarbocyanine Iodide); C63H101IN2 | 750 | 781 | LifeTechnologies | 100068-60-8 |
| ISAC95 | DRAQ5 | | 645 | 683 | CellSignallingTech | 254098-36-7 |
| ISAC96 | DRAQ7 | | 599 | 694 | CellSignallingTech | 1533453-55-2 |
| ISAC97 | DsRED | | 532 | 595 | Clontech | 469863-23-8 |
| ISAC98 | dsRed2-RFP | | 555 | 582 | Clontech | No names found |
| ISAC99 | DY547 | 547 Dyomics | 557 | 574 | Dynomics | 947138-67-2 |
| ISAC100 | DY634 | 634 Dyomics | 635 | 658 | Dynomics | 1189010-49-8 |
| ISAC101 | DY647 | 647 Dyomics | 650 | 665 | Dynomics | 890317-39-2 |
| ISAC102 | DyLight 350 | DL350 | 353 | 432 | PierceNet | 1436849-83-0 |
| ISAC103 | DyLight 405 | DL405 | 400 | 420 | PierceNet | 1051927-09-3 |
| ISAC104 | DyLight 488 | DL488 | 493 | 518 | PierceNet | 1051927-12-8 |
| ISAC105 | DyLight 549 | DL549 | 562 | 576 | JacksonImmunoRes | 1051927-13-9 |
| ISAC106 | DyLight 550 | DL550 | 562 | 576 | PierceNet | 1340586-78-8 |
| ISAC107 | DyLight 594 | DL594 | 593 | 618 | PierceNet | 1268612-00-5 |
| ISAC108 | DyLight 633 | DL633 | 638 | 658 | PierceNet | 1051927-14-0 |
| ISAC109 | DyLight 649 | DL649 | 654 | 670 | JacksonImmunoRes | 1051927-15-1 |
| ISAC110 | DyLight 650 | DL650 | 652 | 672 | PierceNet | 1364214-13-0 |
| ISAC111 | DyLight 680 | DL680 | 682 | 712 | PierceNet | 1051927-24-2 |
| ISAC112 | DyLight 800 | DL800 | 777 | 794 | PierceNet | 1051927-23-1 |
| ISAC113 | EB | Ethidium Bromide | 523 | 604 | SigmaAldrich | 1239-45-8 |
| ISAC114 | ECD | | 563 | 613 | LifeTechnologies | 88475-75-6 |
| ISAC116 | ECFP | enhanced cyan fluorescent protein | 435 | 477 | MyBiosource | No names found |
| ISAC118 | EdU | EdU(5-ethynyl-2\u2032-deoxyuridine); C11H12N2O5 | 0 | 0 | LifeTechnologies | 61135-33-9 |
| ISAC120 | EdU Alexa Fluor 488 | | 496 | 516 | LifeTechnologies | No names found |
| ISAC121 | EdU Alexa Fluor 647 | | 650 | 665 | LifeTechnologies | No names found |
| ISAC122 | EdU Pacific Blue | | 405 | 455 | LifeTechnologies | No names found |

TABLE 2-continued

| ID | NAME | Alternate Names | Excitation | Emission | Vendor/Source | ACS CAS# |
|---|---|---|---|---|---|---|
| ISAC123 | eFluor 450 | | 400 | 450 | eBioscience | 1592653-87-6 |
| ISAC124 | eFluor 450 Fixable Viability Dye | | 400 | 450 | eBioscience | No names found |
| ISAC125 | eFluor 490 | | 350 | 490 | eBioscience | No names found |
| ISAC126 | eFluor 506 Fixable Viability Dye | | 420 | 506 | eBioscience | No names found |
| ISAC127 | eFluor 525 | | 350 | 525 | eBioscience | No names found |
| ISAC128 | eFluor 565 | | 350 | 565 | eBioscience | No names found |
| ISAC129 | eFluor 585 | | 350 | 604 | eBioscience | No names found |
| ISAC130 | eFluor 605 | | 350 | 605 | eBioscience | 1248429-27-7 |
| ISAC131 | eFluor 615 | | 590 | 622 | eBioscience | No names found |
| ISAC132 | eFluor 625 | | 350 | 625 | eBioscience | No names found |
| ISAC133 | eFluor 650 | | 350 | 650 | eBioscience | No names found |
| ISAC134 | eFluor 660 | | 633 | 658 | eBioscience | 1634649-16-3 |
| ISAC135 | eFluor 670 | | 0 | 0 | eBioscience | 1437243-07-6 |
| ISAC136 | eFluor 700 | | 350 | 700 | eBioscience | No names found |
| ISAC137 | eFluor 710 | | 350 | 710 | eBioscience | No names found |
| ISAC138 | eFluor 780 Fixable Viability Dye | | 755 | 780 | eBioscience | No names found |
| ISAC139 | EGFP | enhanced green fluorescent protein | 480 | 510 | MyBiosource | No names found |
| ISAC141 | Emerald 300 | | 289 | 530 | LifeTechnologies | No names found |
| ISAC142 | Eosin | | 525 | 546 | SigmaAldrich | 17372-87-1 |
| ISAC143 | Ethidium Homodimer-1 | | 528 | 617 | SigmaAldrich | 61926-22-5 |
| ISAC144 | Ethidium Monoazide EMA | | 510 | 590 | SigmaAldrich | 58880-05-0 |
| ISAC145 | EYFP | enhanced yellow fluorescent protein | 515 | 528 | MyBiosource | No names found |
| ISAC147 | FAM | | 492 | 518 | PubChem | 76823-03-5 |
| ISAC149 | FITC | Fluorescein | 500 | 520 | PubChem | 27072-45-3 |
| ISAC153 | Fluo-3 | C51H50Cl2N2O23; Glycine, N-[4-[6-[(acetyloxy)methoxy]-2,7-dichloro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-, (acetyloxy)methyl ester/ | 506 | 526 | LifeTechnologies | 123632-39-3 |
| ISAC155 | Fluo-4 | C51H50F2N2O23; Glycine, N-[4-[6-[(acetyloxy)methoxy]-2,7-difluoro-3-oxo-3H-xanthen-9-yl]-2-[2-[2-[bis[2-[(acetyloxy)methoxy]-2-oxoethyl]amino]-5-methylphenoxy]ethoxy]phenyl]-N-[2-[(acetyloxy)methoxy]-2-oxoethyl]-, (acetyloxy)methyl ester/ | 494 | 516 | LifeTechnologies | 273221-59-3 |
| ISAC152 | FLMA | Fluorescein-5-maleimide | 495 | 520 | PierceNet | 75350-46-8 |
| ISAC157 | Fluoro-Emerald | Dextran, Fluorescein, 10,000 MW, Anionic, Lysine Fixable | 495 | 523 | LifeTechnologies | 194369-11-4 |
| ISAC159 | Fura Red | | | | LifeTechnologies | 149732-62-7 |
| ISAC162 | Fura3 | Fura-2 LeakRes (AM) | 325 | 510 | SigmaAldrich | 172890-84-5 |
| ISAC164 | FxCycle Far Red | | 640 | 658 | LifeTechnologies | No names found |
| ISAC165 | FxCycle Violet | C16H17Cl2N5; 1H-Indole-6-carboximidamide, 2-[4-(aminoiminomethyl)phenyl]-, dihydrochloride/ | 358 | 462 | LifeTechnologies | 28718-90-3 |
| ISAC167 | GFP | green fluorescent protein | 488 | 515 | MyBiosource | No names found |
| ISAC169 | GFP Violet Excited | | 398 | 515 | MyBiosource | No names found |
| ISAC170 | GFP-Vex1 | | 398 | 515 | MyBiosource | No names found |
| ISAC171 | HiLyte Fluor 488 | | 501 | 527 | Anaspec | 1051927-29-7 |
| ISAC172 | HiLyte Fluor 555 | | 550 | 566 | Anaspec | 1051927-30-0 |
| ISAC173 | HiLyte Fluor 647 | | 649 | 674 | Anaspec | 925693-87-4 |
| ISAC174 | HiLyte Fluor 680 | | 0 | 0 | Anaspec | 1051927-34-4 |
| ISAC175 | HiLyte Fluor 750 | | 754 | 778 | Anaspec | 1051927-32-2 |
| ISAC176 | Hoechst 33258 | | 345 | 455 | SigmaAldrich | 23491-45-4 |
| ISAC177 | Hoechst 33342 | bisBenzimide H 33342 trihydrochloride | 343 | 455 | SigmaAldrich | 23491-52-3 |
| ISAC179 | Hydroxycoumarin | C10H6O5; 7-hydroxycoumarin-3-carboxylic acid; 2H-1-Benzopyran-3-carboxylic acid, 7-hydroxy-2-oxo-/; 4-chloromethyl-7-hydroxycoumarin | 360 | 450 | LifeTechnologies | 43070-85-5 |
| ISAC183 | Indo-1 | Indo-1 AM Calcium Sensor Dye; C47H51N3O22; 1H-Indole-6-carboxylic acid, 2-[4-[bis[2-[(acetyloxy)methoxy]-2-oxoethyl]amino]-3-[2-[2-[bis[2-[(acetyloxy)methoxy]-2-oxoetyl]amino]-5-methylphenoxy]ethoxy]phenyl]-, (acetyloxy)methyl ester/ | 347 | 480 | LifeTechnologies | 96314-96-4 |
| ISAC187 | JC-1 | 5,5',6,6'-tetrachloro-1,1',3,3'-tetraethylbenzimidazolylcarbocyanine iodide; C25H27Cl4IN4 | 593 | 595 | LifeTechnologies | 3520-43-2 |
| ISAC189 | Krome Orange | | 398 | 530 | Beckman Coulter | 1558035-65-6 |
| ISAC190 | Leadmium | | 490 | 520 | LifeTechnologies | No names found |

TABLE 2-continued

| ID | NAME | Alternate Names | Excitation | Emission | Vendor/Source | ACS CAS# |
|---|---|---|---|---|---|---|
| ISAC191 | LIVE/DEAD Fixable Aqua Dead Cell Stain | Aqua LIVE/DEAD | 367 | 526 | LifeTechnologies | No names found |
| ISAC193 | LIVE/DEAD Fixable Blue Dead Cell Stain | Blue LIVE/DEAD | 343 | 442 | LifeTechnologies | No names found |
| ISAC195 | LIVE/DEAD Fixable Far Red Dead Cell Stain | | 650 | 670 | LifeTechnologies | No names found |
| ISAC196 | LIVE/DEAD Fixable Green Dead Cell Stain | Green LIVE/DEAD | 498 | 525 | LifeTechnologies | No names found |
| ISAC198 | LIVE/DEAD Fixable Near-IR Dead Cell Stain | | 752 | 776 | LifeTechnologies | No names found |
| ISAC199 | LIVE/DEAD Fixable Red Dead Cell Stain | | 594 | 612 | LifeTechnologies | No names found |
| ISAC200 | LIVE/DEAD Fixable Violet Dead Cell Stain | Violet LIVE/DEAD | 403 | 455 | LifeTechnologies | No names found |
| ISAC202 | LIVE/DEAD Fixable Yellow Dead Cell Stain | Yellow LIVE/DEAD | 401 | 551 | LifeTechnologies | No names found |
| ISAC204 | Lucifer Yellow | C13H9Li2N5O9S2; 1H-Benz[de]isoquinoline-5,8-disulfonic acid, 6-amino-2-[(hydrazinocarbonyl)amino]-2,3-dihydro-1,3-dioxo-, dilithium salt/ | 428 | 544 | LifeTechnologies | 82446-52-4 |
| ISAC206 | Magnesium Green | C33H17Cl2K5N2O13; Glycine, N-[2-(carboxymethoxy)-4-[[(2',7'-dichloro-3',6'-dihydroxy-3-oxospiro[isobenzofuran-1(3H),9'-[9H]xanthen]-5-yl)carbonyl]amino]phenyl]-N-(carboxymethyl)-, pentapotassium salt/ | 507 | 531 | LifeTechnologies | 170516-41-3 |
| ISAC208 | Marina Blue | C16H11F2NO7; 2,5-Pyrrolidinedione, 1-[[((6,8-difluoro-7-hydroxy-4-methyl-2-oxo-2H-1-benzopyran-3-yl)acetyl]oxy]-/; | 364 | 461 | LifeTechnologies | 215868-23-8 |
| ISAC210 | mBanana | | 540 | 553 | Clontech | 1114839-40-5 |
| ISAC211 | mCherry | | 587 | 610 | Clontech | 1628764-31-7 |
| ISAC212 | mCitrine | | 516 | 529 | Not Commercialized | 1357606-54-2 |
| ISAC213 | MethylCoumarin | AMCA-X, SE (6-((7-Amino-4-Methylcoumarin-3-Acetyl)amino)Hexanoic Acid, Succinimidyl Ester); C22H25N3O7 | 360 | 448 | LifeTechnologies | 1333-47-7 |
| ISAC216 | MitoTracker Green | C34H28Cl5N3O; Benzoxazolium, 2-[3-[5,6-dichloro-1,3-bis[[4-(chloromethyl)phenyl]methyl]-1,3-dihydro-2H-benzimidazol-2-ylidene]-1-propenyl]-3-methyl-, chloride/ | 490 | 512 | LifeTechnologies | 1304563-13-0 |
| ISAC218 | MitoTracker Orange | C24H24Cl2N2O | 550 | 575 | LifeTechnologies | No names found |
| ISAC219 | MitoTracker Red | C39H36Cl5N3 | 578 | 598 | LifeTechnologies | No names found |
| ISAC220 | mOrange | | 548 | 562 | Clontech | 1114839-60-9 |
| ISAC221 | mPlum | | 590 | 649 | Clontech | 1399820-93-9 |
| ISAC222 | mRaspberry | | 597 | 624 | Clontech | 1452799-41-5 |
| ISAC223 | mRFP1 | | 584 | 607 | Not Commercialized | 1452799-30-2 |
| ISAC224 | mStrawberry | | 574 | 596 | Clontech | 1114834-99-9 |
| ISAC225 | Na-Green | Sodium Green ™, tetra(tetramethylammonium) salt; C84H100Cl4N8O19 | 506 | 532 | LifeTechnologies | 195244-55-4 |
| ISAC228 | Nile Red | C20H18N2O2; 5H-Benzo[\u03B1]phenoxazin-5-one, 9-(diethylamino)-/ | 559 | 637 | LifeTechnologies | 7385-67-3 |
| ISAC230 | Oregon Green | | 491 | 519 | LifeTechnologies | 195136-58-4 |
| ISAC232 | Oregon Green 488-X, succinimidyl ester | | 500 | 525 | LifeTechnologies | 890416-18-9 |
| ISAC233 | Oregon Green 514 | Oregon Green ® 514 carboxylic acid, succinimidyl ester; C26H12F5NO9S | 510 | 532 | LifeTechnologies | 198139-53-6 |
| ISAC235 | Pacific Blue | PacBlue; Pacific Blue ™succinimidyl ester; C14H7F2NO7 | 405 | 455 | LifeTechnologies | 215868-31-8 |
| ISAC236 | Pacific Blue succinimidyl ester | | 405 | 455 | LifeTechnologies | 215868-33-0 |
| ISAC237 | Pacific Orange | PacOrange | 403 | 551 | LifeTechnologies | 1122414-42-9 |
| ISAC240 | PE-Alexa Fluor 610 | RPE-AF610 | 563 | 628 | LifeTechnologies | No names found |
| ISAC241 | PE-Alexa Fluor 647 | RPE-AF647 | 567 | 669 | LifeTechnologies | No names found |
| ISAC242 | PE-Alexa Fluor 680 | RPE-AF680 | 570 | 702 | LifeTechnologies | No names found |
| ISAC243 | PE-Alexa Fluor 700 | RPE-AF700 | 563 | 720 | LifeTechnologies | No names found |
| ISAC244 | PE-Alexa Fluor 750 | RPE-AF750 | 570 | 776 | AbD Serotec | No names found |
| ISAC245 | PE-CF594 | PE-Dazzle 594 | 564 | 612 | BDBioscences | 1613592-67-8 |
| ISAC72 | PE-Cy5 | | 565 | 667 | BDBioscences | 1448849-77-1 |
| ISAC248 | PE-Cy5.5 | | 563 | 695 | AbD Serotec | No names found |
| ISAC249 | PE-Cy7 | | 563 | 760 | AbD Serotec | 1429496-42-3 |
| ISAC250 | PE-DY590 | | 563 | 599 | LSBio | No names found |
| ISAC251 | PE-DY647 | | 563 | 672 | LSBio | No names found |
| ISAC252 | PerCP | | 490 | 675 | AbD Serotec | 422551-33-5 |
| ISAC253 | PerCP-Cy5.5 | | 488 | 695 | AbD Serotec | 1474026-81-7 |
| ISAC254 | PerCP-eFluor 710 | | 488 | 710 | eBioscience | 1353683-31-4 |

TABLE 2-continued

| ID | NAME | Alternate Names | Excitation | Emission | Vendor/Source | ACS CAS# |
|---|---|---|---|---|---|---|
| ISAC115 | PE-Texas Red | | 563 | 613 | LifeTechnologies | No names found |
| ISAC256 | PE-Vio770 | | 565 | 775 | Miltenyl Biotech | No names found |
| ISAC257 | pHrodo | pHrodo ™ Red, succinimidyl ester (pHrodo ™ Red, SE); pHrodo ™ Green STP Ester | 560 | 586 | LifeTechnologies | No names found |
| ISAC260 | pHrodo Green STP Ester | | 560 | 586 | LifeTechnologies | No names found |
| ISAC258 | pHrodo Red, succinimidyl ester | | 560 | 586 | LifeTechnologies | No names found |
| ISAC261 | Phycocyanin | | 617 | 646 | SigmaAldrich | 11016-15-2 |
| ISAC262 | PicoGreen | Quant-iT ™ PicoGreen ® dsDNA Reagent | 502 | 522 | LifeTechnologies | 177571-06-1 |
| ISAC264 | PKH2 | PKH2 Green Fluorescent Cell Linker | 490 | 504 | SigmaAldrich | 145687-07-6 |
| ISAC266 | PKH26 | PKH26 Red Fluorescent Cell Linker | 551 | 567 | SigmaAldrich | 154214-55-8 |
| ISAC268 | PKH67 | PKH67 Green Fluorescent Cell Linker | 490 | 504 | SigmaAldrich | 257277-27-3 |
| ISAC270 | POPO-1 | C41H54I4N6O2; Benzoxazolium, 2,2'-[1,3-propanediylbis[(dimethyliminio)-3,1-propanediyl-1(4H)-pyridinyl-4-ylidenemethylidyne]]bis[3-methyl]-, tetraiodide/ | 433 | 457 | LifeTechnologies | 169454-15-3 |
| ISAC272 | PO-PRO-1 | C20H27I2N3O; Benzoxazolium, 3-methyl-2-[[1-[3-(trimethylammonio)propyl]-4(1H)-pyridinylidene]methyl]-, diiodide/; | 435 | 457 | LifeTechnologies | 157199-56-9 |
| ISAC274 | Propidium Iodide | C27H34I2N4; Phenanthridinium, 3,8-diamino-5-[3-(diethylmethylammonio)propyl]-6-phenyl-, diiodide | 350 | 617 | LifeTechnologies | 25535-16-4 |
| ISAC276 | PURE | | 0 | 0 | Not Commercialized | No names found |
| ISAC277 | Pyronin Y | | 547 | 560 | SigmaAldrich | 92-32-0 |
| ISAC278 | Qdot 525 | | 350 | 525 | LifeTechnologies | 885332-45-6 |
| ISAC279 | Qdot 545 | | 350 | 545 | LifeTechnologies | 948906-89-6 |
| ISAC280 | Qdot 565 | | 350 | 565 | LifeTechnologies | 859509-02-7 |
| ISAC281 | Qdot 585 | | 350 | 585 | LifeTechnologies | 885332-46-7 |
| ISAC282 | Qdot 605 | | 350 | 605 | LifeTechnologies | 849813-89-4 |
| ISAC283 | Qdot 625 | | 350 | 625 | LifeTechnologies | 1144512-19-5 |
| ISAC284 | Qdot 655 | | 350 | 655 | LifeTechnologies | 674287-64-0 |
| ISAC285 | Qdot 705 | | 350 | 705 | LifeTechnologies | 885332-47-8 |
| ISAC286 | Qdot 800 | | 350 | 800 | LifeTechnologies | 885332-50-3 |
| ISAC287 | RD1 | R-Phycoerythrin | 563 | 578 | LifeTechnologies | 1376573-14-6 |
| ISAC295 | Rhodamine | | 550 | 570 | LifeTechnologies | No names found |
| ISAC290 | Rho 110 | Rhodamine 110 | 497 | 520 | LifeTechnologies | 13558-31-1 |
| ISAC293 | Rho 123 | Rhodamine 123 | 507 | 529 | LifeTechnologies | 62669-70-9 |
| ISAC296 | Rhodamine Green | Rhodamine Green ™carboxylic acid, succinimidyl ester, hydrochloride; C25H18ClN3O7 | 505 | 527 | LifeTechnologies | 189200-71-3 |
| ISAC297 | Rhodamine Green carboxylic acid, succinimidyl ester, hydrochloride | | 505 | 527 | LifeTechnologies | 254732-34-8 |
| ISAC298 | Rhodamine Red | | 573 | 591 | LifeTechnologies | 99752-92-8 |
| ISAC299 | Rhodamine Red-X | Rhodamine Red ™-X, succinimidyl ester; C37H44N4O10S2 | 570 | 576 | LifeTechnologies | 178623-12-6 |
| ISAC300 | Rhodamine Red-X, succinimidyl ester | | 570 | 576 | LifeTechnologies | 178623-13-7 |
| ISAC301 | RiboFlavin | | 266 | 531 | SigmaAldrich | 83-88-5 |
| ISAC239 | R-Phycoerythrin | PE | 563 | 578 | LifeTechnologies | 11016-17-4 |
| ISAC303 | SNARF-1 carboxylic acid, acetate, succinimidyl ester | | 549 | 586 | LifeTechnologies | No names found |
| ISAC302 | SNARF-1 pH 6 | SNARF ®-1 carboxylic acid, acetate, succinimidyl ester; C33H24N2O9 | 549 | 586 | LifeTechnologies | No names found |
| ISAC304 | SNARF-1 pH 9 | | 576 | 640 | LifeTechnologies | No names found |
| ISAC305 | Spectral Red | | 506 | 665 | MyBiosource | No names found |
| ISAC306 | SureLight P1 | | 545 | 667 | Abcam (Columbia Biosciences) | No names found |
| ISAC307 | SureLight P3 | | 614 | 662 | Abcam | 1365659-06-8 |
| ISAC308 | SureLight PBXL-3 | | 614 | 662 | Abcam | No names found |
| ISAC309 | SYBR Green | | 498 | 522 | SigmaAldrich | 217087-73-5 |
| ISAC310 | SYTO 11 | | 506 | 526 | LifeTechnologies | 173080-67-6 |
| ISAC311 | SYTO 13 | | 488 | 506 | LifeTechnologies | 173080-69-8 |
| ISAC312 | SYTO 16 | | 488 | 520 | LifeTechnologies | 173080-72-3 |
| ISAC313 | SYTO 17 | | 618 | 637 | LifeTechnologies | 189233-66-7 |
| ISAC314 | SYTO 45 | | 450 | 486 | LifeTechnologies | 335078-86-9 |
| ISAC315 | SYTO 59 | | 622 | 643 | LifeTechnologies | 235422-34-1 |
| ISAC316 | SYTO 60 | | 650 | 681 | LifeTechnologies | 335079-14-6 |
| ISAC317 | SYTO 61 | | 618 | 651 | LifeTechnologies | 335079-15-7 |
| ISAC318 | SYTO 62 | | 650 | 681 | LifeTechnologies | 286951-08-4 |
| ISAC319 | SYTO 82 | | 540 | 560 | LifeTechnologies | 335079-10-2 |
| ISAC320 | SYTO 9 | | 482 | 500 | LifeTechnologies | 208540-89-0 |
| ISAC321 | SYTOX AADvanced | | 546 | 646 | LifeTechnologies | No names found |
| ISAC322 | SYTOX Blue | | 431 | 480 | LifeTechnologies | 396077-00-2 |
| ISAC323 | SYTOX Green | | 504 | 523 | LifeTechnologies | 194100-76-0 |
| ISAC324 | SYTOX Orange | | 547 | 570 | LifeTechnologies | 324767-53-5 |

TABLE 2-continued

| ID | NAME | Alternate Names | Excitation | Emission | Vendor/Source | ACS CAS# |
|---|---|---|---|---|---|---|
| ISAC325 | SYTOX Red | | 640 | 658 | LifeTechnologies | 915152-67-9 |
| ISAC326 | tdTomato | | 554 | 581 | Clontech | 1114838-94-6 |
| ISAC334 | Tetramethylrhodamine | TMRho | 553 | 581 | LifeTechnologies | 70281-37-7 |
| ISAC329 | Texas Red | Texas Red ®-X, succinimidyl ester; C41H44N4O10S2 | 589 | 615 | LifeTechnologies | 82354-19-6 |
| ISAC330 | Texas Red-X, succinimidyl ester | | 589 | 615 | LifeTechnologies | 216972-99-5 |
| ISAC331 | Thiazole Orange | | 500 | 530 | SigmaAldrich | 107091-89-4 |
| ISAC332 | ThiolTracker Violet | | 406 | 526 | LifeTechnologies | No names found |
| ISAC335 | TO-PRO-1 | TO-PRO ®-1 iodide (515/531); C24H29I2N3S; Quinolinium, 4-[(3-methyl-2(3H)-benzothiazolylidene)methyl]-1-[3-(trimethylammonio)propyl]-, diiodide/; | 509 | 533 | LifeTechnologies | 157199-59-2 |
| ISAC338 | TO-PRO-3 | TO-PRO ®-3 iodide (642/661); C26H31I2N3S; Quinolinium, 4-[3-(3-methyl-2(3H)-benzothiazolylidene)-1-propenyl]-1-[3-(trimethylammonio)propyl]-, diiodide/ | 642 | 661 | LifeTechnologies | 157199-63-8 |
| ISAC341 | TOTO-1 | TOTO ®-1 iodide (514/533); C49H58I4N6S2; Quinolinium, 1-1'-[1,3-propanediylbis[(dimethyliminio)-3,1-propanediyl]]bis[4-[(3-methyl-2(3H)-benzothiazolylidene)methyl]]-, tetraiodide/ | 509 | 533 | LifeTechnologies | 143413-84-7 |
| ISAC344 | TOTO-3 | TOTO ®-3 iodide (642/660); C53H62I4N6S2 | 642 | 661 | LifeTechnologies | 166196-17-4 |
| ISAC346 | Tricolor | | 563 | 670 | LifeTechnologies | 478184-50-8 |
| ISAC347 | TRITC | Tetramethylrhodamine; tetramethylrhodamine-5-(and-6)-isothiocyanate; C25H21N3O3S; Xanthylium, 9-(2-carboxyisothiocyanatophenyl)-3,6-bis(dimethylamino)-, inner salt/ | 547 | 572 | LifeTechnologies | 745735-42-6 |
| ISAC351 | TruRed | | 490 | 695 | Not Commercialized | 396076-95-2 |
| ISAC352 | V19 | | 397 | 572 | Not Commercialized | No names found |
| ISAC353 | V450 | | 405 | 448 | BDBioscences | 1257844-82-8 |
| ISAC354 | V500 | | 415 | 500 | BDBioscences | 1333160-12-5 |
| ISAC355 | VioBlue | | 400 | 452 | Miltenyl Biotech | 1431147-59-9 |
| ISAC356 | VioGreen | | 388 | 520 | Miltenyl Biotech | No names found |
| ISAC357 | Vybrant DyeCycle Green | | 505 | 535 | LifeTechnologies | 1431152-50-9 |
| ISAC358 | Vybrant DyeCycle Orange | | 518 | 563 | LifeTechnologies | 1055990-89-0 |
| ISAC359 | Vybrant DyeCycle Ruby | | 637 | 686 | LifeTechnologies | 1345202-72-3 |
| ISAC360 | Vybrant DyeCycle Violet | | 370 | 436 | LifeTechnologies | 1015439-88-9 |
| ISAC361 | YFP | Yellow Fluorescent Protein | 505 | 530 | Clontech | No names found |
| ISAC363 | YO-PRO-1 | YO-PRO ®-1 iodide (491/509); C24H29I2N3O | 491 | 506 | LifeTechnologies | 152068-09-2 |
| ISAC365 | YO-PRO-3 | YO-PRO ®-3 iodide (612/631); C26H31I2N3O; Quinolinium, 4-[3-(3-methyl-2(3H)-benzoxazolylidene)-1-propenyl]-1-[3-(trimethylammonio)propyl]-, diiodide/ | 613 | 629 | LifeTechnologies | 157199-62-7 |
| ISAC368 | YOYO-1 | YOYO ®-1 iodide (491/509); C49H58I4N6O2; | 491 | 509 | LifeTechnologies | 143413-85-8 |
| ISAC370 | YOYO-3 | YOYO ®-3 iodide (612/631); C53H62I4N6O2; Quinolinium, 1,1'-[1,3-propanediylbis[(dimethyliminio)-3,1-propanediyl]]bis[4-[3-(3-methyl-2(3H)-benzoxazolylidene)-1-propenyl]]-, tetraiodide/; | 613 | 629 | LifeTechnologies | 156312-20-8 |
| ISAC373 | ZsGreen | | 494 | 517 | Clontech | 1216871-88-3 |

Commercially available beads including, but not limited to, those sold by Bangs Laboratories, Inc, Sperhotech Inc., Thermo Scientific, Inc. and equivalent suppliers) can be used in combination with the hydrogel particles described herein. Depending on the assay, it is within the ordinary skill in the art to select a bead with the proper bead diameter, fluorescent emission and/or excitation spectrum and/or fluorescent intensity. For example, a quality control bead used in conjunction with a blue, red or UV laser can be embedded into one or more hydrogel particles provided herein. For example, an Alignflow™ flow cytometry alignment bead for blue lasers (catalog no. A-16500 (2.5 µm), A-16503 (6.0 µm)), red lasers (catalog no. A-16501 (2.5 µm), A-16504 (6.0 µm)) or UV lasers (catalog no. A-16502 (2.5 µm), A-16505 (6.0 µm)) can be embedded in on or more of the hydrogel particles provided herein.

In one embodiment, a fluorescent bead that can be excited at any wavelength from 365 nm-650 nm is embedded in a hydrogel particle. In one embodiment, the bead is a "rainbow particle" that contains a mixture of fluorophores, for example 4 fluorophores, 5 fluorophores, 6 fluorophores, seven fluorophores or eight fluorophores. In this regard, the user selects which wavelength to excite the particle, depending on the fluorophore being interrogated. Rainbow particles are commercially available, for example, from BD Biosciences (catalog nos. 556298 (mid range FL1 fluorescence), 556286 (6 color, 3.0-3.4 µm), 556288 (6 color, 6.0-6.4 µm), 559123 (8 color)) and Spherotech in various diameters (e.g., catalog nos. RCP20-5 (4 color), RCP-30-5 (6 peaks), RCP-30-5A (8 peaks)

A cell sorting set-up bead can be embedded in one or more of the hydrogel particles provided herein. In one embodiment, a cell sorting set-up beads approximates the size, emission wavelength, and intensity of a biological sample, and can be used to calibrate a flow cytometer's cell sorting system, including laser source, optics, and stream flow. In one embodiment, a cell sorting set-up beads is embedded in one or more hydrogel particles and is amenable for use with a UV, blue, green/yellow or red laser. Where a green laser is used, in one embodiment, the embedded bead is excited at 570 nm with emission of 575 nm, but may also be exited at 488 nm. Commercially available cell sorting set-up beads are available, for example, from Life Technologies (catalog nos. C-16506 (UV laser), C-16508 (blue laser), C-16509 (green-yellow laser), C-16507 (red laser)).

A compensation control bead can also be embedded in one or more of the hydrogel particles provided herein. Accurate compensation is an important parameter for effective multicolor analysis in flow cytometry. However, cellular-based compensation controls are not completely effective as many antigens are not highly expressed, and dimly stained cells can lead to inaccurate compensation settings.

A compensation control bead, in one embodiment, includes a fluorescent antibody conjugate capture capacity (positive compensation bead) or is inert (negative compensation bead). The compensation bead is mixed with a fluorophore-conjugated human, mouse, rat, hamster, or rabbit antibody; the two components provide a distinct high-signal positive control with an appropriate negative population that can then be used to set compensation properly regardless of the intensity of the cells in the actual experiment. Once the antibody is mixed with the bead, it is embedded in one or more of the hydrogel particles provided herein. Commercially available compensation beads are available, for example, from Life Technologies (catalog nos. A-10344, A-10389, A10497, A10513) and Spherotech (catalog nos. CMIg-P-08-2K, CMIg-P-30-2K, CMIg-P-50-3K, CMIg-P-70-3K).

In one embodiment, a hydrogel particle with an embedded/encapsulated bead is used as a reference for a cellular assay, for example, a phagocytosis assay cytoxicity assay, motility assay, viability assay, etc. Phagocytosis is the process by which a cell engulfs a solid particle to form an internal vesicle known as a phagosome. In this regard, a hydrogel particle can be tuned to have one or more optical properties substantially similar to a phagocyte, before and after the phagocyte engulfs a particle. Accordingly, in one embodiment, the hydrogel particles provided herein are used as control particles for a phagocytosis assay. In a further embodiment, (i) one or more of the optical properties of a hydrogel particle is substantially similar to a phagocyte prior to particle uptake and (ii) one or more of the optical properties of a second hydrogel particle is substantially similar to a phagocyte after to particle uptake. In this regard, a control is generated for measuring particle uptake by a phagocyte.

In one embodiment, the phagocyte is a professional phagocyte. In another embodiment, the phagocyte is a non-professional phagocyte (i.e., a cell that consumes dying cells and foreign organisms). In a further embodiment, the non-professional phagocyte is an epithelial cell, endothelial cell, fibroblast or mesenchymal cell. Hydrogel particles in one embodiment, are tuned to have one or more optical properties substantially similar to a professional phagocyte set forth in Table 3 below (prior to and/or after particle uptake).

TABLE 3

| Location | Phagocyte type |
|---|---|
| Blood | Neutrophil, monocyte |
| Bone marrow | Macrophage, monocyte, sinusoidal cell, lining cell |
| Bone tissue | Osteoclast |
| Gut and intestinal Peyer's patches | Macrophage |
| Connective tissue | Histiocyte, macrophage, monocyte, dendritic cell |
| Liver | Kupffer cell, monocyte |
| Lung | Self-replicating macrophage, monocyte, mast cell, dendritic cell |
| Lymphoid tissue | Free and fixed macrophages and monocytes, dendritic cell |
| Nervous tissue | Microglial cell (CD4+) |
| Spleen | Free and fixed macrophages, monocytes, sinusoidal cell |
| Thymus | Free and fixed macrophages, monocytes |
| Skin | Resident Langerhans cells, dendritic cells, conventional macrophage, mast cell |

In one embodiment, a plurality of hydrogel particles of the invention, embedded with a substance such as nucleic acid or a bead is used as control reagents for a genomic cytometry assay. In this regard, a specific number of copies of a particular chromosome, RNA sequence and/or DNA sequence can be mimicked by the embedded substance. The hydrogel particle can then be used as a control for a sample being probed for genetic information, such as the number of copies of a chromosome, the number of copies of an RNA sequence and/or the number of copies of an RNA sequence.

The three primary modes of deconvolution for flow cytometry are the two passive optical properties of a particle (forward scattering, FSC, corresponding to the refractive index, or RI; and side scattering, SSC) and biomarkers present on the surface of a given cell type. Therefore, compositions that allow hydrogel particles of the disclosure to mimic specific cell types with respect to these three modes are useful for providing synthetic, robust calibrants for flow cytometry.

In one embodiment, the refractive index (RI) of a disclosed hydrogel particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In another embodiment, the refractive index (RI) of a disclosed hydrogel particle is about 1.10 to about 3.0, or about 1.15 to about 3.0, or about 1.20 to about 3.0, or about 1.25 to about 3.0, or about 1.30 to about 3.0, or about 1.35 to about 3.0, or about 1.4 to about 3.0, or about 1.45 to about 3.0, or about 1.50 to about 3.0, or about 1.6 to about 3.0, or about 1.7 to about 3.0, or about 1.8 to about 3.0, or about 1.9 to about 3.0, or about 2.0 to about 3.0.

In some embodiments, the refractive index (RI) of a disclosed hydrogel particle is less than about 1.10, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

The SSC of a disclosed hydrogel particle is most meaningfully measured in comparison to that of target cell. In some embodiments, a disclosed hydrogel particle has an SSC within 30%, within 25%, within 20%, within 15%, within 10%, within 5%, or within 1% that of a target cell, as measured by a cytometric device.

The SSC of a hydrogel particle in one embodiment, is modulated by incorporating a high-refractive index molecule (or plurality thereof) in the hydrogel. In one embodiment, a high-refractive index molecule is provided in a hydrogel particle, and in a further embodiment, the high-refractive index molecule is colloidal silica, alkyl acrylate, alkyl methacrylate or a combination thereof. Thus in some embodiments, a hydrogel particle of the disclosure comprises alkyl acrylate and/or alkyl methacrylate. Concentration of monomer in one embodiment is adjusted to further adjust the refractive index of the hydrogel particle.

Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tertbutyl, 2-ethylhexyl, heptyl or octyl groups. The alkyl group may be branched or linear.

High-refractive index molecules can also include vinylarenes such as styrene and methylstyrene, optionally substituted on the aromatic ring with an alkyl group, such as methyl, ethyl or tert-butyl, or with a halogen, such as chlorostyrene.

In some embodiments, FSC is modulated by adjusting the percentage of monomer present in the composition thereby altering the water content present during hydrogel formation. In one embodiment, where a monomer and co-monomer are employed, the ratio of monomer and co-monomer is adjusted to change the hydrogel particle's forward scatter properties. This is shown in both FIG. 11 and FIG. 12.

The FSC of a disclosed hydrogel particle is most meaningfully measured in comparison to that of target cell. In some embodiments, a disclosed hydrogel particle has an FSC within 30%, within 25%, within 20%, within 15%, within 10%, within 5%, or within 1% that of a target cell, as measured by a cytometric device.

FSC is related to particle volume, and thus can be modulated by altering particle diameter, as described herein. Generally, it has been observed that large objects refract more light than smaller objects leading to high forward scatter signals (and vice versa). Accordingly, particle diameter in one embodiment is altered to modulate FSC properties of a hydrogel particle. For example, hydrogel particle diameter is increased in one embodiment is altered by harnessing larger microfluidic channels during particle formation.

SSC can be engineered by encapsulating nanoparticles within hydrogels to mimic organelles in a target cell. In some embodiments, a hydrogel particle of the disclosure comprises one or more types of nanoparticles selected from the group consisting of: polymethyl methacrylate (PMMA) nanoparticles, polystyrene (PS) nanoparticles, and silica nanoparticles. See also FIGS. 11 and 12 which show that addition of various concentrations of nanoparticles allow for the adjustment of side scatter of a particle. Without wishing to be bound by theory, the ability to selectively tune both forward and side scatter of a hydrogel, as described herein, allows for a robust platform to mimic a vast array of cell types.

Although the invention is mainly described with respect to the modification of optical properties, the invention is not limited thereto. For example, hydrogel particles can be fabricated and adjusted to tune the capacitance of the particles, e.g., to calibrate coulter counters. In one embodiment, a hydrogel particle's capacitance is adjusted by altering the amount of hydrogel monomer in the composition. For example, polyanaline, polyacetylene; polyphenylene vinylene; polypyrrole (X=NH) and polythiophene (X=S) co-monomers; and polyaniline (X=NH/N) and polyphenylene sulfide (X=S) co-monomer concentrations can all be adjusted to alter capacitance. In one embodiment, the concentration of one or more of these monomers is increased to increase the capacitance of the hydrogel particle.

In some embodiments, a hydrogel particle of the disclosure has material modulus properties (e.g., elasticity) more closely resembling that of a target cell as compared to a polystyrene bead of the same diameter.

After the hydrogel particle is formed, one or more of the particle's surfaces can be functionalized, for example, to mimic one or more optical properties of a target cell or a labeled target cell. The functionalized hydrogel particle can also include an embedded bead or substance such as a biomolecule, as described above. In one embodiment, one or more hydrogel particles are functionalized with one or more fluorescent dyes, one or more cell surface markers (or epitope binding regions thereof), or a combination thereof. In one embodiment, the hydrogel particle is formed by polymerizing at least one bifunctional monomer and after formation, the hydrogel particle includes one or more functional groups that can be used for further attachment of a cell surface marker, an epitope binding region of a cell surface marker, a fluorescent dye, or combination thereof. The free functional group, in one embodiment, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

A hydrogel particle can be functionalized with any fluorescent dye known in the art, including fluorescent dyes listed in The MolecularProbes® Handbook-A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the hydrogel, as discussed above.

Non-limiting examples of known fluorescent dyes that can be used to functionalize the surface of a hydrogel particle described herein include: 6-carboxy-4',5'-dichloro-2',7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether,-alanine-carboxamide, or succinimidyl ester; 5-carboxyfluoresceinsuccinimidyl ester; 6-carboxyfluorescein succinimidyl ester; 5-(and-6)-carboxyfluorescein succinimidyl ester; 5-(4,6-dichlorotriazinyl) amino fluorescein; 2 ', 7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein, 5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester; 6-carboxyrhodamine 6G succinimidyl ester; 5-(and-6)-carboxyrhodamine6G succinimidyl ester; 5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester; 5-(and -6)-carboxytetramethylrhodamine succinimidyl ester; 6-carboxy-X-rhodamine; 5-carboxy-X-rhodamine succinimidyl ester; 6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester; 6-(tetramethylrhodamine-5-(and-6)-carboxamido) hexanoic acid; succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6) isothiocyanate.

Other examples of fluorescent dyes for use with the hydrogel particles described herein include, but are not limited to, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester; 6-dibromo-4, 4-difluoro-5,7-dimethyl-4-bora-3a, 4a-diaza-s-indacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester; 4,4-difluoro-5,7-dimefhyl-4-bora-3a,4a-diaza-s-indacene-3propionicacid; 4,4-difluoro-5,7-dimethyl-4-bora-3a,4adiaza-s-indacene-3-propionicacid succinimidyl ester; 4,4difluoro-5,7-dimefhyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino) hexanoic acid; 6-((4,4-difluoro-5, 7 dimethyl-4-bora-3a,4a-diaza-s-indacene-3-propionyl) amino) hexanoic acid or succinimidyl ester; N-(4, 4-difluoro 5,7-dimethyl-4-bora-3a,4a-diaza-s-indacene-3-propionyl) cysteic acid, succinimidyl ester or triethylammonium salt; 6-4,4-difluoro-1,3-dimethyl-5-(4-methoxyphenyl)-4-bora3a, 4a4,4-difluoro-5,7-diphenyl-4-bora-3a,4a-diazasindacene-3-propionicacid; 4,4-difluoro-5, 7-diphenyl-4-bora3a, 4a-diaza-s-indacene-3-propionic acid succinimidyl ester; 4,4-difluoro-5-phenyl-4-bora-3a,4a-diaza-s-indacene-3-propionic acid; succinimidyl ester; 6-((4,4-difluoro-5-phenyl-4 bora-3a,4a-diaza-s-indacene-3-propionyl)amino) hexanoicacid or succinimidyl ester; 4,4-difluoro-5-(4-phenyl-1,3butadienyl)-4-bora-3a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)aminohexanoicacid or succinimidyl ester; 4,4-difluoro-5-styryl-4-bora-3a, 4a-diaza-s-indacene-3-propionic acid; 4,4-difluoro-5-styryl-4-bora-3a, 4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionicacid succinimidyl ester; 4,4-difluoro-5-(2-thienyl)-4-bora-3a,4a-diaza-sindacene-3-propionicacid succinimidyl ester; 6-(((4-(4,4-difluoro-5-(2-thienyl)-4-bora-3a,4adiazas-indacene-3-yl)phenoxy)acetyl)amino)hexanoic acid or succinimidyl ester; and 6-(((4,4-difluoro-5-(2-thienyl)-4-bora-3a,4a-diaza-s-indacene-3-yl) styryloxy)acetyl) aminohexanoic acid or succinimidyl ester.

Fluorescent dyes for derivatization of the surface of one or more hydrogel particles in one embodiment, include, but are not limited to, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In another embodiment, fluorescent dyes for use with the hydrogel particles and methods described herein include cyanine dyes commercially available from Amersham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired spectral excitation and emission properties of the hydrogel particle.

Hydrogel particles, in one embodiment, are functionalized with one or more cell surface markers (see, e.g., Tables 4 and 7-8), or fragments thereof, for example, extracellular portions thereof in the case of transmembrane proteins, for example, by attaching the one or more cell surface markers, extracellular portions or ligand binding regions thereof to the particle via a free amine, free carboxyl and/or free hydroxyl group present on the surface of the hydrogel particle. Functionalization of a hydrogel particle with a dye or cell surface molecule can also occur through a linker, for example a streptavidin/biotin conjugate.

Depending on the target cell, individual hydrogel particles can be derivatized with one or more cell surface markers, or fragments thereof, for example, extracellular portions thereof in the case of transmembrane proteins to further mimic the structural properties of the target cell. Tables 4 and 7-8, provided below, sets forth a non-limiting list of cell surface markers that can be used to derivative hydrogel particles, depending on the target cell. Although the cell surface marker is provided, it is understood that a portion of the cell surface marker, for example, a receptor binding portion, a ligand binding portion, or an extracellular portion of the marker can be used to derivative the hydrogel particle (at the free functional group, as described above). See also FIGS. 11 and 12 which show that hydrogel surface modification with for example, a cell surface receptor, together with the selective tuning of FSC and/or SSC, allows for the fabrication of a hydrogel particle with the desired feature(s).

TABLE 4

| Target Cell | Cell Surface Marker(s) (human) | Cell Surface Marker(s) (mouse) |
|---|---|---|
| B Cell | CD19, CD20 | CD19, CD22 (B cell activation marker), CD45R/B220 |
| T Cell | CD3, CD4, CD8 | CD3, CD4, CD8 |
| Activated T Cells | CD25, CD69 | CD25, CD69 |
| Dendritic Cell | CD1c, CD83, CD123, CD141, CD209, MHC II | CD11c, CD123, MHC II |
| Plasmacytoid Dendritic Cells* | CD123, CD303, CD304 | CD11c$^{int}$, CD317 |
| Platelet (resting) | CD42b | CD41 |
| Platelet (activated) | CD62P | CD62P |
| Natural Killer Cells | CD16, CD56 | CD49b (clone DX5) |
| Hematopoietic Stem Cell | CD34, CD90 | CD48, CD117, CD150, Sca-1 |
| Macrophage | CD11b, CD68, CD163 | F4/80, CD68 |
| Monocyte | CD14, CD16, CD64 | CD11b, CD115, Ly-6C |
| Plasma Cell | CD138 | CD138 |
| Red Blood Cell | CD235a | TER-119 |
| Neutrophil | CD15, CD16 | CD11b, Ly-6B.2, Ly6G, Gr-1 |
| Basophil | 2D7 antigen, CD123, CD203c, FcεRIα | CD200R3, FcεRIα |
| Eosinophil | CD11b, CD193, EMR1, Siglec-8 | CD11b, CD193, F4/80, Siglec-F |
| Granulocyte | CD66b | CD66b, Gr-1/Ly6G, Ly6C |
| Endothelial cell | CD146 | CD146 MECA-32, CD106, CD31, CD62E (activated endothelial cell) |
| Epithelial cell | CD326 | CD326 (EPCAM1) |
| Natural Killer (NK) cell | CD56 | CD335 (NKp46) |
| Myeloid derived suppressor cell (MDSC) | CD11b, CD14, CD33 (Siglec-3) | CD11b, GR1 |

Cell types including but not limited to various cell lines such as CHO, HEK-293, BHK-21, NS0, MDCK, VERO, MRC-S, W1-38 and Sp2/0 Mouse Myeloma (hybridomas). Table 5 and Table 6 each provides other cell types for use with the hydrogel particles described herein.

TABLE 5 keratinocyte of epidermis
basal cell of epidermis
keratinocyte of fingernails and toenails
basal cell of nail bed
hair shaft cells
medullary hair shaft cells
cortical hair shaft cells
cuticular hair shaft cells
hair-root sheath cells
cuticular hair-root sheath cells
hair-root sheath cells of Huxley's layer
hair-root sheath cells of Henle's layer
external hair-root sheath cells
hair matrix cell (stem cell)
surface epithelial cell of stratified squamous epithelium of tongue
surface epithelial cell of stratified squamous epithelium of oral cavity
surface epithelial cell of stratified squamous epithelium of esophagus
surface epithelial cell of stratified squamous epithelium of anal canal
surface epithelial cell of stratified squamous epithelium of distal urethra
surface epithelial cell of stratified squamous epithelium of vagina
basal cell of these epithelia
cell of urinary epithelium
cells of salivary gland
Mucous cells of salivary gland
Serous cell of salivary gland
cell of von Ebner's gland in tongue
cell of mammary gland
cell of lacrimal gland
cell of ceruminous gland of ear
cell of eccrine sweat gland
cell of eccrine sweat gland
cell of apocrine sweat gland
cell of gland of Moll in eyelid
cell of sebaceous gland
cell of Bowman's gland in nose TABLE 5-continued cell of Brunner's gland in duodenum
cell of seminal vesicle
cell of prostate gland
cell of bulbourethral gland
cell of Bartholin's gland
cell of gland of Littre
cell of endometrium of uterus
isolated goblet cell of respiratory and digestive tracts
mucous cell of lining of stomach
zymogenic cell of gastric gland
oxyntic cell of gastric gland
acinar cell of pancreas
Paneth cell of small intestine
type II pneumocyte of lung
Clara cell of lung
cells of anterior pituitary
cell of intermediate pituitary
cells of posterior pituitary
cells of gut and respiratory tract
cells of thyroid gland
cells of parathyroid gland
cells of adrenal gland
steroid hormones
cells of gonads
cells of juxtaglomerular apparatus of kidney
juxtaglomerular cell
macula
densa cell
peripolar cell
mesangial cell
brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
hepatocyte
white fat cell
brown fat cell
lipocyte of liver TABLE 5-continued type I pneumocyte
pancreatic duct cell
parietal cell of kidney glomerulus
podocyte of kidney glomerulus
cell of thin segment of loop of Henle
collecting duct cell (in kidney)
duct cell of seminal vesicle
duct cell of prostate gland
vascular endothelial cells of blood vessels and lymphatics
fenestrated vascular endothelial cells
continuous vascular endothelial cells
splenic vascular endothelial cells
synovial cell
serosal cell
squamous cell lining perilymphatic space of ear
cells lining endolymphatic space of ear
squamous cell
columnar cells of endolymphatic sac
"dark" cell
vestibular membrane cell
stria vascularis basal cell
stria vascularis marginal cell
cell of Claudius
cell of Boettcher
choroid plexus cell
squamous cell of pia-arachnoid
cells of ciliary epithelium of eye
corneal "endothelial" cell
Ciliated Cells of respiratory tract
Ciliated Cells of oviduct and of endometrium of uterus
Ciliated Cells of rete testis and ductulus efferens
Ciliated Cells of central nervous system
epithelial
ameloblast
nonepithelial
chondrocytes
osteoblast/osteocyte
osteoprogenitor cell
hyalocyte of vitreous body of eye
stellate cell of perilymphatic space of ear
skeletal muscle cells
heart muscle cells
smooth muscle cells (various)
myoepithelial cells
red blood cell
megakaryocyte
macrophages and related cells
neutrophil
eosinophil
basophil
mast cell
T lymphocyte
B lymphocyte
photoreceptors (rods, cones, and can be blue sensitive, green sensitive, red sensitive)
inner hair cell of organ of Corti
outer hair cell of organ of Corti
type I hair cell of vestibular apparatus of ear
type II hair cell of vestibular apparatus of ear
type II taste bud cell
olfactory neuron
basal cell of olfactory epithelium
carotid body cell type I
carotid body cell type II
Merkel cell of epidermis
primary sensory neurons specialized for touch (various)
primary sensory neurons specialized for temperature - cold sensitive
primary sensory neurons specialized for temperature - heat sensitive
primary sensory neurons specialized for pain (various)
proprioceptive primary sensory neurons (various)
Autonomic Neurons
inner pillar cell
outer pillar cell
inner phalangeal cell
outer phalangeal cell
border cell
Hensen cell
supporting cell of vestibular apparatus
supporting cell of taste bud (type I taste bud cell)
supporting cell of olfactory epithelium
Schwann cell
satellite cell (encapsulating peripheral nerve cell bodies)
enteric glial cell
neurons
glial cells
anterior lens epithelial cell
lens fiber (crystallin-containing cell)
melanocyte
retinal pigmented epithelial cell
oogonium/oocyte
spermatocyte
spermatogonium (stem cell for spermatocyte)
ovarian follicle cell
Sertoli cell (in testis)
thymus epithelial cell
Salivary gland mucous cell
Salivary gland number 1
Von Ebner's gland cell in tongue
Mammary gland cell
Lacrimal gland cell
Ceruminous gland cell in ear
Eccrine sweat gland dark cell
Eccrine sweat gland clear cell
Apocrine sweat gland cell
Gland of Moll cell in eyelid
Sebaceous gland cell
Bowman's gland cell in nose
Brunner's gland cell in duodenum
Seminal vesicle cell
Prostate gland cell
Bulbourethral gland cell
Bartholin's gland cell
Gland of Littre cell
Uterus endometrium cell
goblet cell of respiratory and digestive tracts
Stomach lining mucous cell
Gastric gland zymogenic cell
Gastric gland oxyntic cell
Pancreatic acinar cell
Paneth cell of small intestine
pneumocyte of lung
Clara cell of lung
anterior pituitary cells
Somatotropes
Lactotropes
Thyrotropes
Gonadotropes
Corticotropes
melanocyte-stimulating hormone
Magnocellular neurosecretory cells secreting:
Gut and respiratory tract cells secreteing:
Thyroid gland cells
thyroid epithelial cell
parafollicular cell
Parathyroid gland cells
Parathyroid chief cell
Oxyphil cell
Adrenal gland cells
chromaffin cells
secreting steroid hormones (mineralcorticoids and gluco corticoids)
Leydig cell of testes secreting testosterone
Theca interna cell of ovarian follicle secreting estrogen
Corpus luteum cell of ruptured ovarian follicle secreting progesterone
Granulosa lutein cells
Theca lutein cells
Juxtaglomerular cell (renin secretion)
Macula densa cell of kidney
Peripolar cell of kidney
Mesangial cell of kidney
epidermal keratinocyte
Epidermal basal cell
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell TABLE 5-continued Hair matrix cell (stem cell)
epithelial cell of stratified squamous epithelium of cornea,
epithelial cell of stratified squamous epithelium of tongue
epithelial cell of stratified squamous epithelium of oral cavity
epithelial cell of stratified squamous epithelium of esophagus
epithelial cell of stratified squamous epithelium of anal canal
epithelial cell of stratified squamous epithelium of distalurethra
epithelial cell of stratified squamous epithelium of vagina
basal cell (stem cell) of epithelia of cornea
basal cell (stem cell) of epithelia of tongue
basal cell (stem cell) of epithelia of oral cavity
basal cell (stem cell) of epithelia of esophagus
basal cell (stem cell) of epithelia of anal canal
basal cell (stem cell) of epithelia of distal urethra
basal cell (stem cell) of epithelia of vagina
Urinary epithelium cell
Auditory inner hair cell of organ of Corti
Auditory outer hair cell of organ of Corti
basal cell of olfactory epithelium
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor cells of retina in eye:
Photoreceptor rod cells
Photoreceptor blue-sensitive cone cell of eye
Photoreceptor green-sensitive cone cell of eye
Photoreceptor red-sensitive cone cell of eye
Proprioceptive primary sensory neurons
Touch-sensitive primary sensory neurons
Type I carotid body cell
Type II carotid body cell
Type I hair cell of vestibular system of ear
Type II hair cell of vestibular system of ear
Type I taste bud cell
Cholinergic neural cell
Adrenergic neural cell
Peptidergic neural cell
Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Taste bud supporting cell
Olfactory epithelium supporting cell
Schwann cell
Satellite glial cell
Enteric glial cell
Astrocyte
Neuron cells
Oligodendrocyte
Spindle neuron
Anterior lens epithelial cell
Crystallin-containing lens fiber cell
Hepatocyte
Adipocytes (white fat cell, brown fat cell, liver lipocyte)
Kidney parietal cell
Kidney glomerulus podocyte
Kidney proximal tubule brush border cell
Loop of Henle thin segment cell
Kidney distal tubule cell
Kidney collecting duct cell
Type I pneumocyte
Pancreatic duct cell
Nonstriated duct cell
principal cell
Intercalated cell
Duct cell
Intestinal brush border cell
Exocrine gland striated duct cell
Gall bladder epithelial cell
Ductulus efferens nonciliated cell
Epididymal principal cell
Epididymal basal cell
Ameloblast epithelial cell
Planum semilunatum epithelial cell of vestibular system of ear
Organ of Corti interdental epithelial cell TABLE 5-continued Loose connective tissue fibroblasts
Corneal fibroblasts (corneal keratocytes)
Tendon fibroblasts
Bone marrow reticular tissue fibroblasts
nonepithelial fibroblasts
Pericyte
Nucleus pulposus cell of intervertebral disc
Cementoblast/cementocyte
Odontoblast/odontocyte
Hyaline cartilage chondrocyte
Fibrocartilage chondrocyte
Elastic cartilage chondrocyte
Osteoblast/osteocyte
Osteoprogenitor cell
Hyalocyte of vitreous body of eye
Stellate cell of perilymphatic space of ear
Hepatic stellate cell (Ito cell)
Pancreatic stelle cell
skeletal muscle Cell
Red skeletal muscle cell (slow)
White skeletal muscle cell (fast)
Intermediate skeletal muscle cell
nuclear bag cell of muscle spindle
nuclear chain cell of muscle spindle
Satellite cell (stem cell)
Heart muscle cells
Ordinary heart muscle cell
Nodal heart muscle cell
Purkinje fiber cell
Smooth muscle cell
Myoepithelial cell of iris
Myoepithelial cell of exocrine glands
Erythrocyte
Megakaryocyte
Monocyte
Connective tissue macrophage
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Hybridoma cell
Mast cell
Helper T cell
Suppressor T cell
Cytotoxic T cell
Natural Killer T cell
B cell
Natural killer cell
Reticulocyte
Stem cells and committed progenitors for the blood and immune system (various types)
Oogonium/Oocyte
Spermatid
Spermatocyte
Spermatogonium cell
Spermatozoon
Ovarian follicle cell
Sertoli cell (in testis)
Thymus epithelial cell
Interstitial kidney cells

TABLE 6

Keratinizing Epithelial Cells keratinocyte of epidermis (=differentiating epidermal cell)
basal cell of epidermis (stem cell)
keratinocyte of fingernails and toenails
basal cell of nail bed (stem cell)
hair shaft cells
medullary
cortical
cuticular
hair-root sheath cells

TABLE 6-continued

Cuticular root sheath cells
root sheath cells of Huxley's layer
root sheath cells of Henle's layer
external root sheath cells
hair matrix cell (stem cell)

Cells of Wet Stratified Barrier Epithelia surface epithelial cell of stratified squamous epithelium of cornea, tongue, oral
cavity, esophagus, anal canal, distal urethra, vagina
basal cell of these epithelia (stem cell)
cell of urinary epithelium (lining bladder and urinary ducts)

Epithelial Cells Specialized for Exocrine Secretion cells of salivary gland
    mucous cell (secretion rich in polysaccharide)
    serous cell (secretion rich in glycoprotein enzymes)
cell of von Ebner's gland in tongue (secretion to wash over taste buds)
cell of mammary gland, secreting milk
cell of lacrimal gland, secreting tears
cell of ceruminous gland of ear, secreting wax
cell of eccrine sweat gland, secreting glycoproteins (dark cell)
cell of eccrine sweat gland, secreting small molecules (clear cell)
cell of apocrine sweat gland (odoriferous secretion, sex-hormone sensitive)
cell of gland of Moll in eyelid (specialized sweat gland)
cell of sebaceous gland, secreting lipid-rich sebum
cell of Bowman's gland in nose (secretion to wash over olfactory epithelium)
cell of Brunner's gland in duodenum, secreting alkaline solution of mucus and enzymes
cell of seminal vesicle, secreting components of seminal fluid, including fructose (as fuel for swimming sperm)
cell of prostate gland, secreting other components of seminal fluid
cell of bulbourethral gland, secreting mucus
cell of Bartholin's gland, secreting vaginal lubricant
cell of gland of Littre, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung (function unknown)

Cells Specialized for Secretion of Hormones cells of anterior pituitary, secreting growth hormone, follicle-stimulating hormone, luteinizing hormone, prolactin, adrenocorticotropic hormone, and/or thyroid-stimulating hormone
cell of intermediate pituitary, secreting melanocyte-stimulating hormone
cells of posterior pitutiary, secreting oxytocin and/or vasopressin
cells of gut and respiratory tract, secreting serotonin, endorphin, somatostatin, gastrin, secretin, cholecystokinin, insulin, glucagon, and/or bombesin
cells of thyroid gland, secreting
    thyroid hormone
    calcitonin
cells of parathyroid gland, secreting
    parathyroid hormone
    oxyphil cell (function unknown)
cells of adrenal gland, secreting
    epinephrine
    norepinephrine
steroid hormones
    mineralocorticoids
    glucocorticoids
cells of gonads, secreting
    testosterone (Leydig cell of testis)
    estrogen (theca interna cell of ovarian follicle)
    progesterone (corpus luteum cell of ruptured ovarian follicle)
cells of juxtaglomerular apparatus of kidney
juxtaglomerular cell (secreting renin)
macula densa cell   (uncertain but probably related in
peripolar cell   { function; possibly involved in secretion
mesangial cell   of erythropoietin)

Epithelial Absorptive Cells in Gut, Exocrine Glands, and Urogenital Tract brush border cell of intestine (with microvilli)
striated duct cell of exocrine glands
gall bladder epithelial cell
brush border cell of proximal tubule of kidney
distal tubule cell of kidney
nonciliated cell of ductulus efferens
epididymal principal cell
epididymal basal cell

Cells Specialized for Metabolism and Storage hepatocyte (liver cell)
fat cells
    white fat
    brown fat
    lipocyte of liver

Epithelial Cells Serving Primarily a Barrier Function, Lining the Lung, Gut, Exocrine Glands, and Urogenital Tract type I pneumocyte (lining air space of lung)
pancreatic duct cell (centroacinar cell)
nonstriated duct cell of sweat gland, salivary gland, mammary gland, etc.
    (various)
parietal cell of kidney glomerulus
podocyte of kidney glomerulus
cell of thin segment of loop of Henle (in kidney)
collecting duct cell (in kidney)
duct cell of seminal vesicle, prostate gland, etc. (various)

Epithelial Cells Lining Closed Internal Body Cavities vascular endothelial cells of blood vessels and lymphatics
    fenestrated
    continuous
    splenic
synovial cell (lining joint cavities, secreting largely hyaluronic acid)
serosal cell (lining peritoneal, pleural, and pericardial cavities)
squamous cell lining perilymphatic space of ear
cells lining endolymphatic space of ear
    squamous cell
    columnar cells of endolymphatic sac
        with microvilli
        without microvilli
    "dark" cell
    vestibular membrane cell
    stria vascularis basal cell
    stria vascularis marginal cell
    cell of Claudius
    cell of Boettcher
choroid plexus cell (secreting cerebrospinal fluid)
squamous cell of pia-arachnoid
cells of ciliary epithelium of eye
    pigmented
    nonpigmented
corneal "endothelial" cell

Ciliated Cells with Propulsive Function

Ciliated Cells of respiratory tract
Ciliated Cells of oviduct and of endometrium of uterus (in female)
Ciliated Cells of rete testis and ductulus efferens (in male)
Ciliated Cells of central nervous system (ependymal cell lining brain cavities)

Cells Specialized for Secretion of Extracellular Matrix epithelial
    ameloblast (secreting enamel of tooth)
    planum semilunatum cell of vestibular apparatus of ear
        (secreting proteoglycan)
    interdental cell of organ of Corti (secreting tectorial
    "membrane" covering
    hair cells of organ of Corti)
nonepithelial (connective tissue)
    fibroblasts (various-of loose connective tissue, of cornea, of
        tendon, of reticular tissue of bone marrow,
        etc.)

TABLE 6-continued

```
              pericyte of blood capillary
              nucleus pulposus cell of intervertebral disc
              cementoblast/cementocyte (secreting bonelike cementum of
                  root of tooth)
              odontoblast/odontocyte (secreting dentin of tooth)
              chondrocytes
                      of hyaline cartilage
                      of fibrocartilage
                      of elastic cartilage
              osteoblast/osteocyte
              osteoprogenitor cell (stem cell of osteoblasts)
              hyalocyte of vitreous body of eye
              stellate cell of perilymphatic space of ear
                              Contractile Cells skeletal muscle cells
      red (slow)
      white (fast)
      intermediate
      muscle spindle-nuclear bag
      muscle spindle-nuclear chain
      satellite cell (stem cell)
heart muscle cells
      ordinary
      nodal
      Purkinje fiber
smooth muscle cells (various)
myoepithelial cells
      of iris
      of exocrine glands
                      Cells of Blood and Immune System red blood cell
megakaryocyte
macrophages and related cells
          monocyte
          connective-tissue macrophage (various)
          Langerhans cell (in epidermis)
          osteoclast (in bone)
          dendritic cell (in lymphoid tissues)
          microglial cell (in central nervous system)
neutrophil
eosinophil
basophil
mast cell
T lymphocyte
          helper T cell
          suppressor T cell
          killer T cell
B lymphocyte
          IgM
          IgG
          IgA
          IgE
killer cell
stem cells and committed progenitors for the blood and
          immune system (various)
                              Sensory Transducers photoreceptors
      rod
      cones
                      blue sensitive
                      green sensitive
                      red sensitive
hearing
          inner hair cell of organ of Corti
          outer hair cell of organ of Corti
acceleration and gravity
          type I hair cell of vestibular apparatus of ear
          type II hair cell of vestibular apparatus of ear
taste
          type II taste bud cell
smell
          olfactory neuron
basal cell of olfactory epithelium (stem cell for olfactory neurons)
blood pH
          carotid body cell
                      type I
                      type II touch
          Merkel cell of epidermis
          primary sensory neurons specialized for touch (various)
temperature
          primary sensory neurons specialized for temperature
                      cold sensitive
                      heat sensitive
pain
          primary sensory neurons specialized for pain (various)
configurations and forces in musculoskeletal system
          proprioceptive primary sensory neurons (various)
                              Autonomic Neurons cholinergic (various)
adrenergic (various)
peptidergic (various)
              Supporting Cells of Sense Organs and of Peripheral Neurons supporting cells of organ of Corti
inner pillar cell
          outer pillar cell
          inner phalangeal cell
          outer phalangeal cell
          border cell
          Hensen cell
supporting cell of vestibular apparatus
supporting cell of taste bud (type I taste bud cell)
supporting cell of olfactory epithelium
Schwann cell
satellite cell (encapsulating peripheral nerve cell bodies)
enteric glial cell
                  Neurons and Glial Cells of Central Nervous System neurons (huge variety of types-still poorly classified)
glial cells
          astrocyte (various)
          oligodendrocyte
                              Lens Cells anterior lens epithelial cell
lens fiber (crystallin-containing cell)
                              Pigment Cells melanocyte
retinal pigmented epithelial cell
                              Germ Cells oogonium/oocyte
spermatocyte
spermatogonium (stem cell for spermatocyte)
                              Nurse Cells ovarian follicle cell
Sertoli cell (in testis)
thymus epithelial cell
                      Exocrine secretory epithelial cells Salivary gland mucous cell (polysaccharide-rich secretion)
Salivary gland number 1 (glycoprotein enzyme-rich secretion)
Von Ebner's gland cell in tongue (washes taste buds)
Mammary gland cell (milk secretion)
Lacrimal gland cell (tear secretion)
Ceruminous gland cell in ear (earwax secretion)
Eccrine sweat gland dark cell (glycoprotein secretion)
Eccrine sweat gland clear cell (small molecule secretion)
Apocrine sweat gland cell (odoriferous secretion, sex-hormone
sensitive)
Gland of Moll cell in eyelid (specialized sweat gland)
Sebaceous gland cell (lipid-rich sebum secretion)
Bowman's gland cell in nose (washes olfactory epithelium)
Brunner's gland cell in duodenum (enzymes and alkaline
mucus)
Seminal vesicle cell (secretes seminal fluid components,
including fructose for swimming sperm)
Prostate gland cell (secretes seminal fluid components)
Bulbourethral gland cell (mucus secretion)
Bartholin's gland cell (vaginal lubricant secretion)
Gland of Littre cell (mucus secretion)
Uterus endometrium cell (carbohydrate secretion)
Isolated goblet cell of respiratory and digestive tracts (mucus
```

TABLE 6-continued secretion)
Stomach lining mucous cell (mucus secretion)
Gastric gland zymogenic cell (pepsinogen secretion)
Gastric gland oxyntic cell (hydrochloric acid secretion)
Pancreatic acinar cell (bicarbonate and digestive enzyme
secretion)
Paneth cell of small intestine (lysozyme secretion)
Type II pneumocyte of lung (surfactant secretion)
Clara cell of lung Hormone secreting cells Anterior pituitary cells
    Somatotropes
    Lactotropes
    Thyrotropes
    Gonadotropes
    Corticotropes
Intermediate pituitary cell, secreting melanocyte-stimulating
hormone
Magnocellular neurosecretory cells
    secreting oxytocin
    secreting vasopressin
Gut and respiratory tract cells
    secreting serotonin
    secreting endorphin
    secreting somatostatin
    secreting gastrin
    secreting secretin
    secreting cholecystokinin
    secreting insulin
    secreting glucagon
    secreting bombesin
Thyroid gland cells
    thyroid epithelial cell
    parafollicular cell
Parathyroid gland cells
    Parathyroid chief cell
    Oxyphil cell
Adrenal gland cells
    chromaffin cells
    secreting steroid
        hormones (mineralcorticoids and gluco
        corticoids)
Leydig cell of testes secreting testosterone
Theca interna cell of ovarian follicle secreting estrogen
Corpus luteum cell of ruptured ovarian follicle
secreting progesterone
    Granulosa lutein cells
    Theca lutein cells
Juxtaglomerular cell (renin secretion)
Macula densa cell of kidney
Peripolar cell of kidney
Mesangial cell of kidney
Derived primarily from ectoderm
Integumentary system Keratinizing epithelial cells Epidermal keratinocyte (differentiating epidermal cell)
Epidermal basal cell (stem cell)
Keratinocyte of fingernails and toenails
Nail bed basal cell (stem cell)
Medullary hair shaft cell
Cortical hair shaft cell
Cuticular hair shaft cell
Cuticular hair root sheath cell
Hair root sheath cell of Huxley's layer
Hair root sheath cell of Henle's layer
External hair root sheath cell
Hair matrix cell (stem cell)

Wet stratified barrier epithelial cells

Surface epithelial cell of stratified squamous
epithelium of cornea, tongue, oral cavity, esophagus, anal
canal, distalurethra and vagina
basal cell (stem cell) of epithelia of cornea, tongue, oral cavity,
esophagus, anal canal, distal urethra and vagina
Urinary epithelium cell (lining urinary bladder and urinary
ducts)

TABLE 6-continued

Nervous system

There are nerve cells, also known as neurons, present in our human
body. They are branched out. These cells make upnervous tissue.
A neuron consists of a cell body with a nucleus and cytoplasm,
from which long thin hair-like parts arise.

Sensory transducer cells

Auditory inner hair cell of organ of Corti
Auditory outer hair cell of organ of Corti
Basal cell of olfactory epithelium (stem cell for olfactory
neurons)
Cold-sensitive primary sensory neurons
Heat-sensitive primary sensory neurons
Merkel cell of epidermis (touch sensor)
Olfactory receptor neuron
Pain-sensitive primary sensory neurons (various types)
Photoreceptor cells of retina in eye:
    Photoreceptor rod cells
    Photoreceptor blue-sensitive cone cell of eye
    Photoreceptor green-sensitive cone cell of eye
    Photoreceptor red-sensitive cone cell of eye
Proprioceptive primary sensory neurons (various types)
Touch-sensitive primary sensory neurons (various types)
Type I carotid body cell (blood pH sensor)
Type II carotid body cell (blood pH sensor)
Type I hair cell of vestibular system of ear (acceleration and
gravity)
Type II hair cell of vestibular system of ear (acceleration and
gravity)
Type I taste bud cell Autonomic neuron cells Cholinergic neural cell
Adrenergic neural cell
Peptidergic neural cell Sense organ and peripheral neuron supporting cells Inner pillar cell of organ of Corti
Outer pillar cell of organ of Corti
Inner phalangeal cell of organ of Corti
Outer phalangeal cell of organ of Corti
Border cell of organ of Corti
Hensen cell of organ of Corti
Vestibular apparatus supporting cell
Taste bud supporting cell
Olfactory epithelium supporting cell
Schwann cell
Satellite glial cell (encapsulating peripheral nerve cell bodies)
Enteric glial cell Central nervous system neurons and glial cells Astrocyte (various types)
Neuron cells (large variety of types, still poorly classified)
Oligodendrocyte
Spindle neuron Lens cells Anterior lens epithelial cell
Crystallin-containing lens fiber cell
Derived primarily from mesoderm Metabolism and storage cells Hepatocyte (liver cell)
Adipocytes:
    White fat cell
    Brown fat cell
Liver lipocyte Barrier function cells (lung, gut, exocrine
glands and urogenital tract)
Kidney Kidney parietal cell
Kidney glomerulus podocyte
Kidney proximal tubule brush border cell
Loop of Henle thin segment cell
Kidney distal tubule cell
Kidney collecting duct cell[disambiguation needed]
Type I pneumocyte (lining air space of lung cell)
Pancreatic duct cell (centroacinar cell)

TABLE 6-continued

Nonstriated duct cell (of sweat gland, salivary gland, mammary gland, etc.)
    principal cell
    Intercalated cell
Duct cell (of seminal vesicle, prostate gland, etc.)
Intestinal brush border cell (with microvilli)
Exocrine gland striated duct cell
Gall bladder epithelial cell
Ductulus efferens nonciliated cell
Epididymal principal cell
Epididymal basal cell

Extracellular matrix cells

Ameloblast epithelial cell (tooth enamel secretion)
Planum semilunatum epithelial cell of vestibular system of ear (proteoglycan secretion)
Organ of Corti interdental epithelial cell (secreting tectorial membrane covering hair cells)
Loose connective tissue fibroblasts
Corneal fibroblasts (corneal keratocytes)
Tendon fibroblasts
Bone marrow reticular tissue fibroblasts
Other nonepithelial fibroblasts
Pericyte
Nucleus pulposus cell of intervertebral disc
Cementoblast/cementocyte (tooth root bonelike ewan cell secretion)
Odontoblast/odontocyte (tooth dentin secretion)
Hyaline cartilage chondrocyte
Fibrocartilage chondrocyte
Elastic cartilage chondrocyte
Osteoblast/osteocyte
Osteoprogenitor cell (stem cell of osteoblasts)
Hyalocyte of vitreous body of eye
Stellate cell of perilymphatic space of ear
Hepatic stellate cell (Ito cell)
Pancreatic stelle cell

Contractile cells skeletal muscle Cell
    Red skeletal muscle cell (slow)
    White skeletal muscle cell (fast)
    Intermediate skeletal muscle cell
    nuclear bag cell of muscle spindle
    nuclear chain cell of muscle spindle
Satellite cell (stem cell)
Heart muscle cells
    Ordinary heart muscle cell
    Nodal heart muscle cell
    Purkinje fiber cell
Smooth muscle cell (various types)
Myoepithelial cell of iris
Myoepithelial cell of exocrine glands

Blood and immune system cells

Erythrocyte (red blood cell)
Megakaryocyte (platelet pecursor)
Monocyte (white blood cell)
Connective tissue macrophage (various types)
Epidermal Langerhans cell
Osteoclast (in bone)
Dendritic cell (in lymphoid tissues)
Microglial cell (in central nervous system)
Neutrophil granulocyte
Eosinophil granulocyte
Basophil granulocyte
Hybridoma cell
Mast cell
Helper T cell
Suppressor T cell
Cytotoxic T cell
Natural Killer T cell
B cell
Natural killer cell
Reticulocyte
Stem cells and committed progenitors for the blood and immune system (various types)

Germ cells

Oogonium/Oocyte
Spermatid
Spermatocyte
Spermatogonium cell (stem cell for spermatocyte)
Spermatozoon

Nurse cells

Ovarian follicle cell
Sertoli cell (in testis)
Thymus epithelial cell

Interstitial cells

Interstitial kidney cells

TABLE 7

B Cell maturation markers for use with the hydrogel particles described herein.

| B-cell type | Cell surface marker(s) |
|---|---|
| Pro-B | CD19, CD20, CD34, CD38, CD45R |
| Pre-B | CD19, CD20, CD38, CD45R |
| Immature B | CD19, CD20, CD40, CD45R, IgM |
| Tr-B | CD10, CD19, CD20, CD24, CD28 |
| Naïve-B | CD19, CD20, CD23, CD40, CD150 (SLAM), IgD, IgM |
| B-1 | CD19, CD20, CD27, IgM |
| Memory B | CD19, CD20, CD28, CD40, IgA, IgG |
| Plasma Cell | CD19, CD28, CD31, CD38, CD40, CD95 (FAS), CD184 (CXCR4) |

TABLE 8

Cell surface markers for use with the hydrogel particles described herein.

14-3-3 ζ ± η²
14-3-3 ζμ
14-3-3 ζ¶
14-3-3 ζ,
14-3-3 ζf
15-Lipoxygenase 1
160 kD Neurofilament Medium
200 kD Neurofilament Heavy
2H2
3G11 sialoganglioside antigen
4E-BP1
4E-BP1 Phospho (Thr37/46)
5-Methylcytidine
5HT3A receptor
5T4
68 kDa Neurofilament Light
7.1
70 kD Neurofilament Light
A20
A2B5
AAK1
ABCA1
ABCA7
ABCB4
ABCB5
ABCC10
ABCC11
ABCG1
ABI2
ABIN3
ABIN3η²
ABL2
Abraxas
ACAA1
ACADM
ACAT2

TABLE 8-continued

Cell surface markers for use with the hydrogel particles described herein.

ACBD3
ACD
ACE2
Acetyl Coenzyme A Carboxylase
Acetyl Coenzyme A Carboxylase α
Acetyl Coenzyme A Synthetase
Acetylated Lysine
AChRα
AChRβ2
AChRβ3
Aconitase2
ACOT12
ACSA2
ACSF2
ACSM5
Act1
Activation molecule 8 (B cells)
Activin A Receptor Type IB
Activin A Receptor Type IIB
ACTN3
ACY1
ACY3
ADA
ADAM12
ADE2
Adenosine A1 Receptor
Adenosine A2aR
Adenovirus
Adenovirus Fiber monomer and trimer
Adenovirus hexon protein
Adenylate Kinase 1
Adenylosuccinate Lyase
ADFP
ADH1B
ADH6
ADH7
ADI1
Adiponectin
Adiponectin Receptor 2
Adipose Triglyceride Lipase
ADP Ribosylation Factor
ADP-ribosyltransferase 2.2 gene
Adrenodoxin
AF10
AFAP1
AFP
AG2
AGAP1
AGPAT5
AGR2
AHSG
AICDA
AID
AIF
AIM-2
Aiolos
AIPL1
AIRE
AK3
AK3L1
AK5
Akt
Akt (pS473)
Akt (pT308)
Akt1
Akt2
Akt3
Albumin
Alcohol Dehydrogenase
Aldehyde Reductase
ALDH1A1
ALDH1L1
ALDH2
ALDH3A1
ALDH3A2
ALDH5A1
ALDH6A1
ALDH7A1
ALDOB
Aldolase B
Alexa Fluor 405/Cascade Blue
Alexa Fluor 488
ALG2
Alix
Allergin1
alpha 1 Antitrypsin
alpha 1 Catenin
alpha 1 Sodium Potassium ATPase
alpha 2 Catenin
alpha 2 Macroglobulin
alpha Actin 1
alpha Actin 2
alpha Actinin
alpha Actinin 2
alpha Actinin 3
alpha Actinin 4
alpha Adaptin
alpha Adducin
alpha B Crystallin
alpha Fodrin
alpha Internexin
alpha Synuclein
ALS1
AMACR
Aminopeptidase P
AML1
Amphiphysin
AMPKα
AMPKα1
AMPKα2
AMPKβ1
AMPKγ1
Amyloidβ 42
ANAPC2
AND1
Androgen Receptor
Angiotensin I
Angiotensin II Receptor 2
Angiotensin III
ANKRD53
Annexin IV
Annexin V
ANP
Anti-*Kudoa thrysites*
Anti-*T. brucei* procyclin (GPEET)
Anti-*T. brucei* procyclin (phosphorylated GPEET)
Antiglobulin (Coombs)
Antithrombin III
AP2 α
AP2 α β2
AP2 β3
AP2M1
AP2S1
APAF1
APBB3
APC
APC-1
APC-10
APC-11
APC-2
APC-3
APC-5
APC-7
APC-8
APE1
APG12
APG3
APG5
APG7
APMAP
Apo-2.7
Apo-2.7 (7A6)
ApoE
ApoE4

TABLE 8-continued

Cell surface markers for use with the hydrogel particles described herein.

APOER2
Apolipoprotein AI
Apolipoprotein AII
Apolipoprotein AIV
Apolipoprotein B
Apolipoprotein CIII
Apolipoprotein D
Apolipoprotein E
Apolipoprotein F
Apolipoprotein H
Apolipoprotein J
Apolipoprotein L1
Apolipoprotein M
Apoptotic neutrophils
APP
Aquaporin 1
Aquaporin 5
ARF1
ARF5
ARFGAP1
ARFRP1
Argonaute-1
ARH
ARHGAP25
ARHGAP4
ARL11
ARL5B
ARPC5
Artemis
Aryl hydrocarbon Receptor
ASB-1
ASCC1
ASCC2
ASGPR
Asialo-GM1
ASK1
Asparagine synthetase
Ataxin 1
ATF1
ATF2
ATG4A
ATG9A
ATIC
Atlantic Salmon Ig
ATM
ATP citrate lyase
ATP1B3
ATP5A
ATP5H
ATP5J
ATP5O
ATP6V0D1
ATP6V1B1
ATPB
ATRIP
Aurora A
Aurora A Phospho (Thr288)
Aurora B
Aurora B Phospho (Thr232)
AVEN
Avian Influenza A Neuraminidase
Avidin
Axin 2
Axl
B and Activated T Cells
B Cell
B Cell Subset
B cells (pan reactive)
B lymphocytes antibody [UCH-B1]
b-Endorphin
B-Raf Phospho (Thr598/Ser601)
B18R
B7-H4
BACE1
BACE2
BACH1
baculovirus envelope gp64 protein TABLE 8-continued Cell surface markers for use with the hydrogel particles described herein.

BAG1
BAG2
BAG3
BAG4
BAIAP2
BAK
BAMBI
BAP31
BAP37
basal cell Cytokeratin
Basophils
Bassoon
BATF
Bax
BCAR1
BCAR2
BCKD complex E2 subunit
Bcl-10
Bcl-2
Bcl-2 (pS70)
Bcl-2 like 12
Bcl-2 like 2
Bcl-22
Bcl-2A1
Bcl-2Î±
Bcl-3
Bcl-6
Bcl-xL
Bcl-XS/L
BCR
BCSC1
BDH2
BDKRB2
BDNF
Beclin1
Bestrophin 3
beta 2 Adrenoreceptor
Beta 3 Adrenergic Receptor
beta 3 Sodium Potassium ATPase
beta Actin
beta Arrestin 1
beta Arrestin 2
beta Catenin
beta Catenin (npaa 27-37)
beta Catenin (npaa 35-50)
beta Catenin (pS45)
beta Dystroglycan
beta galactosidase
beta galactosidase fusion proteins
beta Synuclein
beta2 Microglobulin
BHMT
Bid
Biglycan
Bilirubin Oxidase
Bim
BimL
BIN1
BIN3
Biotin
BiP
BLBP
Blimp-1
BLK
BLNK
BLNK (pY84)
Blood Group A Antigen
Blood Group AB Antigen
Blood Group B Antigen
Blood Group H ab Antigen
Blood Group H ab Antigen/n Antigen
Blood Group H inhibitor
Blood Group Lewis a
Blood Group M Antigen
Blood Group N Antigen
Blooms Syndrome Protein Blm
BM1

TABLE 8-continued

Cell surface markers for use with the hydrogel particles described herein.

BMAL1
BMI1
Bmk
BMP15
BMP4
BMP7
BMPR1A
BMPR2
BMX
bMyc
BNIP2
BNIP3
BNIP3L
BOB1
BORA
Borealin
*Borrelia burgdorferi*
BPI
BRaf
BRCA1
BRCC36
BRD3
BrdU
BRF1
BRG1
BRN3A
Btk
Btk (pY551)/Itk (pY511)
BTLN-2
BTN1A1
Bu1
Bu1a
Bu1a/Bu1b
Bu1b
BubR1
Bulb
Butyrylcholinesterase
C peptide
C reactive protein
C/EBPÎ²
C1 Inhibitor
C15orf40
C16orf72
C1orf50
C1Q
C1QA
C1QB
C1QC
C1QG
C1r
C1s
C20orf30
C20orf43
C21orf56
C21orf59
C2orf43
C3
C3aR
C3b
C3c
C3d
C4
C4 binding protein
C4b
C4c
C4d
C4orf42
C5
C5aR1
C5L2
C6
C6orf64
C8A/B/G
C9
C9orf41
CA125
CA19.9
CAB39
CACNA1S
CACNA2
CACNG1
CAD
Cadherin 1
Cadherin 10
Cadherin 11
Cadherin 7
Cadherin 8
Cadherin 9
Cadherin E
Cadherin H
Cadherin K
Cadherin P
Cadherin R
CAK C Terminus
CAK N Terminus
CAK Phospho (Ser164/Thr170)
Calbindin
Calcineurin A
Calcitonin Receptor
Calcium Sensing Receptor
Caldesmon
Calgranulin A
Calgranulin B
Calmodulin
Calnexin - ER membrane marker
Calpain 1
Calpain 2
Calpain 9
Calpain S1 (small subunit)
Calpastatin
Calponin
Calreticulin
Calretinin
Calsequestrin 2
CaMKI
CaMKII
CaMKII Phospho (Thr286)
CaMKIIÎ´
CamKIV
CaMKIÎ±
CAMLG
cAMP Protein Kinase Catalytic subunit
cAMP Protein Kinase Catalytic subunit Î±
Cannabinoid Receptor I
Cannabinoid Receptor II
CAP-G2
CAP18
CAP2
CAP3
Carbonic Anhydrase I
Carbonic Anhydrase IX
Carboxylesterase 1
Carboxypeptidase A1
Carboxypeptidase A2
CARD11
CARD8
CARD9
Cardiac Troponin T
CARKL
CARM1
Casein Kinase 1 Î±
Casein Kinase 1 Î³2
Casein Kinase 2 Î²
Caspase 1
Caspase 10
Caspase 11
Caspase 12
Caspase 2
Caspase 2L
Caspase 3
Caspase 4
Caspase 5
Caspase 6
Caspase 7

TABLE 8-continued

Cell surface markers for use with the hydrogel particles described herein.

Caspase 8
Caspase 9
Catalase
Catechol-O-methyltransferase
Cathepsin D
Cathepsin K
Cathepsin L
Caveolin1
Caveolin1 (pY14)
Caveolin2
Cbl
CBP
CBWD1
CBX1
cCbl (pY700)
cCbl (pY774)
CCDC98
CCK4
CCL11
CCL17
CCL18
CCL19-Fc
CCL20
CCL21
CCL25
CCL3
CCL5
CCL6
CCNB1IP1
CCR10
CCR11
CCRD6
CCRL2
CD1
CD1.1
CD10
CD100
CD101
CD102
CD103
CD104
CD105
CD106
CD107a
CD107b
CD108
CD109
CD11
CD110
CD111
CD112
CD113
CD114
CD115
CD116
CD117
CD118
CD119
CD11a
CD11a, strain polymorphism
CD11a/CD18
CD11b
CD11b/c
CD11c
CD11d
CD120a
CD120b
CD121a
CD121b
CD122
CD123
CD124
CD125
CD126
CD127
CD129
CD13

TABLE 8-continued

Cell surface markers for use with the hydrogel particles described herein.

CD130
CD131
CD132
CD133
CD133/2
CD134
CD135
CD136
CD137
CD137L
CD138
CD139
CD14
CD140a
CD140b
CD140b (pY1009)
CD140b (pY1021)
CD140b (pY771)
CD140b (pY857)
CD141
CD142
CD143
CD144
CD146
CD147
CD148
CD15
CD150
CD151
CD152
CD153
CD154
CD155
CD156c
CD157
CD158a
CD158a/h
CD158b
CD158b1/b2/j
CD158d
CD158e
CD158e/k
CD158e1
CD158e1/e2
CD158f
CD158g
CD158h
CD158i
CD158j
CD159a
CD159c
CD15s
CD16
CD16/32
CD16/56
CD160
CD161
CD161a
CD162
CD162R
CD163
CD164
CD165
CD166
CD167a
CD168
CD169
CD16b
CD17
CD170
CD171
CD172
CD172a
CD172a/b
CD172b
CD172g
CD173

TABLE 8-continued

Cell surface markers for use with the hydrogel particles described herein.

CD177
CD178
CD178.1
CD179a
CD179b
CD18
CD180
CD181
CD182
CD183
CD184
CD185
CD186
CD19
CD191
CD192
CD193
CD194
CD195
CD195 (cytoplasmic)
CD195 Phospho (Ser337)
CD195 Phospho (Ser349)
CD196
CD197
CD198
CD199
CD1a
CD1b
CD1b/c
CD1c
CD1d
CD1d Î ± GalCer Complex
CD2
CD20
CD200
CD200R
CD200R3
CD201
CD202b
CD203a
CD203c
CD204
CD205
CD206
CD207
CD208
CD209
CD209b
CD21
CD21/CD35
CD210
CD212
CD213a1
CD213a2
CD217
CD218a
CD22
CD22 (pY822)
CD22.2
CD220
CD220α
CD221
CD221 (pY1131)
CD222
CD223
CD224
CD226
CD227
CD229
CD229.1
CD23
CD230
CD231
CD233
CD234
CD235a
CD235ab

TABLE 8-continued

Cell surface markers for use with the hydrogel particles described herein.

CD236
CD239
CD24
CD240CE
CD240DCE
CD243
CD244
CD244.1
CD244.2
CD245
CD246
CD247
CD247 (pY142)
CD249
CD25
CD252
CD253
CD254
CD255
CD256
CD257
CD258
CD26
CD261
CD262
CD263
CD264
CD265
CD266
CD267
CD268
CD269
CD27
CD270
CD271
CD272
CD273
CD274
CD275
CD276
CD277
CD278
CD279
CD28
CD280
CD281
CD282
CD283
CD284
CD284/MD2 Complex
CD286
CD289
CD29
CD290
CD294
CD298
CD299
CD2a
CD3
CD3/CD44
CD30
CD300
CD300a
CD300e
CD300f
CD301
CD303
CD303a
CD304
CD305
CD307d
CD309
CD31
CD310
CD312
CD314
CD314 (activating)

TABLE 8-continued

Cell surface markers for use with the hydrogel particles described herein.

CD314 (blocking)
CD317
CD318
CD319
CD32
CD321
CD323
CD324
CD325
CD326
CD328
CD329
CD32B
CD33
CD334
CD335
CD336
CD337
CD338
CD339
CD34
CD340
CD344
CD349
CD35
CD351
CD354
CD357
CD358
CD36
CD360
CD361
CD36L1
CD37
CD38
CD39
CD39L4
CD3D
CD3G
CD3Î³
CD3Î'
CD3Îµ
CD3Îµ (CD3 Molecular Complex)
CD4
CD4 (domain 1)
CD4 (domain 2)
CD4 v4
CD40
CD40bp
CD41
CD41/CD61
CD41a
CD41b
CD42a
CD42b
CD42d
CD43
CD44
CD44 (v3)
CD44 (v4)
CD44 (v5)
CD44 (v6)
CD44 (v7)
CD44.2
CD44std
CD44v6
CD44var (v10)
CD44var (v3)
CD44var (v3-v10)
CD44var (v4)
CD44var (v5)
CD44var (v6)
CD44var (v7)
CD44var (v7-v8)
CD45
CD45.1
CD45.2

TABLE 8-continued

Cell surface markers for use with the hydrogel particles described herein.

CD45R
CD45RA
CD45RB
CD45RC
CD45RO
CD46
CD47
CD48
CD49a
CD49a/CD29
CD49b
CD49b/CD29
CD49b/CD61
CD49c
CD49d
CD49d/CD29
CD49e
CD49e/CD29
CD49f
CD49f/CD29
CD4Î±
CD5
CD5.1
CD5.2
CD5.6
CD50
CD51
CD51/61
CD52
CD53
CD54
CD55
CD56
CD57
CD58
CD59
CD59a
CD6
CD60b
CD61
CD62E
CD62L
CD62P
CD63
CD64
CD64 a, b alloantigens
CD64.1
CD65
CD65s (CD65 sialylated)
CD66
CD66a
CD66a/b/c/e
CD66a/c/d
CD66a/c/d/e
CD66a/c/e
CD66a/e
CD66b
CD66c
CD66c/e
CD66e
CD66f
CD68
CD69
CD7
CD70
CD70b
CD71
CD72
CD72 a, b, c alloantigens
CD72 b, c alloantigens
CD72.1
CD73
CD74
CD75
CD77
CD78
CD79a TABLE 8-continued Cell surface markers for use with the hydrogel particles described herein.

CD79b
CD8
CD80
CD81
CD82
CD83
CD84
CD85
CD85a
CD85d
CD85g
CD85h
CD85j
CD85k
CD86
CD87
CD88
CD89
CD8Î±
CD8Î±.1
CD8Î±.2
CD8Î²
CD9
CD90.1
CD90.2
CD90.9
CD91
CD91Î±
CD91Î²
CD93
CD94
CD95
CD96
CD97
CD98
CD98hc
CD99
CD99R
Cdc-123
Cdc-2 (p34)
Cdc-25A Phosph (Ser17)
Cdc-25C
Cdc-37
Cdc-45L
Cdc-6
CDc-7
Cdk1
Cdk2
Cdk4
Cdk5
Cdk6
Cdk7
Cdk9
CdkA1
CdkN2A
CdkN3
CDT1
CDX2
CEACAM19
CEACAM20
CEACAM7
CEBPÎ±
CEBPÎ²
CEND1
CENPA
CENPE
CENPF
CENPH
Centrin 2
CFAH
cFos
CFTR
CGB5
cGK1
CH2
CHCHD5
CHD3

TABLE 8-continued

Cell surface markers for use with the hydrogel particles described herein.

CHD4
Chemerin
CHIPS, C-terminus
CHIPS, N-terminus
Chk1
Chk2
Chondroitin Sulfate
CHOP
Chromogranin C
ChT1
chTOG
cIAP1
cIAP2
CIAS1
CIDEA
CIP4
CISD1
CITED1
CITED2
cJun
cJun Phospho (Tyr91/Tyr93)
CKIIÎ±
CKMT2
CLASP1
Clathrin
Claudin-1
Claudin-10
Claudin-15
Claudin-16
Claudin-18 (C-term)
Claudin-18 (Mid)
Claudin-4
Claudin-5
Claudin-8
CLAW-H
CLEC12A
CLEC1B
CLEC4A
CLEC4M
CLEC9A
CLIP
CLOCK
*Clostridium botulinum* Toxin B
CLPP
cMaf
cMet TABLE 8-continued Cell surface markers for use with the hydrogel particles described herein.

Connexin 37 (Mid)
Connexin 39
Connexin 39 (Mid)
Connexin 40 (C-term)
Connexin 40 (Mid)
Connexin 43
Connexin 45
Connexin 45 (C-term)
Connexin 46
Connexin 47
Connexin 57 (C-term)
Connexin 57 (Mid)
Contactin 2
COPS3
Coronavirus
Coronin 1A
Coronin 1B
Cortactin
Cortical Thymocytes
COX I
COX I/III
COX II
COX IV
COX VA
COX VIA1
Coxsackie Adenovirus Receptor
CPF
CPI17α
Cpn10
CPO
CPS1
CPT2
CRABP1
CRABP2
CRALBP
Creatine Kinase BB
Creatine Kinase MM
CREB
CREB Phospho (Ser133)
cRel
Cripto1
CRISP3
Crk p38
CrkL
CrkL (pY207)
CROT
CRRY
CRTAM
CRTC3
CRY2
Cryptochrome I
*Cryptosporidium*
*Cryptosporidium Parvum*
CRYZL1
CSK
CSK Binding Protein
CSPS
cSrc
CST2
CTDSP1
CTNNA3
CTNNBL1
Cullin 1
Cullin 2
Cullin 3
Cullin 4A
Cullin 4A/B
Cullin 4B
Cutaneous Lymphocyte Antigen
CUTL1
CX3CL1
CX3CR1
CXCL1
CXCL10
CXCL12α
CXCL12β
CXCL13
CXCL9
CXCR7
CXorf26
Cyanine
CYB5R2
CYB5R3
Cyclin A
Cyclin A2
Cyclin B1
Cyclin B2
Cyclin D1
Cyclin D2
Cyclin D3
Cyclin E
Cyclin E2
Cyclin H
Cyclins D1/D2/D3
Cyclophilin 40
CYLD
CysLT1
Cystatin C
Cystatin S
Cytochrome B245 heavy chain
Cytochrome B245 light chain
Cytochrome c
Cytochrome P450 17A1
Cytochrome P450 19A1
Cytochrome P450 1A2
Cytochrome P450 2A6
Cytochrome P450 2B6
Cytochrome P450 2C9
Cytochrome P450 2J2
Cytochrome P450 3A4
Cytochrome P450 3A5
Cytochrome P450 Reductase
Cytokeratin
Cytokeratin (acidic)
Cytokeratin (basic)
Cytokeratin (Pan-reactive)
Cytokeratin 1
Cytokeratin 10
Cytokeratin 10/13
Cytokeratin 13
Cytokeratin 14
Cytokeratin 14/15/16/19
Cytokeratin 15
Cytokeratin 16
Cytokeratin 17
Cytokeratin 18
Cytokeratin 19
Cytokeratin 2
Cytokeratin 20
Cytokeratin 4
Cytokeratin 4/5/6/8/10/13/18
Cytokeratin 40
Cytokeratin 5
Cytokeratin 5/6/18
Cytokeratin 5/8
Cytokeratin 6
Cytokeratin 6a
Cytokeratin 7
Cytokeratin 7/17
Cytokeratin 8
Cytokeratin 8/18/19
D4-GDI
DAB2
DACH1
DAND5
DAP1
DAP12
DAPK1
DAPK2
DARPP32
Daxx
DAZL
DBC1
DCAMKL1

TABLE 8-continued

Cell surface markers for use with the hydrogel particles described herein.

DCC
DCIR2
DCLRE1B
DCP1a
DcR3
DCTN2
DcTRAIL-R1
DcTRAIL-R2
DCXR
DDB1
DDDDK tag
DDX3
DDX4
DDX50
DECR1
Dectin1
Dectin2
DEF8
Defensin Î ± 1
DELETE
delta 1 Catenin
Delta like protein 1
Delta like protein 4
Delta Opioid Receptor
DeltaC
DeltaD
Dendritic Cell Marker
Deoxycytidine kinase
Desmin
Desmoglein 2
Desmoglein1
Desmoplakin
Destrin
Dextran
DGKA
Dicer
DISC1 (C-term)
DISC1 (Mid)
Dishevelled 3
Disialoganglioside GD2
Disialoganglioside GD3
Dkk1
Dkk3
DLC8
DLK1
Dlx5
DM-GRASP
DMT1
DNA-PKcs
DNA-PKcs Phospho (Thr2609)
DNAI1
DNAJA2
DNAJB2
DNAJC3
DNAPK
DNM1L
Dnmt1
Dnmt3b
DNP
DOK2
DOK7
Dopamine Receptor D1
Dopamine Receptor D3
Dopamine Receptor D5
Dopamine Î² Hydroxylase
Doublecortin
DP1
DPH2
DPP10
DPP3
DPP9
Dppa4
DPYD
DR3
DRAK1
DRAK2
Drebrin

TABLE 8-continued

Cell surface markers for use with the hydrogel particles described herein.

DTYMK
DUSP23
DUSP27
DUSP3
DUSP5
DUSP6
DUX4
DYKDDDDK Epitope Tag
Dynamin
Dynamin1
Dynamitin
Dynein light chain 2
Dysbindin
Dysferlin
Dystrobrevin Î±
Dystrobrevin Î²
Dystroglycan Phospho (Tyr893)
E. Coli O/E
E2A-Pbx1
E2F1
E47
E4BP4
Ea52-68 peptide bound to I-A
Ea52-68 peptide bound to the I-A
EAAT1
Early B Lineage
EBF1
EBI3
EBP50
ECGF1
ECH1
ECRG4
EDA
EDA-A2R
EDG1
EDG2
EDG3
EDG6
EEA1
EEF1G
EEF2
EEF2K
EEN
EFEMP1
EFEMP2
Eg5
Eg5 Phospho (Thr927)
EGF
EGF Receptor
EGF Receptor (pY1173)
EGF Receptor (pY845)
EGF Receptor (pY992)
EGR1
EGR2
EHD1
eIF1
eIF2C2
EIF2S1
eIF2Î³
eIF3
eIF3D
eIF3D (p66)
eIF3F
eIF3G
eIF3H (p40)
eIF3I (p36)
eIF3J
eIF3K
eIF4B
eiF4E
eIF4E (pS209)
eIF4E2
eIF5A
eIF6
Elastase
Elk1
Elk1 (pS383)

TABLE 8-continued

Cell surface markers for use with the hydrogel particles described herein.

ELK3
Elongin B
Elongin C
EMAP II
Embigin
EMG1
Emi1
EMR3
EMSY
Ena/Vasp-like
EndoG
EndoGlyx-1
Endomucin
Endothelial Cells
Endothelial Lipase
Endothelial Venule Marker
Endothelium
Engrailed1
ENO1
Enolase1
eNOS
eNOS (pS1177)
Entpd2
Eomes
Eos
Epac1
Eph Receptor A1
Eph Receptor A2
Eph Receptor A4
Eph Receptor B4
Eph Receptor B6
Ephrin A2
Ephrin A3
EPHX2
EPM2AIP1
EPOR
EPS15R
Epsin 1
Epsin 2
ER-HR3
ER-MP54
ER-TR7
ER81
ERAB
ERCC1
ERG
ERK1
ERK1/2 (pT185/pY187)
ERK1/2 (pT202/pY204)
ERK1/ERK2
ERK2
ERK5
ERMAP
ERp29
ERp72
Erythroid Cells
Erzin/Radixin/Moesin
ERÎ± Phospho(Ser167)
ESAM
Estrogen Inducible Protein pS2
Estrogen Receptor
Estrogen Receptor Î±
Estrogen Receptor Î²
Estrogen Related Receptor alpha
ETAR
Ethenoadenosine
ETS1
EVI2A
EVI2B
EWSR1
EXD1
EXOSC3
EXOSC7
EYA2
EZH1/2
Ezrin
Ezrin (pY353)

TABLE 8-continued

Cell surface markers for use with the hydrogel particles described herein.

F-actin
F10A1
F4/80
FAA4
FABP4
Factor I
Factor IX
Factor VIII.vWF (delete)
Factor XIIIa
FADD
FAHD2A
FAK
FAK (pS910)
FAM119A
FAM175A
FAM84B
FAM91A1
FANCC
FANCD2
Fanconi anemia D2 Phospho (Ser222)
FAP
Fascin
FBP1
FBXO21
FBXO31
FBXO42
FBXO43
Fc Receptor Binding Inhibitor
Fc receptor IgA + IgM
FcR
FcRL6
FcRLA
FcIμRI
FDC
FDFT1
FDPS
FE65
FeLV p27
FEN1
FER
Ferritin Heavy Chain
Ferritin Light Chain
Ferritin, mitochondrial
FES
Fetal Hemoglobin
FGF acidic
FGF basic
FGF21
FGFR1
FGFR2
FGR
FH
FHL1
Fibrillarin
Fibrillin
Fibrinogen
Fibrinogen Î± chain
Fibrinogen Î³ chain
Fibrinopeptide A
Fibrinopeptide B
Fibroblast activation protein Î±
Fibroblast Surface Protein
Fibroblasts/Epithelial cells
Fibronectin
Fibronectin Receptor
Fibulin5
Ficolin B
Filaggrin
Filamin A
FITC
FITC/Oregon Green
FIV
FIV gp120
FIV gp95
FIV p24
FIV p24 gag
FKBP12

TABLE 8-continued

Cell surface markers for use with the hydrogel particles described herein.

FKBP4
FKBP6
FKBPL
FLiC
Flightless1
FLIP
Flt3L
Fluorescent Protein
FLV gp70
FLYWCH2
FMC7
fMLP Receptor
FMRP
FNTA
FNTB
Follicular Dendritic Cells
Fos
FOXA1
FOXA2
FOXC2
FOXD3
FOXI1
FOXJ1
FOXM1
FOXO1
FOXO3A
FOXP1
FOXP3
FPRL1
FR4
Fra2
Fragilis
FRAT1
Frataxin
Frequenin
Frizzled-1
FSHÎ±
FSHÎ²
FUK
FUS
FXYD3
FYB
Fyn
Fyn (pY528)/c-Src (pY530)
Fyn-Related Kinase
FZR1
G-CSF
G3BP
G6PD
GAB1
GAB2
GABA B Receptor 2
GABARAP
GAD65
GAD67
GADD34
Galacto-cerebroside
Galactocerebroside
Galectin 1
Galectin 10
Galectin 3
Galectin 4
Galectin 7
Galectin 8
Galectin 9
gamma Synuclein
Ganglioside GD2
Ganglioside GD3
Ganglioside GM1
Gankyrin
GAP
GAP43
GAPDH
GARP
GAS2
GAS7
GAT2
GATA1
GATA2
GATA3
GATA4
GATM
GBA3
GBE1
GBP1
GBP2
GBP5
GC1qR
GCDFP15
GCDH
GCK1
GCLM
GCN2
GCN5
GCTM2
GDAP1L1
GDF15
Gelsolin
Gemin1
Gephyrin
GFAP
GFP
GILZ
GIMAP4
GIPR
GIT2
GITRL
GLAST
Gli1
Glial Fibrilary Acidic Protein
Glicentin
GLIPR1L1
Glucagon
Glucocorticoid Receptor
Glucocorticoid Receptor alpha
Glucose 1 Dehydrogenase
Glucose 6 Phosphate Isomerase
GLUH1
GLUT1
GLUT2
GLUT4
GLUT5
Glutamate receptor 2
Glutamate receptor 2/3
Glutamate receptor 3
Glutamate receptor 4
Glutaminase
Glutamine Synthetase
Glutaredoxin 2
Glutathione NEM
Glutathione NEW
Glutathione Peroxidase 1
Glutathione Peroxidase 4
Glutathione Reductase
Glutathione S Transferase Î, 2
Glutathione S Transferase Î°1
Glutathione S Transferase Î¼
Glutathione Synthetase
Glycogen synthase 1
Glycoprotein IX
Glycoprotein VI
GM-CSF
GM130
GM3.2
GNB2
GNB2L1
GNLY
GNMT
GnRHR
Golgi Protein (58K)
Golgi Zone
GOLM1
GOLPH2
GOSR1

TABLE 8-continued

Cell surface markers for use with the hydrogel particles described herein.

gp340
gp49R
GPA33
GPCR5C
GPR-120
GPR-143
GPR-151
GPR-18
GPR-30
GPR-40
GPR-48
GPR-49
GPR-50
GPR-56
GPR-73A
GPR-73B
GPR-77
GPR-83
GPR-86
GPR-C5C
GPR-C5D
Granulin
Granulysin
Granzyme A
Granzyme B
Granzyme K
GRAP2
GRASP1
GRASP65
GRB2
GRB7
GRHPR
GRIM19
GRK1
GRK2
GRK3
GRK5
GRK6
Growth hormone receptor
GRP170
GRP94
GSC
GSK3α
GSK3α/β
GSK3β
GSPT2
GST
GST Epitope Tag
GSTA4
GTF2D1
GTPase HRAS
GTPBP4
Guanylate kinase
H-2
H-2.m31
H-2Db
H-2Dd
H-2Kd
H2-M
H2-M3
H2A.X
H2A.X Phospho (Ser139)
H2A1J
H60
HA tag
HADHA
HADHA/HADHB
HADHB
HADHSC
HAND1
HAO1
Haptoglobin
HARS
HARS2
HBF
hCGα
hCGβ hCGβ24
HCN4
HDAC1
HDAC10
HDAC2
HDAC3
HDAC4
HDAC6
HDAC9
HDHD1A
HDHD2
HDJ2
HDLBP
HE4
HEC1
HEF1
Helios
Hematopoiesis related Macrophage
Hematopoietic Lineage Cocktail
Hematopoietic Progenitor Cell
Hemoglobin
Hemoglobin F
Hemoglobin subunit α
Hepatitis B Virus
Hepatitis B Virus Core Antigen
Hepatitis B Virus E Antigen
Hepatitis B Virus Surface Antigen (Ad/Ay)
Hepatitis C Virus
Hepatitis C Virus Core Antigen
Hepatitis C Virus NS4
Hepsin
HER3
HER4
Hes1
Hexokinase
Hexokinase1
Hexokinase2
HFE1
HGF
HGFA Inhibitor 1
HHEX
HHV8 GPCR
HIBCH
HID1
HIF-1α
HIF-2α
HIF1AN
HINT1
HIP2
HIPK2
Hippocalcin
Histamine H3 Receptor
Histocytes
Histone H1
Histone H1.0
Histone H2A
Histone H2B
Histone H2B type 1B
Histone H3
Histone H3 Phospho (Ser10)
Histone H3 Phospho (Ser28)
Histone H3.3
Histone H4
HIV1 Core Antigen
HIV1 p17
HIV1 p24
HIV1 p55/p17
HIV1 tat
HL60
HLA Class I
HLA-2Kb/2Db
HLA-2kb/2Dd
HLA-A
HLA-A/B/C
HLA-A1/A11/A26
HLA-A1/A36
HLA-A10/A11

TABLE 8-continued

Cell surface markers for use with the hydrogel particles described herein.

HLA-A10/A28/B75
HLA-A10/B62/B71
HLA-A11
HLA-A2
HLA-A2/A25/A32
HLA-A2/A28
HLA-A2/A3/A29
HLA-A2/A69
HLA-A2/B17
HLA-A2/B5
HLA-A2/B57
HLA-A23/A24
HLA-A24/A11/A2403
HLA-A25
HLA-A25/A26
HLA-A25/A26/A34
HLA-A25/A32
HLA-A26/A34/B71/B62
HLA-A29
HLA-A3
HLA-A30/A31
HLA-A33/B8
HLA-A34/B71/A26
HLA-A9
HLA-A9/A25/A32
HLA-A9/A32/B13
HLA-B
HLA-B12
HLA-B13/B62/B15
HLA-B14
HLA-B17
HLA-B17/B35/B44
HLA-B21/B70/B55
HLA-B27/B44/B47
HLA-B35/B57/B75/B77
HLA-B44/B75/B17
HLA-B48/B60
HLA-B5/B49/B56
HLA-B7
HLA-B8
HLA-B8/B14
HLA-BC
HLA-Bw4/A9/A32
HLA-Bw6
HLA-Bw6/B77
HLA-class I free chain
HLA-D
HLA-DM
HLA-DO
HLA-DP
HLA-DQ
HLA-DQ/DR
HLA-DQ1/DQ3
HLA-DQ1/DR7
HLA-DQ3
HLA-DQ6
HLA-DQ7
HLA-DQA1
HLA-DQB1
HLA-DQw1
HLA-DR
HLA-DR/DP
HLA-DR/DP/DQ
HLA-DR1
HLA-DR11
HLA-DR3/DR6
HLA-DR4
HLA-DR7
HLA-DR7/DRβ2
HLA-DR8/DR12
HLA-DR9
HLA-DRA
HLA-DRβ2
HLA-DRβ3
HLA-E
HLA-G
HLCS
HLF
HLXB9
HMG14
HMG17
HMG4
HMGB1
HMGB2
HMOX1
HMOX2
HNF4α
hnRNPA1
hnRNPC1/C2
hnRNPD
hnRNPK
hnRNPL
hnRNPU
hnRNPUL1
Homing Receptor
HOXB4
HOXB5
HP1α
HPa1
HPa2
HPD
HPd1
HPd2
HPi1
HPi2
HPi3
HPi4
HPR1
HPRT1
HPV16 E1/E4
HPx1
HPx2
Hrk
Hsc70
HSD17B1
HSD3B1
HSF1
HSF2
HSF4
HSL
Hsp105
Hsp14
Hsp22
HSP25
Hsp27
Hsp40
Hsp47
Hsp60
Hsp70
Hsp70-2
Hsp90
Hsp90α
Hsp90β
HspA4
HspA6
HSPA9
HspB2
HspB7
HSV tag
HTLV I gp46
HTLV I p19
HtrA2/Omi
Human Papillomavirus 16 (E7)
Huntingtin
HUS1
Hydrogen Potassium ATPase β
I-Ak (Aα k)
I-Ak (Aβk)
Ia (B cells)
IBA1
IBP2
ICAD
IDO
IFABP TABLE 8-continued Cell surface markers for use with the hydrogel particles described herein.

IFN-α
IFN-α1
IFN-α2β
IFN-β
IFN-γ
IFN-γRβ
IFN-ω
IFNA1
IFNAR1
IFT88
Ig
Ig (polyspecific)
Ig light chain κ
Ig light chain λ
Ig light chain λ1, λ2, λ3
IgA
IgA (Fab2)
IgA (H)
IgA, κ
IgA, λ
IgA1
IgA2
IgD
IgD (δ heavy chain)
IgDa
IgDb
IgE
IgE, κ
IgEa
IgEb
IgG
IgG (Fab H/L)
IgG (Fab)
IgG (Fab2 Fc)
IgG (Fab2 H/L)
IgG (Fab2)
IgG (Fc)
IgG (H/L)
IgG (γ chain specific)
IgG Fd
IgG light chain
IgG, κ
IgG/IgM
IgG/IgM/IgA
IgG/IgM/IgA (Fab2 H/L)
IgG/IgM/IgA (Fab2)
IgG/IgM/IgA (H/L)
IgG/IgY
IgG1
IgG1 (heavy chain)
IgG1, κ
IgG1, λ
IgG1/2a
IgG1/3
IgG1a
IgG1b
IgG2
IgG2, κ
IgG2, λ
IgG2/3
IgG2a
IgG2a, κ
IgG2a, λ
IgG2a/b
IgG2b
IgG2b, κ
IgG2c
IgG2c, κ
IgG3
IgG3, κ
IgG3, λ
IgG4
IgGDa
IgK
IGKC
IgL
IGLC2

IgM
IgM (Fab2)
IgM (Fc)
IgM (H/L)
IgM, κ
IgM, λ
IgMa
IgMb
IgY
Igα€™s
Ihh
Ikaros
IkBα
IkBβ
IkBε
IKKα
IKKβ
IKKγ p(S376)
IKKμ
IL-10
IL-11Rα
IL-12
IL-12 (p35)
IL-12 (p70)
IL-12 Rβ1
IL-12 Rβ2
IL-12/IL-23 (p40)
IL-13
IL-15
IL-15/IL-15R
IL-15Rα
IL-16
IL-17D
IL-17A
IL-17A/F
IL-17B
IL-17C
IL-17E
IL-17F
IL-18
IL-18BP
IL-19
IL-1RA
IL-1RN
IL-1α
IL-1β
IL-2
IL-20R2
IL-20Rα
IL-20Rβ
IL-21
IL-22
IL-22Rα2
IL-23 (p19)
IL-23R
IL-24
IL-25
IL-27
IL-27 (p28)
IL-27Rα
IL-28
IL-28Rα
IL-29
IL-3
IL-31
IL-32αβγδ
IL-32αδ
IL-33
IL-34
IL-4
IL-4Rα
IL-5
IL-6
IL-7
IL-7Rα
IL-8
IL-9

TABLE 8-continued

Cell surface markers for use with the hydrogel particles described herein.

ILF3
ILK
ILK1
ImmunofluorescenceN-γ
IMP3
Importin9
Influenza A Virus M2 Protein
Influenza B Virus Nucleoprotein
ING1
ING2
ING3
ING4
Inhibin α
iNOS
INPP4A
INPP4B
Insulin
Insulin Degrading Enzyme (IDE)
Insulin Receptor R
Integrin α 4/β7
Integrin α 9/β1
Integrin α V/β5
Integrin α V/β6
Integrin β1 Phospho (Tyr783)
Integrin β1 Phospho (Tyr795)
Integrin β5
Integrin β6
Integrin β7
Intercalated DNA
Intra Acrosomal Protein
Intra-Acrosomal Proteins
Invariant NK T
IP10
IQGA1
IRAK1
IRAK3
IRAK4
IRE1
IRF1
IRF3
IRF4
IRF5
IRF6
IRF7
IRF7 (pS477/pS479)
IRF8
IRF9
IRS1
IRS1 (pY896)
IRS2
IRS4
ISG15
ISG20
ISL1
Isthmin1
ITCH
Integrin α 7
ITK
ITPR1
Jagged2
JAK2
JAK3
JAM2
JAML
Japanese encephalitis virus NS1 glycoprotein
JNK
JNK Phospho (Thr183/Tyr185)
JNK1/JNK2/JNK3
JNK2
Junctional Adhesion Molecule C
Junctophilin-1 (C-term)
Junctophilin-1 (Mid)
Junctophilin-2 (C-term)
Junctophilin-3 (C-term)
KAP1
KATNA1
KCNH1
KDEL
KDM4D
Ki-67
KIF22
KIF3A
KIF4A
KIFA3
Kindlin2
Kinetoplastid Membrane Protein 11 (KMP-1))
KIR-2.1
KIR-2D (pan CD158)
KLF4
KLF6
KLH
KLHL11
KLRA3
KLRC1
KLRG1
KMT4
KMT5A
KOR-SA3544
KS1/4
Ksp37
KSR1
Ku70
Ku70/80
Ku80
*Kudoa Thyrsites*
Kunitz Protease Inhibitor
Kv4.2
L/S-MAG
Labeling Check Reagent
Lactate Dehydrogenase
Lactate Dehydrogenase B
Lambda
Lamin A
Lamin A/C
Lamin B Receptor
Lamin B1
Lamin B2
Lamin C
Laminin
Laminin 5
Laminin Receptor
Laminin β1
LAMP2a
LAMP2b
LAT
LAT (pY171)
LAT (pY226)
LBP
LC3
LC3B
LCAT
Lck
Lck (pY505)
LDH1
LDH1/B/C
LDL (MDA oxidized)
LDLR
LEF1
*Leishmania* LPG (repeat epitope)
*Leishmania* Major Surface Protease (GP-63)
LEKTI
Leukemia Inhibitory Factor
Leukotriene A4 hydrolase
Leukotriene B4 Receptor
LHX3
LI-Cadherin
LIF
DNA Ligase I
DNA Ligase III
LIM kinase 2
LIME1
LIMK1
LIMS1
Lin28

TABLE 8-continued

Cell surface markers for use with the hydrogel particles described herein.

Lineage Cocktail
Lipin 1
LIS1
Liver Carboxylesterase 1
LKB1
LMO2
LOX
LOX1
LRP5/6
LRP6
LRPAP1
LSD1
LSP1
LSS
LTβ
Luciferase
LXRα
Ly-108
Ly-49A
Ly-49A/D
Ly-49AB6
Ly-49C/F/I/H
Ly-49C/I
Ly-49D
Ly-49E/F
Ly-49F
Ly-49G
Ly-49G2
Ly-49G2B6
Ly-49H
Ly-49I
Ly-51
Ly-6A.2/Ly-6E.1
Ly-6A/E
Ly-6b
Ly-6B.2
Ly-6C
Ly-6D
Ly-6G
Ly-6G/C
Ly-6K
Ly-77
Lymphotoxin β
Lymphotoxin β Receptor
Lyn
LYRIC
Lysophospholipase 1
Lysosomal acid lipase
Lysozome
Lysozyme
Lyve1
M-CSF
M13 Bacteriophage Coat Protein g8p
M13 Bacteriophage Protein
MAA
Mac-2BP
macroH2A.1
Macrophage
Macrophage Activator
Macrophage galactose lectin
Macrophage/Granulocyte
Macrophages/Monocytes
MAD2
MadCAM1
MADD
MADH7
MAFB
MAG
MAGE-A
MAGE1
MAIR2
MAIR4
MALT1
Mammaglobin A
MAP1LC3A
MAP2
MAP2B
MAP2K1IP1
MAP3K8
MAP4 Phospho (Ser768)
MAP4K1
MAP4K4
MAPK12
MAPK6
MAPKAP Kinase 2
MAPKAP Kinase 2 Phospho (Thr334)
MARCKS
MARCO
Marginal Zone B Cells
MARK2
MARK3
MART1
Mast Cell
Mast Cell Protease 11
mature macrophage marker
MBD1
MBD2
MBL
MCL1
MCM2
MCM3
MCM4
MCM5
MCM6
MCM7
MCP-1
MCP-4
MCP-8
MCSF
MD1
MD2
MDC
MECT1
MEF2A
MEIS1
MEK1
MEK1 (p298)
MEK1 (pS218)/MEK2 (pS222)
MEK1/2 (pS222)
MEK2
MEK3
MEK4
MEK5
MEK6
MEK7
MEKK1
MEKK2
MEKK3
MEKK4
Melanoma
MELK
MEMO1
Mena
Menin
MEOX2
Merlin
MERTK
Mesothelin
Metallothionein
MetRS
mGluR5
MGMT
MHC Class I
MHC Class I (H-2Db)
MHC Class I (H-2Dd)
MHC Class I (H-2Dk)
MHC Class I (H-2Dq/Lq)
MHC Class I (H-2Kb)
MHC Class I (H-2Kb/Db)
MHC Class I (H-2Kb/Dd)
MHC Class I (H-2Kd a3 domain)
MHC Class I (H-2Kd)
MHC Class I (H-2Kd/Dd)
MHC Class I (H-2Kd/Dd/q/u/v)

TABLE 8-continued

Cell surface markers for use with the hydrogel particles described herein.

MHC Class I (H-2Kk)
MHC Class I (H-2Kq)
MHC Class I (H-2Ks)
MHC Class I (H-2Ld)
MHC Class I (H-2Ld/Db)
MHC Class Ib (H2-M3)
MHC Class II
MHC Class II (DQ)
MHC Class II (DR)
MHC Class II (I-A)
MHC Class II (I-A/E)
MHC Class II (I-Ab)
MHC Class II (I-Ab/Ad)
MHC Class II (I-Ab/As)
MHC Class II (I-Ad)
MHC Class II (I-Ak)
MHC Class II (I-Ak/Ad/Ab/Aq/Ar)
MHC Class II (I-Ak/As)
MHC Class II (I-Ap)
MHC Class II (I-Aq)
MHC Class II (I-E)
MHC Class II (I-EÎ°)
MHC Class II (RT1B)
MHC Class II (RT1Bu)
MHC Class II(RT1D)
MHC Class II Î²
MHC Qa1b
MICA
MICA/MICB
MICB
Microfold (M) Cells
Microtubule Associated Protein 2ab
Microtubule Associated Protein RP/EB 2
Midkine
Mineralocorticoid Receptor
MIP-1Î²
MIPEP
Mitochondria
Mitofilin
Mitofusin 1
Mitofusin 2
Mitotic Cells
MKK6
MLH1
MLK3
MLL1
MLLT11
MMP1
MMP10
MMP11
MMP12
MMP13
MMP14
MMP15
MMP17
MMP19
MMP2
MMP20
MMP21
MMP26
MMP3
MMP8
MMP9
Mnk1
mNOS
MnSOD
Moesin
Monoamine Oxidase B
Monocyte/Granulocyte
Mononuclear Phagocyte
Mouse Embryonic Fibroblast (mEF) Feeder Cells
Mouse Lineage
MPP1
MRCL3
MRE11
MRGPR-X2
MRI1

MRP14
MRP2
MRP3
MRP4
MRP5
MRP6
MRP8
MRP8/14
MSC (W8B2)
MSC (W3D5)
MSC (W5C5)
MSC (W7C6)
MSC/NPC
MSH2
MSH6
MSI2H
MSK1
MST1
MST1/MST2
MST3
MST4
MST4/MST3/STK25
mTOR
Muc-16
Muc-2
Muc-3
Muc-4
Muc-7
MULT-1
Munc13-4
Munc18
MUPP1
Mus81
Musashi1
Muscarinic Acetylcholine Receptor 2
muscle Actin
Muscleblind-like 1
MVP
MYBBP1A
MYBPC3
Myc tag
MyD88
Myelin Basic Protein
Myelin oligodendrocyte glycoprotein
Myelin PLP
Myeloid Antigen
Myeloid Cell Nuclear Differentiation Antigen
Myeloid Lineage
Myocilin
Myogenin
Myosin heavy chain
Myosin IIA
Myosin light chain 2
Myosin light chain 3
Myosin light chain kinase
Myosin Phosphatase
Myosin Phosphatase 1/2
MYST2
NADH2
Naf1
NAK
Nanog
NAPE-PLD
NAT1
Native Lipoteichoic Acid
Natriuretic Peptide Receptor A
Natural Killer Cell
Natural Killer Cell Activation Structures
NBS1
NC1.1
NCF4
Nck
NCOA1
NCOA2
NCX1
NDUFAF1
NDUFB4

TABLE 8-continued

Cell surface markers for use with the hydrogel particles described herein.

NDUFS3
NEDD8
NEK2
NEK6
NEK7
NEK9
NEK9 Phospho (Thr210)
Nestin
NETO2
Neurabin1
Neuregulin1
Neuregulin3
Neuroblastoma
NeuroD1
NeuroD2
Neurofibromin
Neurofilament Heavy Protein
Neurofilament Medium Protein
Neurogenin 2
Neurokinin 1 Receptor
Neuron Specific Enolase
Neuronal Growth Factor Receptor
Neurotensin Receptor 1
NFκB p50/p105
NFκB p65 (pS536)
NFATc1
NFκB p50
NFκB p50/p105
NFκB p52/p100
NFκB p65
NFκB p65 (pS529)
NG2
NGF
Nhedc2
NHERF1
Nicastrin
Ninein
Nitrotyrosine
NKG2A/C/E
NKG2AB6
NKp80
NKX3.1
NM23A
NMDA Receptor 2A
NMDA Receptor 2B
NMDE2
NMDZ1
NMNA2
nMyc
nNOS
NNTM
Nociceptin
Nod2
Nodal
Noggin
NONO
Nonspecific Cytotoxic Cells
Notch1
Notch2
Notch3
Notch4
NOX2
NOX4
NOXA2
NPC
NPM-ALK
NPM/B23 Phospho (Thr199)
NPM/B23 Phospho (Thr234/Thr237)
NPY5R
NQO1
NR2E1
NRC2C
Nrf2
NRG3
NSPA/B
NTAL
NTF97
Nucleolin
Nucleolin Phospho (Thr76/Thr84)
Nucleophosmin
NUDC
NUMA1
Nur77
O acetyl GD3
Oct2
Oct3/4
Oct3/4A
Oct4
ODAG
OGDH
OLIG1
OLIG2
Oligodendrocyte Marker
Oligodendrocyte Marker O1
Oligodendrocyte Marker O4
Oncostatin M Receptor
Orai1
OSCAR
OSR1
Osteonectin
Osteopontin
Osteoprotegerin
Otx2
OVA (SIINFEKL) H-2Kb
Oval Cell Marker
Ovalbumin
Ovarian Carcinoma-associated Antigen
OX-62
p110α
p120 Catenin
p120 Catenin (pS268)
p120 Catenin (pS288)
p120 Catenin (pS879)
p120 Catenin (pT310)
p120 Catenin (pT916)
p120 Catenin (pY228)
p13
p130
p130 Cas
p130 Cas (pY249)
p14ARF
p150, 95
p19ARF
p21
p22phox
p23
p27Kip1
P2RX4
P2RY8
P2X3
P2X7
P2Y6
p34Cdc-2
p38
p38 MAPK (pT180/pY182)
p400
p53
p53 Acetylated (Lys305)
p53 Acetylated (Lys382)
p53 Phospho (Ser15)
p53 Phospho (Ser37)
p53 Phospho (Ser392)
p53BP1 (Ser1778)
p57Kip2
p60 CAF1
p62
p63
p63 (TA)
p70 S6 Kinase β
p90 Rsk
p90 Rsk Phospho (Thr368/Ser372)
p95 NBS1
p97
PA28β

TABLE 8-continued

Cell surface markers for use with the hydrogel particles described herein.

PABP1
PABP2
PABPN1
PAC1
PAD2
PAG1
PAK1
PAK2
PAK3
pan Actin
pan Macrophage
Panendothelial Cell Antigen
PAR1
Parainfluenza Virus type 1
Parainfluenza Virus type 2
Parainfluenza Virus type 3
PARC
PARD3
PARK7/DJ1
PARP, Cleaved Form
PARP16
PARP4
PARVA
Pax2
Pax5
Pax6
Pax7
Pax8
Pax9
Paxillin
Paxillin Phospho (Tyr118)
Paxillin Phospho (Tyr31)
PBEF
PBK
PBP
PBR
PBX3
PCB
PCNA
PCYT1A
PD-1H
PD-ECGF
PDC-TREM
PDCD4
PDCD6
PDE3B
PDECGF
PDGF-AA
PDI
PDK1
PDK2
PDPK1
PDPK1 (pS241)
PDX1
PDZK1
PE
PECR
PEI-Transferrinfection
Pellino 1
Pentraxin 3
PEPD
Perforin
Peroxiredoxin 1
Peroxiredoxin 2
Peroxiredoxin 6
PEX5
PF4
PGC1α
PGIS
PGP9.5
PGRP-Ia
PGRP-S
PHD1
PHD2
Phosphatidylserine
Phospho SHIP
Phospholipase A2 activator protein (PLAP)

TABLE 8-continued

Cell surface markers for use with the hydrogel particles described herein.

Phospholipase C γ3
Phospholipase C β1
Phospholipase D1
Phosphoserine/threonine/tyrosine
Phosphotyrosine
PI 3 Kinase catalytic subunit α
PI 3 Kinase catalytic subunit β
PI 3 Kinase p110 γ
PI 3 Kinase p110 δ
PI 3 Kinase p150
PI 3 Kinase p85 α
PI 4 kinase γ
PIAS1
PIAS3
PICK1
PIM1
PIM2
Pin1
PINK1
PIP5K2α
PIP5KIβ
PIR-A/B
Pirh2
PIST
PiTX3
PIWIL2
PKA RIα (pS99)
PKA RIβ (pS114)
PKA2γ
PKAR2
PKAβ
PKC
PKCq
PKCα
PKCα (pT497)
PKCα (pT638)
PKCγ
PKCγ2
PKCβ
PKCδ
PKCμ
PKC¶
PKCι
PKCϊ...
PKN
PKN2
PKR
PKX1
PLA2G1B
Placental alkaline phosphatase
Placental Protein 14
Plakophilin 3
Plastin L
Platelet
PLAU
PLCβ1
PLCβ1 (pY783)
PLCγ2
PLCγ2 (pY759)
Plectin
Pleiotrophin
PlexinA1
PlexinB2
PLGF
PLK1
PLK1 Phospho (Thr210)
PLK4
PLSCR1
PLVAP
PLZF
PMCA(1-4)
PMCA4
PMEL17/SILV
PMN
PMP70
PMS2
PNAd

TABLE 8-continued

Cell surface markers for use with the hydrogel particles described herein.

PNPH
Podocalyxin
Podoplanin
POKEMON
Polyhistidine Tag
PON1
PON3
PP2Aα
PP2Aα±β
PPM1A
PPP1A
PPP5C
PPP6C
PR3
PRA1
PRC1
Pre-BCR
Pre-T Cell Receptor α Chain
Prealbumin
Presenilin1
Presenilin2
Prion protein PrP
PRKRA
PRLR
PRMT1
PRMT5
pro Relaxin 1/2
pro Relaxin 2
Profilin1
Progesterone Receptor
Prohibitin
Prokineticin 1
Prokineticin 2
Prolactin
ProMBP1
Prostaglandin D2 Receptor
Prostaglandin dehydrogenase 1
Prostaglandin E Receptor EP3
Prostate Cell Surface Antigen
Prostate Specific Antigen
Prostatic Acid Phosphatase
Proteasome 20S C2
Proteasome 20S α 2
Proteasome 20S α 3
Proteasome 20S α 5
Proteasome 20S α 6
Proteasome 20S α 7
Proteasome 20Sα 1/2/3/5/6/7
Protein A
Protein G
Protein Kinase D2
Protein Phosphatase 1β
Protein phosphotase inhibitor 1
Protein S
Proteinase Activated Receptor 4
Prothrombin
PSA-NCAM
PSD95
*Pseudomonas Aeruginosa*
PSMA
PSMD14
Psoriasin
PTAFR
PTBP1
PTEN
PTGER2
PTGER4
PTHLH
PTK7
PTP1B
PTP4A2
PTPS
PTPη
PTRH2
PU.1
PU60
PUMA

TABLE 8-continued

Cell surface markers for use with the hydrogel particles described herein.

PUMAβ
Pumilio1
Pumilio2
PXR
PYCARD
Pygopus2
Pyk2
Pyk2 (pY402)
Pyruvate Dehydrogenase E1α
Pyruvate Dehydrogenase E2
Pyruvate Dehydrogenase E2/E3bp
q2
Qa1(b)
Qa2
RAB11A
RAB25
RAB27A
RAB4
RAB5a
RAB9
Rac1
Rac1/Cdc42
RAD17
RAD17 Phospho (Ser645)
RAD23A
RAD51
RAD54
RAD9A
Radixin
RAE-1β
RAE-1γ
RAF1
RAGE
RAIDD
Rainbow Trout Ig
RalBP1
RanBP9
RanGAP1
RAP1A/RAP1B
RAP1GAP
Raptor
RARα
RAS
RASGAP
RASGRF1
RASSF1A
Rb
Rb (a.a. 332-344)
Rb (pS780)
Rb (pS807/pS811)
RbAp46
RbAp48
RBC
RBC (Polyclonal Rabbit)
RBM35A
RBP4
RBX1
RCC1
RcRL6
Red Blood Cell
Relaxin 1
Relaxin 1/2
Relaxin 2
RelB
RELMβ
RELT
Renin
RENT1
Reptin
Repulsive Guidance Molecule C
Resistin
REST
Ret
Reticular Fibroblasts and Reticular Fibres
Reticulon1A
Reticulum Cells
Retinoblastoma 1

TABLE 8-continued

Cell surface markers for use with the hydrogel particles described herein.

RFLAT1
RFP
RGS6
RGS7
RGS9
RHEB
Rho
RhoA
RHOC
RhoGAP
RhoGDI
RIAM
RICTOR
RIG1
RIP1
RIP2
Rituximab
RLA DQ
RLA DR
RNA polymerase II
RNA polymerase II CTD repeat YSPTSPS
RNASE-L
RNASE1
RNF144B
RNF168
RNF36
RNPEP
ROCK1
ROR1
ROR2
RORÎ±
RORÎ³
ROS
RPA32/RPA2
RPA70
RPS6
RSF1
RSK1 p90
RSK2
RSK3
RSK4
RT1A
RT1Aa
RT1Aa, b
RT1Aa, b, l
RT1Ac
RT1Au
RT1B
RT6.1
RT6.2
Ryanodine Receptor
RYK
RyR
S-Tag
S100A1
S100A10
S100A13
S100A4
S100A6
S100A9
S100Î±
S100Î² 2
s100Î²
S6 (pS235/pS236)
S6 (pS240)
S6 (pS244)
S6K
SAA4
Sall4
*Salmonella Paratyphi* A
*Salmonella Typhimurium*
Salmonid Ig (H and L chain)
Salmonid Ig (H chain)
SAM68
SAMD2
SAP
SARA TABLE 8-continued Cell surface markers for use with the hydrogel particles described herein.

SATB1
SATB2
SC5A5
SC6A4
SCAI
SCD1
Scramblase1
SCY1-like 3
SDF1
SDF1Î±
SDHA
SDHB
Secretory component
Securin
SELP
Sema4A
Sema7A
SENP1
SEPP1
SERCA2
SerpinB1
SerpinB2
SerpinB6
Sestrin1
SFRP2
SGK1
SHC1
*Shigella Boydii*
SHIP1
SHP1
SHP2
SHP2 (pY542)
SIAH2
SIGIRR
Siglec-10
Siglec-8
Siglec-9
Siglec-F
Siglec-H
SIK2
SIRT1
SIRT2
SIRT3
SIRT5
SIT1
SIX2
SKP1A
SLA-DR
Slan
SLC1A3
SLC1A7
SLC22A1
SLC22A5
SLC26A6
SLC26A7
SLC30A4
SLC39A11
SLC4A3
SLC6A19
SLC6A6
SLC7A10
SLC7A14
SLC7A3
SLC7A8
SLC8A2
SLC9A6
SLP76
SLP76 (pY128)
SM22Î±
SMAC
SMAC3
SMAD1
SMAD1 (pS463/465)
SMAD1/5
SMAD1/9
SMAD2
SMAD2/3 (pS465/467) DELETE TABLE 8-continued Cell surface markers for use with the hydrogel particles described herein.

SMAD3
SMAD4
SMAD5
SMAD6
SMC1
SMC1L1
SMN
Smoothelin
SMURF2
SNAP25
SNX1
SOAT1
SOCS1
SOCS2
SOCS3
SOCS6
SOD2
Sodium Potassium ATPase
Sonic Hedgehog
Sortilin
SOSC3
SOX1
SOX10
SOX17
SOX18
SOX2
SOX2 (COOH terminus)
SOX2 (NH2 terminus)
SOX9
SP-D
Sp1
Sp3
Spectrin Î±1
SPHK1
Spt16
Src (pY418)
SREBP1
ssDNA
SSEA3
SSEA4
SSEA5
SSH3BP1
SSR2
SSR5
SSRP1
SSX2IP
Stat1
Stat1 (N-Terminus)
Stat1 (pS727)
Stat1 (pY701)
Stat1Î±
Stat2
Stat3
Stat3 (pS727)
Stat3 (pY705)
Stat4
Stat4 (pY693)
Stat5
Stat5 (pY694)
Stat5a
Stat5b
Stat6
Stat6 (pY641)
Stathmin/Op18 Phospho (Ser16)
Stathmin1
Stefin B
Stem Cell Factor
STIM1
STK3
STK33
STK39
STOM
STRO1
STUB1
SULT1A1
SULT1A3/SULT1A4
SULT1C2

TABLE 8-continued

Cell surface markers for use with the hydrogel particles described herein.

SULT2A1
SUMO1
SUMO2
SUMO3
SUN1
Suppressor of Fused
SUPT16H
Survivin
Survivin Phospho (Thr34)
SV40 Large T and Small t Antigens
SWC1a
SWC6
SYBL1
Syk
Syk (pY348)
Synapsin I
Synapsin II
Synaptojanin2
Synaptophysin
Syndecan4
SynGAP
Synip
Syntaxin
Syntaxin6
Syntrophin
SYWC
T cells (pan reactive)
T Lymphocytes
T- and B-Cell Activation Antigen
T7 tag
TAB1
TACE
TACI
TAF172
TAF250
TAG72
Talin1
Talin2
Tamm Horsfall (Uromucoid)
TANK1
TAP1
TAP2
TARDBP
TARP
Tartrate-resistant acid phosphatase
TAS1R1
Tau
TBA1B
Tbet
TBK1 (pS172)
TBX1
TC10
TCF3
TCF7L1
TCF7L2
TCL1
TCP1Î±
TCP1Î²
TCR
TCR DO11.10
TCR HY
TCR VÎ±11
TCR VÎ±11.1/11.2b, d
TCR VÎ±2
TCR VÎ±24
TCR VÎ±24-JÎ±18
TCR VÎ±3.2
TCR VÎ±3.2b, c
TCR VÎ±7.2
TCR VÎ±8
TCR VÎ±8.3
TCR VÎ²1
TCR VÎ²10a
TCR VÎ²10b
TCR VÎ²11
TCR VÎ²12
TCR VÎ²12b

TABLE 8-continued

Cell surface markers for use with the hydrogel particles described herein.

- TCR Vβ13
- TCR Vβ13.1
- TCR Vβ13.2
- TCR Vβ13.6
- TCR Vβ14
- TCR Vβ16
- TCR Vβ17
- TCR Vβ17α
- TCR Vβ18
- TCR Vβ2
- TCR Vβ20
- TCR Vβ21.3
- TCR Vβ22
- TCR Vβ23
- TCR Vβ3
- TCR Vβ4
- TCR Vβ5
- TCR Vβ5.1
- TCR Vβ5.1/5.2
- TCR Vβ5.2
- TCR Vβ5.3
- TCR Vβ6
- TCR Vβ7
- TCR Vβ7.1
- TCR Vβ7.2
- TCR Vβ8
- TCR Vβ8.1/8.2
- TCR Vβ8.2
- TCR Vβ8.2/8.3
- TCR Vβ8.2/8.4
- TCR Vβ8.3
- TCR Vβ8.5
- TCR Vβ9
- TCR Vγ1.1
- TCR Vγ1.1/γ1.2
- TCR Vγ2
- TCR Vγ3
- TCR Vγ9
- TCR Vδ1
- TCR Vδ2
- TCR Vδ4
- TCR Vδ6.3/2
- TCR α
- TCR α ± β
- TCR β
- TCR ζζ'
- TCR γ
- TCTP
- TdT
- Tec
- TEF1
- TEM8
- Tenascin C
- TER119
- TERF2
- Terminal-Deoxynucleotidyl Transferase
- TERT
- Tetranectin
- TFF3
- TFIIB
- TGF-β
- TGF-β1
- TGF-β3
- TGF-βR1
- TGF-βR2
- TGN38
- TGN46
- THAP11
- THEMIS
- Thioredoxin
- Thioredoxin Reductase 1
- ThPOK
- Thrombin Receptor
- Thrombocyte
- Thrombospondin
- Thymidine Kinase 1
- Thyroglobulin
- TIA-1
- TIAM2
- Tie1
- Tie2 (pY1102)
- Tie2 (pY992)
- TIF1γ Phospho (Ser473)
- TIGIT
- Tim1
- Tim2
- Tim3
- Tim3 Fc Fusion Protein
- Tim4
- Tim50
- Timeless
- TIMP1
- TIMP2
- TIP49A
- TIRAP
- TIS11b
- TL1A
- TLK1
- TLR11
- TLR12
- CD285
- TLR7
- TLR8
- TMEFF2
- TMPS2
- TMSA
- TMTSP
- TNAP
- TNAP3
- TNF-α
- TNF-β
- TNFR Related Protein
- TNPO3
- Tollip
- TOMM20
- TOMM22
- TOP1
- TOP2A
- TOP2B
- TORC2
- Torsin A
- TOX
- TPH1
- TPPP
- TPTE
- TR11B
- TRA-1-60
- TRA-1-60R
- TRA-1-81
- TRA-2-49
- TRA-2-54
- TRADD
- TRAF2
- TRAF4
- TRAF5
- TRAF6
- TRAM2
- Transferrin
- Transglutaminase
- Transglutaminase2
- Transketolase
- TRAP1
- TRAPPC2
- TRAPα
- Trem-like 2
- Trem-like 4
- TRIB2
- TRIB3
- TRIM
- TRIM25
- TRIM29
- TRK
- TrkA
- TrkC TABLE 8-continued Cell surface markers for use with the hydrogel particles described herein.

Trop2
Tropomyosin 1
TROY
TRPC6
TRPM2
TRPM8
TRX1
*Trypanosoma brucei* Major Lysosomal Protein
*Trypanosoma brucei* procyclin (EP)
*Trypanosoma congolense* procyclin
*Trypanosoma cruzi* LPG
TSC2 Phospho (Ser664)
TSC2 Phospho (Thr1462)
TSG101
TSHR
TSLP
TSLP Receptor
TSPO
TTF1
Tubb3
Tuberin
Tubulin α
Tubulin α 1B
Tubulin α 4a
Tubulin α 3E
Tubulin α 8
Tubulin β
Tubulin β class III
Tubulin β 4
Tubulin β 3
tumor antigens of epithelial origin
Twist2
TXNIP
TYK2
TYMS
Tyro3
Tyrosinase
Tyrosine Hydroxylase
UACA
UBA52
UBC9
UBE2
UBE2L3
UBE2L6
UBE2M
UBE2N
UBF
UBF1
Ubiquitin
UBK63
UCH37
UCK
UCP2
UCP3
UFM1
ULBP1
ULBP2
ULBP4
ULK3
UNC5A
UNC5B
UNG
uPA
UQCRC1
UQCRC2
Urm1
URP2
USF1
USP11
USP13
USP22
USP28
USP7
UTF1
V5 tag
VAMP5/8
VAP1

TABLE 8-continued

Cell surface markers for use with the hydrogel particles described herein.

VASA
VASP
VAV1
VAV2
VAV3
VDAC1
VEGF
VEGF-120
VEGF-A
VEGF-R1
VELIS-3
VGLU1
Villin
Vimentin
Vinculin
Viperin
VIPR1
Vitamin D Binding protein
Vitamin D Receptor
Vitronectin
VMAT2
vMyb/cMyb
von Willebrands factor
VRK1
VSV-G tag
WAPL
WASP
WC14
WC15
WCD44
WIP (pS488)
WNT1
WNT16
WNT2
WNT5B
WNT6
WSTF
WWOX
Xanthine Oxidase
XBP1
XBP1 (COOH terminus)
XBPs
XCL1
XIAP
XPC
XPNPEP3
XRCC2
XTP4
YAP1
YB1
YES1
YY1
ZAP-70
ZAP-70 (pY292)
ZAP-70 (pY319)
ZAP-70 (pY319)/Syk (pY352)
ZBP-1
ZIPK
ZO-1 (Mid)
ZONAB (Mid)
Zyxin
IL-33R
Globo H
CCL8
Siglec-G
CD307e
CLEC6
Snail1
SMAD1 (pS463/pS465)/SMAD8 (pS465/pS467)
SMAD2 (pS465/pS467)/SMAD3 (pS423/pS425)
GSK-3β (pY216)
NKX6.1
FAK (pY397)
Btk (pY223)/Itk (pY180)
ERK3
CD276β
MCP-3

TABLE 8-continued

Cell surface markers for use with the hydrogel particles described herein.

| |
|---|
| FcAμR |
| CD238 |
| beta2 Microglobulin [b, c] |
| Nucleostemin |
| GPR-49 (Central LRR) |
| GPR-49 (N-Terminal) |
| Phospholipase C γ4 |
| coilin |
| HNF1β |
| Trinitrophenal |
| Annexin VII |
| CD301a |
| CD301b |
| mTOR (pS2448) |
| PI16 |
| MSC (W5C5) |
| LAMP5 |
| GPR-19 |
| FPRL2 |
| CXCL5 |
| PAR2 |
| PDGF-Rα |
| ULBP6 |
| ULBP2/5/6 |
| IL-17B Receptor |
| ULBP3 |
| Arginase 1 |
| Alkaline Phosphatase |
| ULBP3 |
| TrkB |
| Osteocalcin |
| IL-22Rα1 |
| APJ |
| IFN-α/β Receptor Subunit 2 |
| FGFR3 |
| SR-A1 |
| Rae-1 (pan) |
| CXCL12 |
| TREM2 |
| Brachyury |
| CLEC5A |
| Integrin α7 |
| Mer |
| XCR1 |
| AML2 |
| von Willebrands factor A2 |
| MMP7 |
| GLP-1R |
| FR1 |
| IL-1RAcP |
| Claudin-6 |
| Leptin Receptor |
| Caherin 6 |
| IL-1R type II |
| Nectin4 |
| Delta like protein 3 |
| ChemR23 |
| GPR-39 |
| CD158b2 |
| IL-10Rα |
| LRIG1 |
| Neuropilin2 |
| IL-10Rβ |
| IL-18Rβ |
| GPR-44 |
| Eph Receptor B2 |
| Glypican3 |
| IFN-γR2 |
| IL-17C Receptor |
| BMPR1B |
| IL-31RA |
| OCIL |
| Frizzled-7 |
| IL-26 |
| GPR-15 |
| PlexinD1 |
| CD158 |
| FPR1 |
| HBEGF |
| Vitamin D3 |
| PlexinB1 |
| Somatostatin Receptor 2 |
| OV-6 |
| CXCL16 |
| Siglec-E |
| EDG5 |
| Ninjurin-1 |
| Integrin α9 |
| MHC Class II (I-Ed/j/k/p/r/u/v) |
| ThB |
| MAP-2 (2a & 2b) |
| IgM μ-chain |
| MHC Class I (H-2b/p) |
| MHC Class I (H-2s/p/q/d/u/r) |
| MHC Class I (H-2s/f) |
| CDw60 |
| Bad Phospho (Ser112) |
| Caspase 3 Cleaved (Asp175) |
| Chk1 Phospho (Ser345) |
| Chk2 Phospho (Thr68) |
| Cyclin D1 Phospho (Thr286) |
| cFos Phospho (Ser32) |
| FosB |
| GSK-3β (pSer9) |
| Histone H3 Acetylated (Lys9) |
| HS1 Phospho (Tyr397) |
| Hsp27 Phospho (Ser82) |
| ID3 |
| CD221β |
| Phospho-IRAK4 (Thr345/Ser346) |
| Phospho-cJun (Ser73) |
| S6 (pS240/pS244) |
| Syk (pY525/pY526) |
| C23 |
| Hemoglobin β |
| CD221α |
| p27 |
| cJun Phospho (Ser63) |
| PPARγ |
| ENPP1 |
| PILRα |
| PILRβ |
| Twist1 |
| Cadherin M |
| CD302 |
| CD66d |
| CLEC14A |
| CD242 |
| Syndecan2 |
| IL-32α |
| CDO |
| Cryptic |
| Endothelin B Receptor |
| FR3 |
| IGSF3 |
| CD85f |
| Matriptase |
| MCEMP1 |
| mGluR4 |
| Stabilin1 |
| Stabilin2 |
| Cadherin 13 |
| GPR-109A |
| TSPAN8 |
| Reg1A |
| Cadherin 12 |
| ECE1 |
| FABP5 |
| IGSF4C |
| Trem-like 1 |
| Activin A Receptor Type IIA |
| ALK7 |
| BCAM |
| BLAME |

TABLE 8-continued

Cell surface markers for use with the hydrogel particles described herein.

CEACAM4
Claudin-3
CLP24
CRHR1
DC-STAMP
Eph Receptor B3
FATP4
FcRL1
FcRL2
FcRL3
FSH-R
Gi24
Histamine H1 Receptor
NeuSGc
Lin28A
IL-33Rα
ATM (pSer1981)
Integrin α8
Integrin β7
Integrin β8
CD158k
KOR
CD85i
LRIG3
LRP4
MMP16
MS4A4A
NAALADase-like 2
Neuropeptide Y receptor type 1
Oncostatin M Receptor β
MS4A3
PEAR1
PEDF Receptor
PlexinA4
Protocadherin1
ROBO2
ROBO4
EDG8
Scavenger receptor A5
Semaphorin 4A
Semaphorin 4B
Semaphorin 6A
Siglec-16
Somatostatin Receptor 3
STING
GPBAR1
TM4SF4
TMEM87A
TSPAN2
VEGF-R1, 2, 3
ADAM15
Calreticulin2
Complement Factor H-related 4
CXCL6
CD158a/h/b2/f/g
Ea52-68 peptide bound to I-Ab
HLA-Bw4
ATF1 Phospho (Ser63)
Epiregulin
FATP1
Fibromodulin
Furin
Galanin
IL-11
CD306
MFG-E8
MINA
Oct4A
OLIG1, 2, 3
Oncostatin M
Semaphorin 3E
Slug
SOX3
STYK1
LTBP1
TIMP3
VAP-B TABLE 8-continued Cell surface markers for use with the hydrogel particles described herein.

WNT9a
5HT2C
AATK
ACLP
ADAMTS15
alpha 1B Adrenoreceptor
APLP1
Fluorescein/Oregon Green
RXR-β
L3MBTL3
CCL1
PRDM4
ACTH
PDZ binding kinase
HuC/HuD neuronal protein
TDRD3
EP300
Carbonic Anhydrase VI
Cholecystokinin A Receptor
CCL23
CD1e
Chondrolectin
Chordin-Like 2
Claudin-10b
Claudin-11
Claudin-12
Claudin-17
CLEC2A
Coagulation Factor VII
CXCL1/2/3
DDR2
DPCR1
Dipeptidyl peptidase 6
Epithelial membrane protein 3
Endoglycan
Calgranulin C
FATP2
FATP5
FcRLB
GLP-2R
GLUT3
Glypican6
GPR-22
GPR-37
GPR-37L1
INSRR
LINGO1
LINGO2
mGluR2
mGluR7
MMP25
Neuromedin B Receptor
NRAGE
Osteoactivin
Porimin
Prokineticin Receptor 1
Prominin2
Semaphorin 3A
SLAP-130
Somatostatin Receptor 5
SCARF1
STAMP2
TAFA3
TAFA4
TM4SF18
Tuberous Sclerosis 1
TCF8
CMG2
IL-17D Receptor
Macrophage Stimulating Protein Receptor
Siglec-11
Syndecan3
TGF-βR3
CD85e
SOX7
Activin A Receptor Type IA
Carbohydrate Sulfotransferase 15

TABLE 8-continued

Cell surface markers for use with the hydrogel particles described herein.

CD300b
CELSR3
Coagulation Factor II
DC-SCRIPT
DSCAM-L1
FLRT1
Frizzled-6
Glypican1
IGSF4B
IL-1R9
BAZ2B
BRD4
Kell
Kremen2
LAX1
CD85c
MIF
Neprilysin2
OBCAM
PlexinC1
RGM-B
Wilms' ™ Tumor protein 1
Xg
DCBLD2
ASAM
Desmocollin1
Frizzled-3
MMP24
TOR
WNT3a
Glypican5
Jagged1/Jagged2
Pax3
CELSR2
Cyclin D1/D2
PlexinA2
TAFA5
FR4
CD315
NKG2I
RAMP2
TNFRH3
Biotin
GPVI
MS4A4B
PIR-B
Semaphorin 4F
IL-1F6
CD39L3
Contactin 3
CLEC4B
MC3R
PGRP-L
PLET1
ADAM9
AMIGO3
CD99-L2
Eph Receptor A5
Ephrin B2
CD316
Kremen1
Eph Receptor B1
PlexinB3
DMBT1
FcRn
LIMPII
MUCDHL
Patched1
SLC39A4
IGSF4A
PRAT4B
HHV8-ORF74
4E-BP1 Phospho (Thr36/45)
4E-BP1 Phospho (Thr69)
DCAR1
Von Hippel-Lindau
Isotype Control TABLE 8-continued Cell surface markers for use with the hydrogel particles described herein.

Granzyme M
REA Isotype Control
CD300LG
MR1
CD327
B7-H6
CLEC4G
BATF3
IL-38
Monocarboxylic Acid Transporter 1
MC5R
TCF7
TM4SF1
GPR-49 (CRL Region)
CD156a
ADAM33
ADAMTS13
CCL16
CXCL17
Deltex1
FBXO15
GPR34
GPRC5A
Proinsulin
JAK1
MEP1A
Hypocretin receptor 2
p70S6K
RAE-1μ
STRA6
FcγRIIA
Insulin R/IGF-I R Heterotetramer
SPARCL1
Spi-B
TRAM
Carboxypeptidase E
Islet Cell Autoantigen 1
Patched2
ST8SIA2
AML1 (pS249)
AMPKα1 (pS182)
BRF1/2
Histone H3 Phospho (Thr11)
MEK1 (pT286)
MMP16
MNK Phospho (T197/T202)
NUMB
Hsp27 Phospho (Ser78)
PKCδ (pT538)
SIRT1 (pS47)
ZAP-70 (pY493)
ZAP-70 (pY315/pY319)
sRAGE
mCherry
PI 3 Kinase regulatroy subunit α
TIMP4
SRC
ZAP-70 (pT493)
TSC2 Phospho (S939)
RagC
SHIP2
MKK4 (pS257)
CD79a (pY182)
TRAF1
EVI1
SRC3
SOX11
IL-17F homodimer
CCRL1
FOXP2
IFNAR2
REA Control
CD228
Muc-13
P2X7R
Btk (pY223/Itk (pY180)
CD248

TABLE 8-continued

Cell surface markers for use with the
hydrogel particles described herein.

GILT
Recoverin
Cardiac Troponin I
PTF1Î±
NKX2.2
HLA-B7/B27
Myosin light chain 2a
Myosin light chain 2v
Epithelial Antigen
CD79Î ± cy
CD92

In one embodiment, a plurality of hydrogel particles is used to determine the dynamic range and/or sensitivity of detection of a particular cell surface marker or combination thereof on a population of target cells. For example, the population of hydrogel particles can be tuned to have the SSC and/or FSC profile of the target cell, and subpopulations of the hydrogel particle are derivatized with a specific number of copies of a cell surface marker, e.g., a cell surface receptor, or a domain thereof, for example, an epitope binding region thereof. For example, individual subpopulations of hydrogel particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of hydrogel particles are fluorescently stained for the respective cell surface marker and fluorescence is detected for hydrogel particles in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

Hydrogel particles of the disclosure behave similarly to target cells in procedures such as staining and analysis by flow cytometry or FACS. For example, in one embodiment, a hydrogel particle has one or more optical properties substantially similar to one of the cell types set forth in Table 1, Table 2 or Table 3.

In some embodiments, a target cell is an immune cell. Non-limiting examples of immune cells include B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor infiltrating (TIL) cells, gene modified immune cells including hybridomas, drug modified immune cells, and derivatives, precursors or progenitors of any of the cell types listed herein.

In some embodiments, a target cell encompasses all cells of a particular class of cell with shared properties. For example, a target cell can be a lymphocyte, including NK cells, T cells, and B cells. A target cell can be an activated lymphocyte.

In some embodiments, a target cell is a primary cell, cultured cell, established cell, normal cell, transformed cell, infected cell, stably transfected cell, transiently transfected cell, proliferating cell, or terminally differentiated cells.

In one embodiment, a target cell is a primary neuronal cell. A variety of neurons can be target cells. As non-limiting examples, a target cell can be a primary neuron; established neuron; transformed neuron; stably transfected neuron; or motor or sensory neuron.

In other embodiments, a target cell is selected from the group consisting of: primary lymphocytes, monocytes, and granulocytes.

A target cell can be virtually any type of cell, including prokaryotic and eukaryotic cells.

Suitable prokaryotic target cells include, but are not limited to, bacteria such as *E. coli*, various *Bacillus* species, and the extremophile bacteria such as thermophiles.

Suitable eukaryotic target cells include, but are not limited to, fungi such as yeast and filamentous fungi, including species of *Saccharomyces, Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include those cell types implicated in a wide variety of disease conditions, even while in a non-diseased state. Accordingly, suitable eukaryotic cell types include, but are not limited to, tumor cells of all types (e.g., melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as hematopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. In certain embodiments, the cells are primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, a target cell is a tumor microvesicle or tumor macrovesicle. Tumor microvesicles, also known as tumor-secreted microvesicles or tumor-secreted exosomes, can be found in circulating blood and may have immune-suppressive activities. Tumor microvesicles typically range in size from 30-200 nm in diameter. Larger tumor micro vesicles may be referred to as tumor macro vesicles, and can range in size from 3-10 μm in diameter.

The hydrogel particles described herein can be employed in any flow cytometer known to those of ordinary skill in the art. For example, one or more of the flow cytometers provided in Table 9 below are amenable for use with the hydrogels and assays described herein.

TABLE 9

Instruments for use with embodiments described herein

| Instrument | Manufacturer |
|---|---|
| MACSQuant ® Analyzer 10 | Miltenyi |
| MACSQuant ® VYB | Miltenyi |
| BD FACSCalibur ™ | BD Biosciences |
| BD FACSCanto ™ High Throughput Sampler | BD Biosciences |
| BD FACSCanto II | BD Biosciences |
| BD FACSCanto ™ | BD Biosciences |
| BD FACSCount ™ | BD Biosciences |
| BD Accuri ™ C6 | BD Biosciences |
| BD LSRFortessa ™ X-20 | BD Biosciences |
| BD FACSCanto ™ II | BD Biosciences |
| BD LSR II | BD Biosciences |
| BD LSRFortessa ™ | BD Biosciences |
| BD FACSVerse ™ | BD Biosciences |
| BD FACSAria ™ Fusion | BD Biosciences |
| BD FACSAria ™ | BD Biosciences |
| BD FACSAria ™ III | BD Biosciences |
| BD FACSJazz ™ | BD Biosciences |
| BD Influx ™ | BD Biosciences |
| Fortessa X50. | BD Biosciences |
| FlowSight Flow Cytometer | Millipore |
| Guava easyCyte 6-2L Benchtop Flow Cytometer | Millipore |
| guava easyCyte 5HT Benchtop Flow Cytometer | Millipore |
| guava easyCyte 8 Benchtop Flow Cytometer | Millipore |
| guava easyCyte 5 Benchtop Flow Cytometer | Millipore |
| guava easyCyte 8HT Benchtop Flow Cytometer | Millipore |
| guava easyCyte 6HT-2L Benchtop Flow Cytometer | Millipore |
| ImageStreamX Mark II Imaging Flow Cytometer | Millipore |
| Muse Cell Analyzer | Millipore |
| guava easyCyte 12HT Benchtop Flow Cytometer | Millipore |
| guava easyCyte 12 Benchtop Flow Cytometer | Millipore |
| S3e ™ Cell Sorter | Bio-Rad |
| S3 ™ Cell Sorter | Bio-Rad |
| Avalon Cell Sorter | Bio-Rad/Propel Labs |
| CytoFLEX | Beckman Coulter |
| FP 1000 Cell Preparation System | Beckman Coulter |
| Vi-CELL ® XR Cell Viability Analyzer | Beckman Coulter |
| FC 500 Series | Beckman Coulter |
| MoFlo ® Astrios ™ | Beckman Coulter |
| Coulter Epics XL ™ and XL-MCL ™ | Beckman Coulter |
| Gallios ™ | Beckman Coulter |
| CyAn ™ ADP Analyzer | Beckman Coulter |
| Attune ™ Acoustic Focusing Cytometer | Life Technologies |
| Attune ® NxT Acoustic Focusing Cytometer | Life Technologies |
| EVOS | Life Technologies |
| Countess II FL | Life Technologies |
| EC800 Cell Analyzer | Sony |
| SH800 Cell Sorter | Sony |
| SP6800 Spectral Analyzer | Sony |
| SY3200 Cell Sorter | Sony |
| A50-Micro' | Apogee Flow Systems |
| A50-Universal | Apogee Flow Systems |
| Auto40 | Apogee Flow Systems |
| FlowSight | Amnis |
| ImageStream$^x$ Mark II | Amnis |
| JSAN | Bay Bioscience |
| CytoSense | CytoBuoy |
| CytoSub | CytoBuoy |
| CytoSense | CytoBuoy |
| CytoBuoy | CytoBuoy |
| Cytonome Viva ™ G1 | CYTONOME |
| GigaSort ™ | CYTONOME |
| Hydris | CYTONOME |
| Agilent 2100 Bioanalyzer | Agilent Technologies |
| NovoCyte | ACEA Biosciences |
| CyFlow ® Space | Partec technology |
| CyFlow ® Cube 8 | Partec technology |
| CyFlow ® Cube 6 | Partec technology |
| CyFlow ® Ploidy Analyser | Partec technology |
| CyFlow ® Counter | Partec technology |
| CyFlow ® miniPOC | Partec technology |
| CyFlow ® SL | Partec technology |
| CyFlow ® Sorter | Partec technology |
| CyFlow ® CCA | Partec technology |
| CyFlow ® Oenolyser | Partec technology |
| NucleoCounter ® NC-3000 ™ | Chemometec |
| NucleoCounter ® NC-250 ™ | Chemometec |
| NucleoCounter ® NC-200 ™ - High Precision Cell Counter | Chemometec |
| HPC-100 Portable Flow Cytometer | Cronus Technologies Ltd |
| Cytell Cell Imaging System | GE Healthcare |
| MAGPIX | Luminex |
| Luminex ® 100/200 ™ System | Luminex |
| FLEXMAP 3D ® | Luminex |
| ImageXpress ® Velos Laser Scanning Cytometer | molecular devices |
| ClonePix ™ 2 | molecular devices |
| SpectraMax ® i3 | molecular devices |
| AQ1 Discrete Analyzer | SEAL Analytical Ltd. |
| AQ2 Discrete Analyzer | SEAL Analytical Ltd. |
| AQ400 Discrete Analyzer | SEAL Analytical Ltd. |
| AQUA 900 | SEAL Analytical Ltd. |
| AA3 HR AutoAnalyzer | SEAL Analytical Ltd. |
| AA1 AutoAnalyzer | SEAL Analytical Ltd. |
| QuAAtro39 | SEAL Analytical Ltd. |
| Infralyzer 2000 | SEAL Analytical Ltd. |
| Technicon AutoAnalyzer II (AAII) | SEAL Analytical Ltd. |
| Technicon/Bran + Luebbe TrAAcs 800-2000 | SEAL Analytical Ltd. |
| Bran + Luebbe FIA Analyzer | SEAL Analytical Ltd. |
| BioSorter ® Large Particle Flow Cytometer | Union Biometrica, Inc. |
| COPAS ™ Large Particle Flow Cytometers | Union Biometrica, Inc. |
| Cellometer Mini Cell Counter | Nexcelom |
| Cellometer Auto T4 Cell Viability Counter | Nexcelom |
| Cellometer Auto X4 Cell Viability Counter | Nexcelom |
| Cellometer Auto 1000 Cell Viability Counter | Nexcelom |
| Cellometer Auto 2000 Cell Viability Counter | Nexcelom |
| Cellometer Vision CBA | Nexcelom |
| Celigo S | Nexcelom |
| NovoCyte ™ 1000 | ACEA |
| NovoCyte ™ 2000 | ACEA |
| NovoCyte ™ 2060 | ACEA |
| NovoCyte ™ 3000 | ACEA |
| HPC-100 | Handyem |
| S1000EXi | Stratedigm |
| SE520Xi | Stratedigm |
| Sysmex ® DI-60 | Sysmex |
| CellaVision ® DM96 | Sysmex |
| CellaVision ® DM1200 | Sysmex |
| Cytation | BioTek |
| EasyCell Assistant | Medica |
| IN Cell Analyzer | GE Healthcare |
| Fluorish List | |
| Big Blue | BD Biosciences |
| Kermit | Miltenyi |
| ac6 | BD Biosciences |
| srDAs | BD Biosciences |
| a | BD Biosciences |
| FACSCanto II Immunology Test Cyt | BD Biosciences |
| milt | Miltenyi |
| ac | BD Biosciences |
| ietest | BD Biosciences |
| Curiel's Aria | BD Biosciences |

TABLE 9-continued

Instruments for use with embodiments described herein

| Instrument | Manufacturer |
|---|---|
| AttuneÂ ® Acoustic Focusing Cytometer Blue/Violet | Life Technologies |
| Medawar LSRII | BD Biosciences |
| Medawar Calibur | BD Biosciences |
| FACSAria INER | BD Biosciences |
| Attune R/A | Life Technologies |
| Fortessa | BD Biosciences |
| Aria | BD Biosciences |
| SORTER | BD Biosciences |
| Cyan | Beckman Coulter |
| LSR II | BD Biosciences |
| ARIA | BD Biosciences |
| Canto II | BD Biosciences |
| F09 - LSR Fortessa 1 | BD Biosciences |
| "The Hoff" | BD Biosciences |
| 6th Floor Hess Fortessa A | BD Biosciences |
| Cerebro BDFACSAriaII | BD Biosciences |
| Mystique BDFACSAriaII | BD Biosciences |
| Godzilla BDFACSAriaII | BD Biosciences |
| Wolverine BDFACSAriaII | BD Biosciences |
| Megatron BDFACSAriaII | BD Biosciences |
| Megatron BDFACSAriaII | BD Biosciences |
| Fortessa B | BD Biosciences |
| 6 colour Canto II | BD Biosciences |
| 10 colour LSR II | BD Biosciences |
| 4 laser 13 colour Influx sorter | BD Biosciences |
| 14 colour X20 | BD Biosciences |
| SORP | BD Biosciences |
| FACSAria INER | BD Biosciences |
| LSR561 | BD Biosciences |
| Fortessa FCF UZH | BD Biosciences |
| LSR 2 B | BD Biosciences |
| LSRII-C | BD Biosciences |
| Cal 3 | BD Biosciences |
| Aria II A | BD Biosciences |
| LSR 16 | BD Biosciences |
| LSB Fortessa | BD Biosciences |
| IMMUN LSRII | BD Biosciences |
| IRC | BD Biosciences |
| UV LSR | BD Biosciences |
| 5 Laser Aria | BD Biosciences |
| Curiel's LSR II | BD Biosciences |
| LSR Fortessa | BD Biosciences |
| Mauzeroll Aria | BD Biosciences |
| Frenette | BD Biosciences |
| Fallon | Beckman Coulter |
| Galios | Beckman Coulter |
| LSRIIFortessa | BD Biosciences |
| FACSCanto II CLSB | BD Biosciences |
| LSR II SC | BD Biosciences |
| UNCA Fortessa | BD Biosciences |
| VERSE | BD Biosciences |
| ARIAII | BD Biosciences |
| ARIAIII | BD Biosciences |
| F09 - BD LSRFortessa | BD Biosciences |
| HMRI FACSCanto II A | BD Biosciences |
| HMRI FACSCantoII B (HTS) | BD Biosciences |
| HMRI Aria III | BD Biosciences |
| L2 | BD Biosciences |
| UoN Canto | BD Biosciences |
| LSRII M902 | BD Biosciences |
| Fortessa 1 | BD Biosciences |
| F05 - FACSAria | BD Biosciences |
| F02 - FACSAria III | BD Biosciences |
| F10 - BD FACSAria III | BD Biosciences |
| F03 - Guava | Millipore |
| Aria Blue 11 Color | BD Biosciences |
| Aria Red | BD Biosciences |
| Aria Orange | BD Biosciences |
| Aria Cyan | BD Biosciences |
| Aria Emerald | BD Biosciences |
| Aria Silver BSL3 | BD Biosciences |
| LSR Fortessa | BD Biosciences |
| LSR II Bldg 4 | BD Biosciences |
| LSR Fortessa bldg 4 | BD Biosciences |
| CANTO II Bldg 50 | BD Biosciences |
| 4 Laser LSR II | BD Biosciences |
| 5 Laser LSR II | BD Biosciences |
| FACSArray BL-2 | BD Biosciences |
| FACSCalibur | BD Biosciences |
| DUAL for long term studies | BD Biosciences |
| MoFlo 1095 Production only | Beckman Coulter |
| BL-2 FACSAria III sorter | BD Biosciences |
| Astrios BL-2 sorter | Beckman Coulter |
| Tessy | BD Biosciences |
| LSR II-1 | BD Biosciences |
| Fortessa | BD Biosciences |
| 4 laser AriaIII | BD Biosciences |
| LSRFortessa | BD Biosciences |
| UoN FACSAria II cell sorter | BD Biosciences |
| Door | Beckman Coulter |
| Fortessa | BD Biosciences |
| WCI - FACSAria I | BD Biosciences |
| LSRII Karp8 | BD Biosciences |
| Karp 8 | BD Biosciences |
| Canto | BD Biosciences |
| Aria sorter | BD Biosciences |
| DI lab | BD Biosciences |
| DI FACSAria | BD Biosciences |
| Constance | BD Biosciences |
| DI FACSAria III | BD Biosciences |
| WCI_FACS Canto | BD Biosciences |
| MACSQuant 10 | Miltenyi |
| VAMC Memphis LSR | BD Biosciences |
| VAMC Memphis S3 | Bio-Rad |
| ARIA INER | BD Biosciences |
| Uhura | BD Biosciences |
| Kirk | BD Biosciences |
| Data | Millipore |
| Spock | BD Biosciences |
| McCoy | BD Biosciences |

EXAMPLES

The present invention is further illustrated by reference to the following Examples. However, it should be noted that these Examples, like the embodiments described above, are illustrative and are not to be construed as restricting the scope of the invention in any way.

Example 1: Generation of Hydrogel Particles

Photomasks for UV lithography were sourced from CADart Services Inc. and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald J C, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker (N,N'-bisacrylamide, 0.05-1% w/v), an accelerator, and ammonium persulfate (1% w/v) was used. An accelerator, (N,N,N',N'tetramethylethylenediamine (2% vol %) was added to the oil-phase in order to trigger hydrogel particle polymerization after droplet formation.

Several co-monomers were added to the basic gel formulation to add functionality. Allyl-amine provided primary amine groups for secondary labeling after gel formation. We modulated forward scatter by adjusting the refractive index of the gel by adding co-monomers allyl acrylate and allyl methacrylate. Side scattering of the droplets was tuned by adding a colloidal suspension of silica nanoparticles and/or PMMA (poly(methyl methacrylate)) particles (~100 nm) to the central aqueous phase prior to polymerization.

Stoichiometric multiplexing of the hydrogel particles was achieved by utilizing co-monomers containing chemically orthogonal side groups (amine, carboxyl, maleimide, epoxide, alkyne, etc.) for secondary labeling.

Droplets were formed at an average rate of 5 kHz and were collected in the fluorocarbon oil phase. Polymerization was completed at 50° C. for 30 minutes, and the resulting hydrogel particles were washed from the oil into an aqueous solution.

Example 2: Generation and Visualization of 12 11 m Hydrogel Particles

Figure 3:
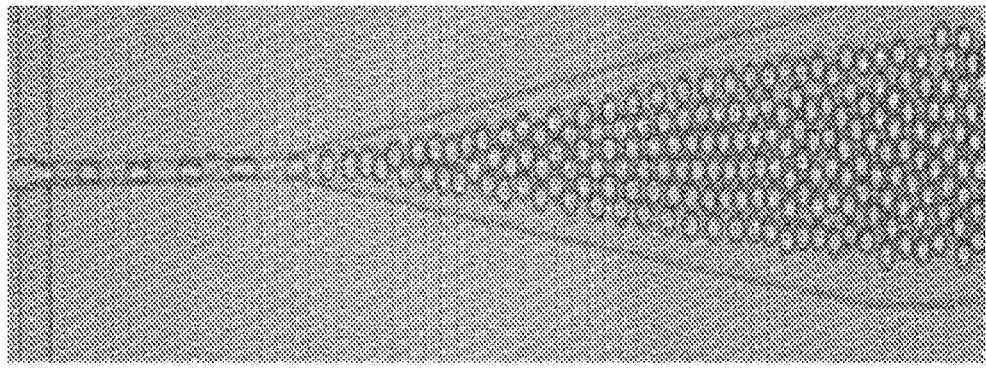
FIG. 3 provides brightfield and fluorescent images of labeled hydrogel particles of the disclosure.
Figure 3:
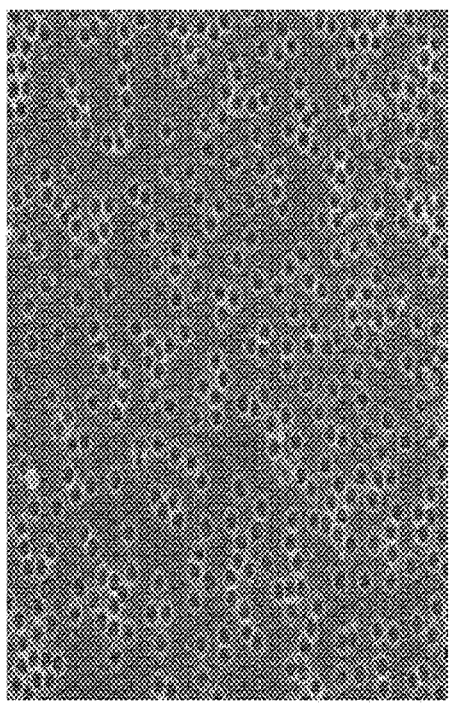
Figure 3:

Water containing 5% acrylamide, 0.25% bisacrylamide, 0.05% allyl amine, and 0.1% ammonium persulfate was flowed through a center channel and focused by oil containing 0.1% TEMED through a 10 micron nozzle to produce 10 µm hydrogel particles, shown in FIG. 3A. Following polymerization, the particles were washed in water, shown in FIG. 3B, and conjugated to dyes of interest. The fluorescent hydrogel particles were visualized with fluorescence microscopy, shown in FIG. 3C.

Example 3: Multidimensional Tuning of Hydrogel Particle Optical Properties

Figure 4:
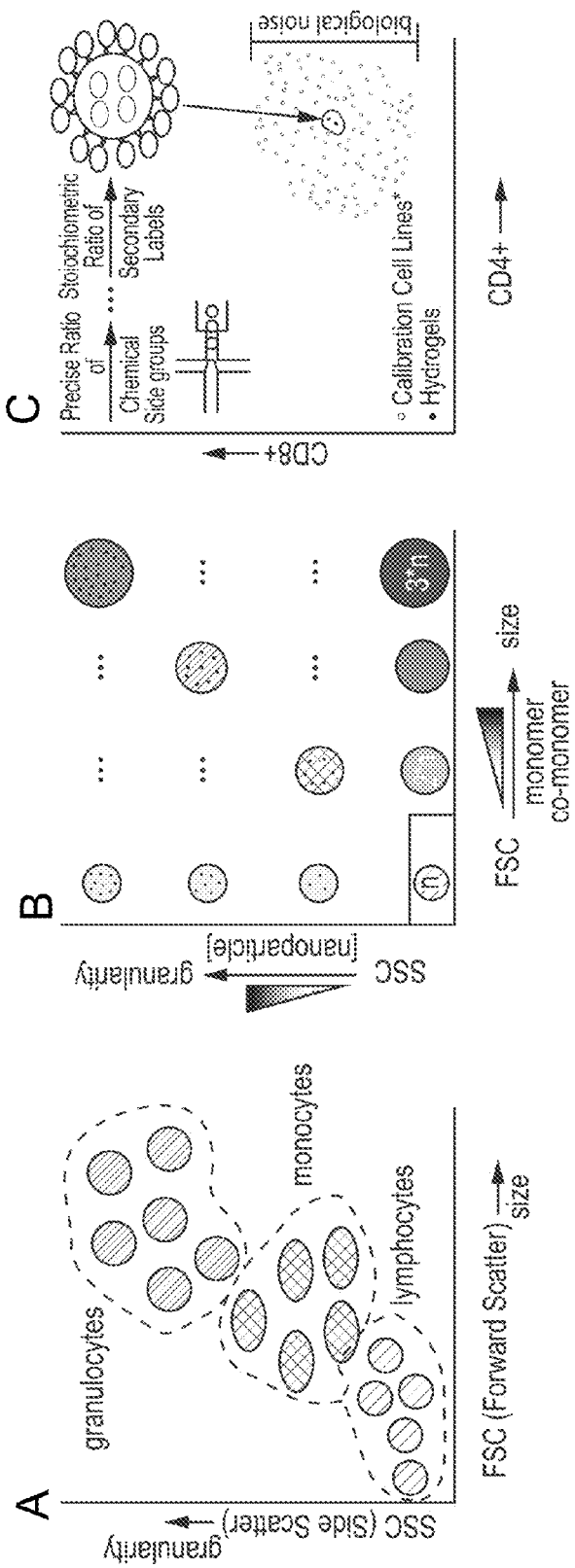
FIG. 4 illustrates the use of hydrogel particles of the disclosure as calibrants for cell types displaying a variety of optical scattering properties.

As depicted in FIG. 4, hydrogel particles are tuned in multiple dimensions to match specific cell types unlike polystyrene beads. Cells are deconvolved using combinations of optical parameters such as FSC and SSC (FIG. 4A) or secondary markers. Hydrogel particles are tuned to match the SSC and FSC of specific cell types unlike polystyrene beads (brown) which are limited in size (FSC) and side scattering (FIG. 4B). Hydrogel particles are further functionalized with stoichiometrically tuned ratios of specific chemical side-groups and secondary labels allowing the cell type to be precisely matched without suffering from biological noise as fixed cell lines do (FIG. 4C).

Figure 5:
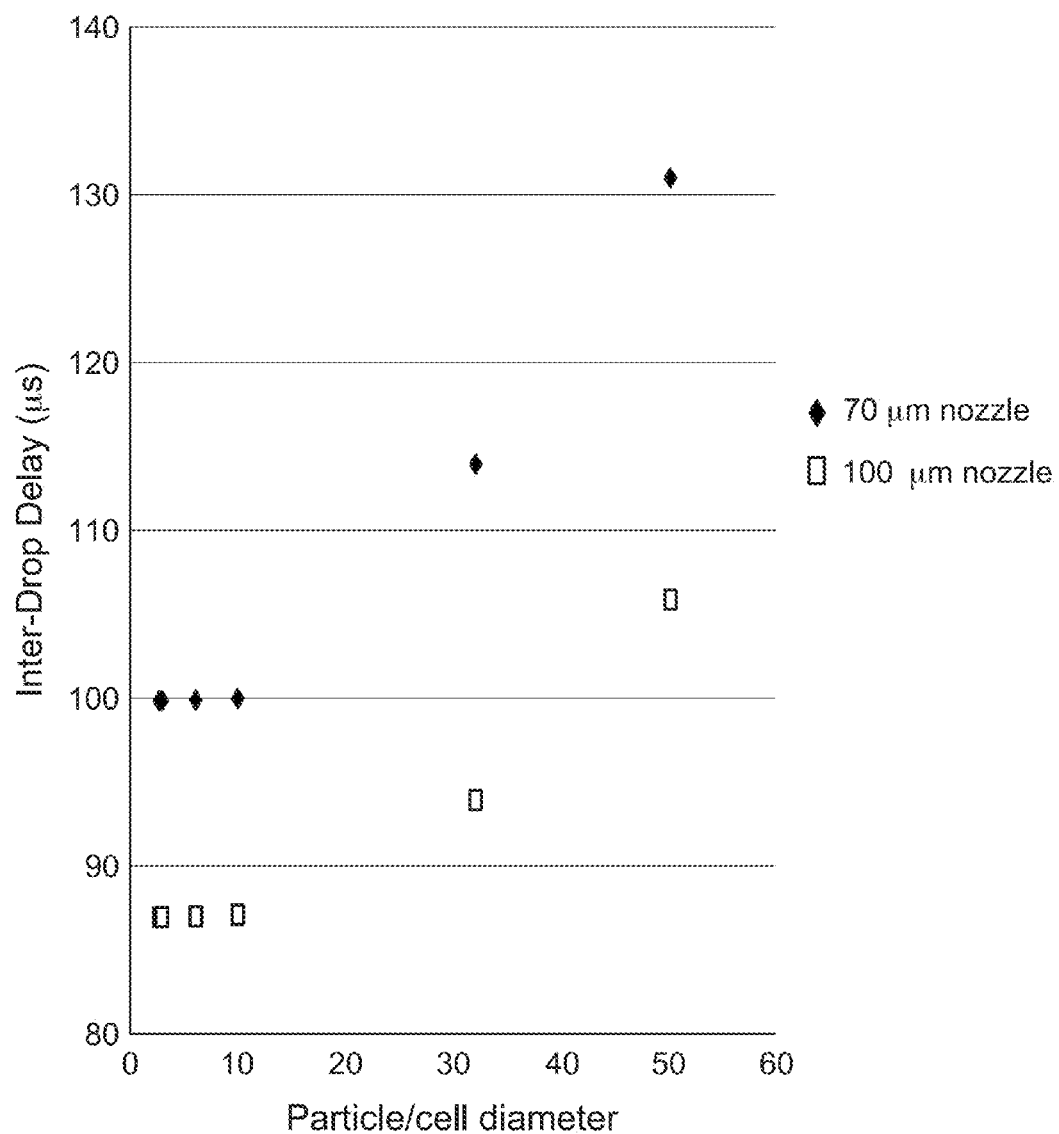
FIG. 5 provides dating showing correlation of inter-drop delay for a flow cytometer with hydrogel particle diameter.

Example 4: Flow Cytometer Delay Time as a Function of Hydrogel Particle Diameter As shown in FIG. 5, the inter-drop delay for a flow cytometer can be precisely correlated to hydrogel particle diameter. Data are shown for hydrogel particles of 3, 6, 10, 32, and 50 µm diameters using flow cytometer nozzle sizes of 70 and 100 µm.

Example 5: Comparison of Hydrogel Particles with Encapsulated DNA to Cells

Figure 6:
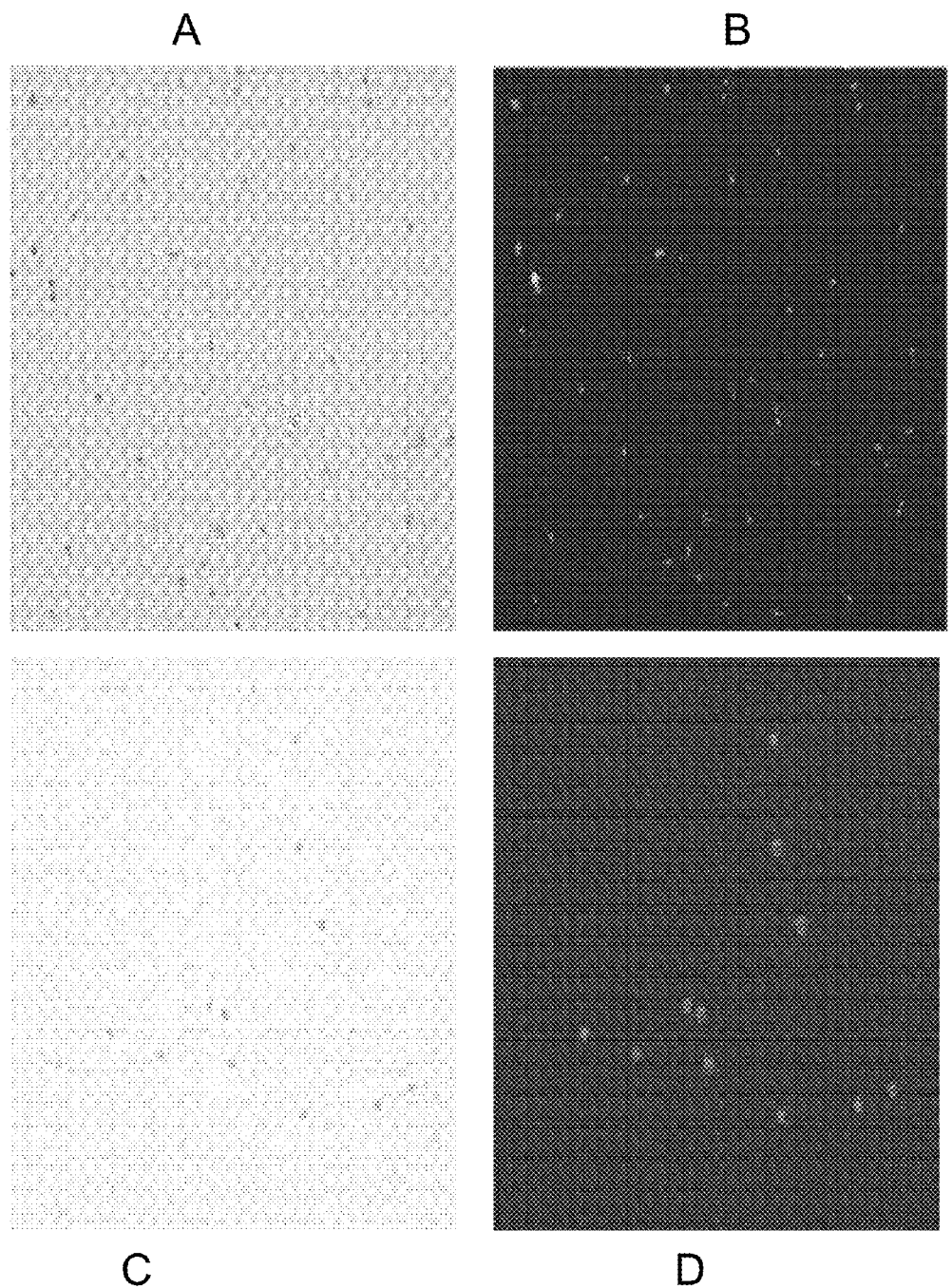
FIG. 6 provides brightfield (6A and 6C) and fluorescent (6B and 6D) images of Chinese Hamster Ovary cells (6A and 6B) and hydrogel particles of the disclosure (6C and 6D).

To form hydrogel particles with encapsulated DNA, 40 µg/mL-1000) µg/mL of reconstituted calf thymus DNA was added to a polymer mix containing 20% 19:1 (acrylamide:bis-acrylamide) and 0.1% allyl amine in water. 0.4% ammoniumpersulfate was added to the mix prior to droplet formation. Hydrogel particles were formed as described in Example 1. Hydrogel particles with 200 µg/mL of encapsulated calf thymus DNA displayed cell-like staining using propidium iodide as visualized using a commercial imaging cytometer and compared to Chinese Hamster Ovary cells stained using the same procedure. Images were obtained using a Nexcelom Cellometer™ (FIG. 6).

Figure 7:
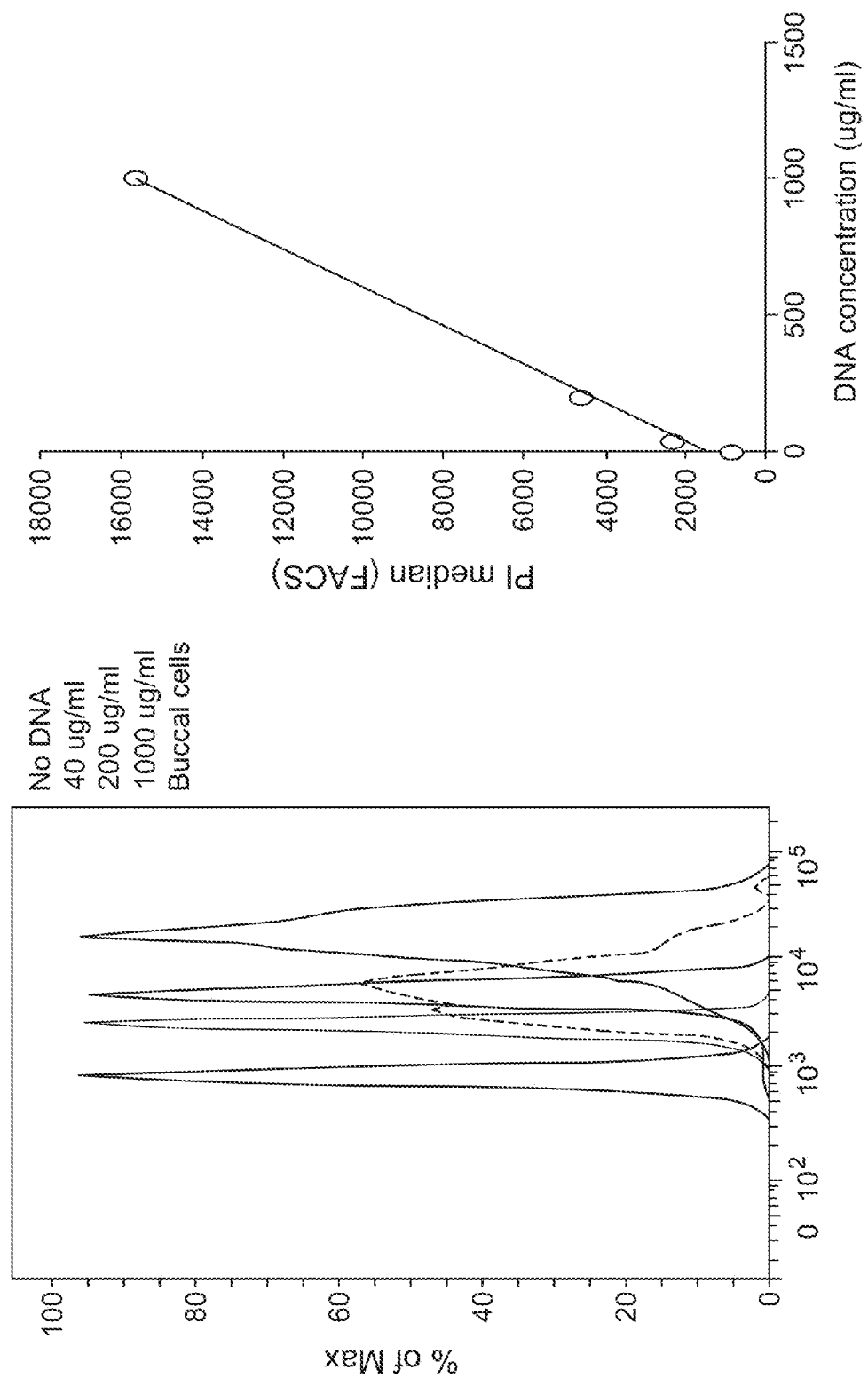
FIG. 7 provides data showing comparison of human buccal cells to hydrogel particles encapsulating different amounts of DNA, as measured by fluorescence-activated cell sorting (FACS).

Cells obtained from a buccal swab were washed in PBS and stained with propidium iodide. In parallel, populations of hydrogel particles containing a range of DNA concentrations were also stained in the same manner. Both the cell and particle suspensions were analyzed on a flow cytometer (488/590 nm excitation/emission). Flow cytometry analysis of cheek cells and the same range of encapsulated DNA particles showed that the particles display a range of cell-like fluorescent properties (FIG. 7, left panel). The intensity of staining shows a linear correlation with the median intensity as measured by flow cytometry (FIG. 7, right panel).

Example 6: Tuning of Hydrogel Particle Side Scattering

Figure 8:
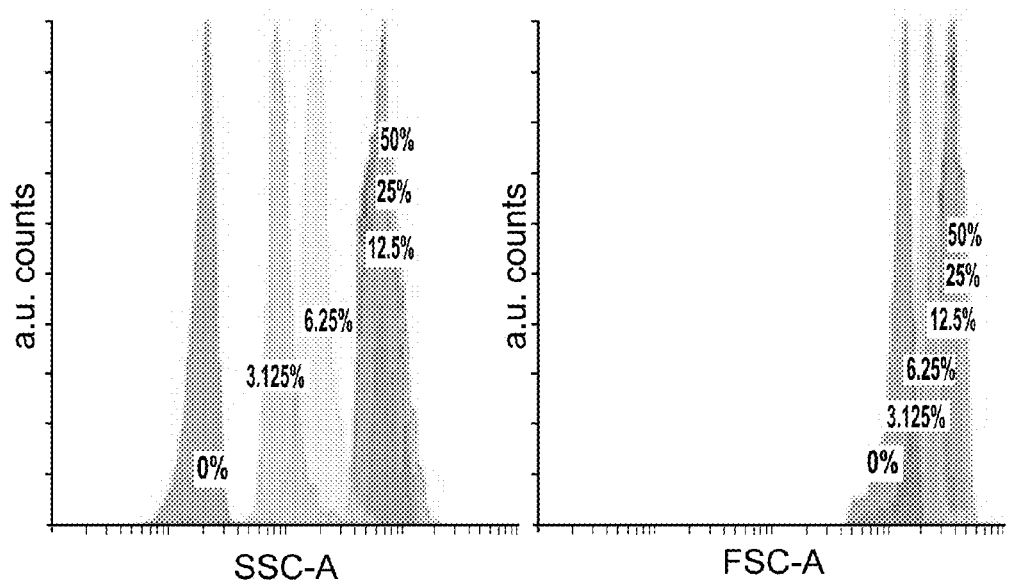
FIG. 8 provides data for hydrogel particles encapsulating nanoparticles at different concentrations, demonstrating tuning of side scattering independent of forward scattering.

Colloidal silica was added at 12.5%, 6.25%, 3.125% and 0% to the aqueous fraction of the polymer mix and hydrogel particles were formed as described in Example 1. Forward and side scattering data were obtained using a flow cytometer. The results showed that side scatter signal (FIG. 8, left panel) increased with higher percentages of encapsulated nanoparticles while forward scatter (FIG. 8, right panel) remained generally unchanged, demonstrating the independent tuning of side scatter and forward scatter.

Example 7: Tuning of Hydrogel Particle Forward Scattering

Figure 9:
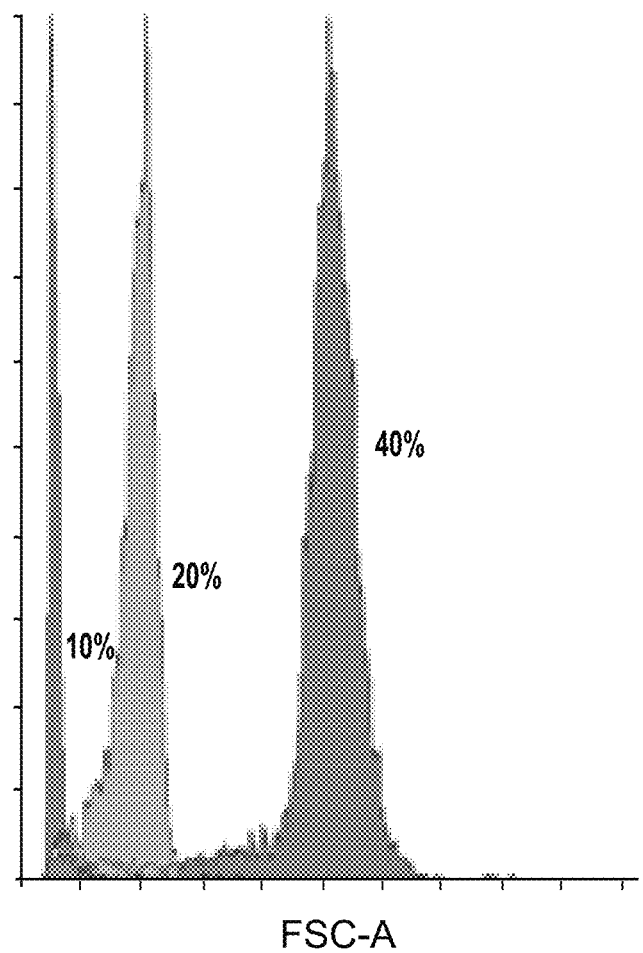
FIG. 9 provides data for hydrogel particles produced with different percentages of polymer, demonstrating tuning of refractive index measured by forward scattering.

In this experiment, the percentage of acrylamide:bis-acrylamide in the hydrogel composition was varied from between 10 and 40% to tune the refractive index of the hydrogel particles as measured by forward scattering in a flow cytometer. As shown in FIG. 9, the forward scattering increased with increasing percentages of acrylamide:bisacrylamide as a fraction of water.

Example 8: Tuning of Hydrogel Particle Optical Properties

An example of tuning hydrogel particles to match optical properties of a desired cell subtype. Co/monomers can be combined with nanoparticles to tune both forward and side scatter properties of the hydrogels using passive optical measurements in a flow cytometer. By combining these properties with chemically labile co-monomers (e.g. allyl amine, acrylic acid), additional fluorophores/proteins/biological side groups can be added and labeled (if desired) in order to match cell subpopulation staining in addition to scattering properties. These are the three primary metric by which cells are identified using flow cytometry. Additional side groups, such as those containing heavy metals, can be used for Cy-TOF (cytometry, time of flight mass spectrometry) calibration for example. Finally, biocompatible material can be encapsulated to mimic subcellular organelle staining.

Example 9: Tuning of Hydrogel Particle Optical Properties

A 50 nm nanoparticle colloidal suspension was incorporated into the hydrogel matrix to mimic the optical properties of lymphocytes and monocytes (FIGS. 13A and 13B). The percent composition of the suspension was altered to match the blood cell subpopulations from the blood sample control (Streck) (FIG. 13C).

Figure 13:
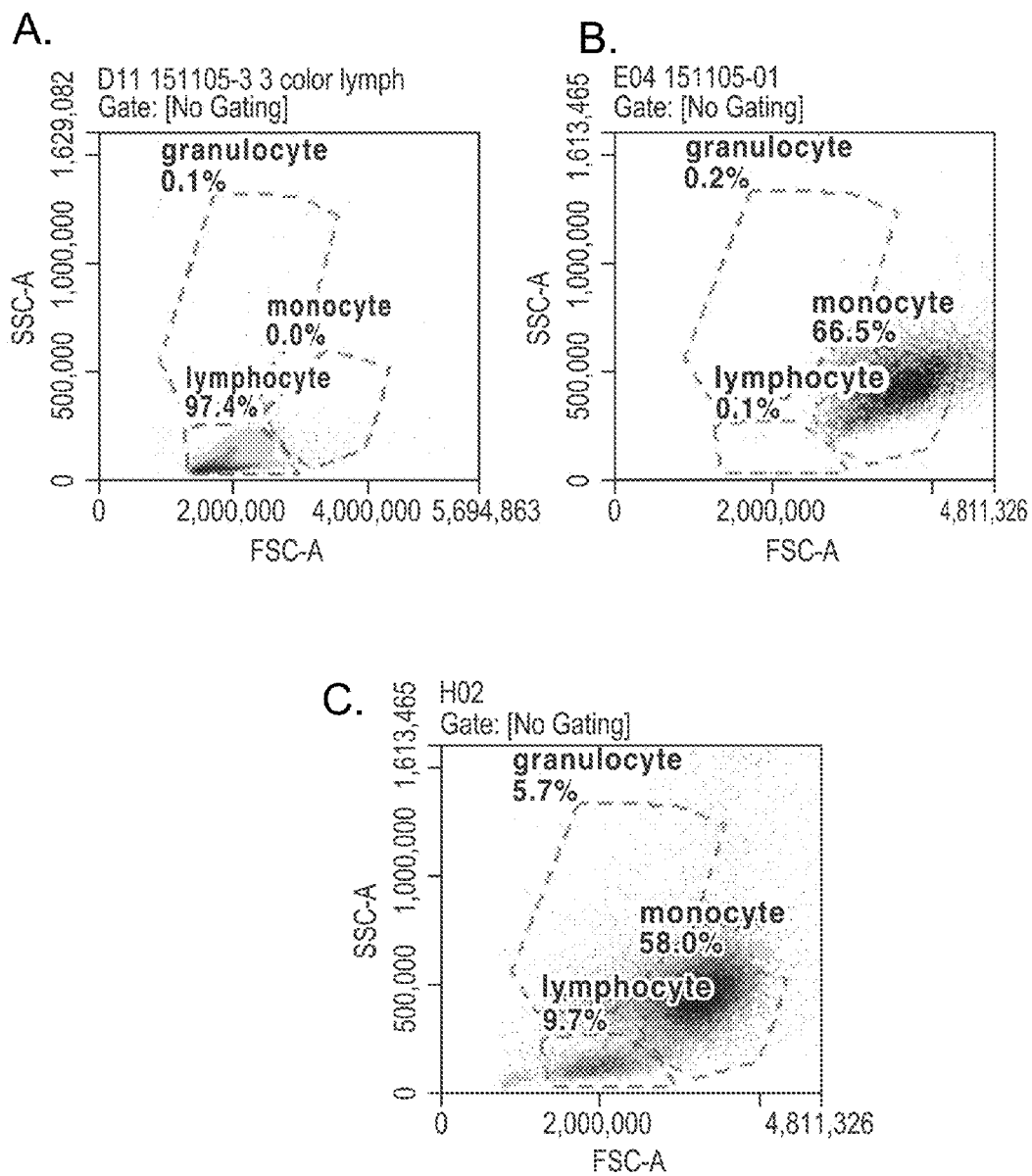
FIG. 13 are scatter plots for various hydrogel particles (A) and (B) and a commercial blood sample (C).

Specifically, the concentration of the acrylamide monomer (0.7-0.8M) of the hydrogel particle was adjusted to increase the forward scatter of the particles to match blood cell subpopulations. The percentage of bisacrylamide cross linker can also be changed to affect forward scatter (1-5%). Silica nanoparticles were used at 5% or 10% in the compositions to adjust side scatter. The results of this experiment are shown in FIG. 13.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method for determining if a sample includes one or more of lymphocytes and monocytes, comprising:
   inserting, into a cytometric device, a plurality of hydrogel particles suspended in an aqueous solution, the plurality of hydrogel particles including: (1) a first portion of hydrogel particles having forward scatter, side scatter, and hydrodynamic properties substantially similar to a lymphocyte, and (2) a second portion of hydrogel particles having forward scatter, side scatter, and hydrodynamic properties substantially similar to a monocyte, wherein each hydrogel particle of the plurality of hydrogel particles comprises a polymerized monomer and has at least one functionalized surface having at least one cell surface marker;
   measuring the forward scatter, side scatter, and hydrodynamic properties of each hydrogel particle of the plurality of hydrogel particles using the cytometric device;
   calibrating the cytometric device based on the measured forward scatter, side scatter, and hydrodynamic properties of the plurality of hydrogel particles;
   adding a sample comprising a plurality of cells to the calibrated cytometric device; and
   measuring the forward scatter, side scatter, and hydrodynamic properties of each cell of the plurality of cells using the calibrated cytometric device to determine if the sample includes one or more of lymphocytes and monocytes.

2. A method for detecting a white blood cell in a sample, comprising:
   inserting, into a cytometric device, a hydrogel particle in aqueous solution, the hydrogel particle having optical-scatter and hydrodynamic properties substantially similar to a white blood cell, the hydrogel particle comprising a polymerized monomer and being functionalized such that it includes at least one cell surface marker;
   measuring the optical-scatter and hydrodynamic properties of the hydrogel particle using the cytometric device to calibrate the cytometric device;
   inserting a sample in the cytometric device, the sample comprising a plurality of cells;
   measuring the optical-scatter and hydrodynamic properties of individual cells of the plurality of cells; and
   determining, based on the measurements of the optical-scatter and hydrodynamic properties, whether a white blood cell or plurality thereof is present in the sample.

3. The method of claim 2, further comprising sorting the white blood cell or plurality of white blood cells to a separate vessel if one or more white blood cells is determined to be present in the sample.

4. The method of claim 2, further comprising: inserting a plurality of hydrogel particles into the cytometric device, wherein each hydrogel particle of the plurality of hydrogel particles has at least one optical-scatter or hydrodynamic property substantially similar to a white blood cell sub-type, wherein the cytometric device is calibrated based on measured optical-scatter and hydrodynamic properties of each hydrogel particle of the plurality of hydrogel particles.

5. The method of claim 4, wherein at least one optical-scatter property is the same for each hydrogel particle of the plurality of hydrogel particles.

6. The method of claim 2, wherein at least one optical-scatter property is side scatter (SSC).

7. The method of claim 2, wherein at least one optical-scatter property is forward scatter (FSC).

8. The method of claim 2, wherein the hydrogel particle has a fluorescence emission substantially similar to a white blood cell, the method further comprising:
   measuring the fluorescence emission of the hydrogel particle using the cytometric device to calibrate the cytometric device; and
   measuring the fluorescence emission of individual cells of the plurality of cells, wherein determining whether a white blood cell or plurality thereof is present in the sample is further based on measured fluorescence emissions.

9. The method of claim 2, wherein at least one optical-scatter property is a ratio of FSC to SSC.

10. The method of claim 2, wherein the polymerized monomer of the hydrogel particle is selected from hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxypoly(ethylene glycol) methacrylate, methacrylic acid, sodium methacrylate, glycerol methacrylate, hydroxypropyl methacrylate, hydroxybutyl methacrylate, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinyl carbazole, 4-vinylpyridine, 2-vinylpyridine, or a combination thereof.

11. The method of claim 2, wherein the polymerized monomer of the hydrogel particle is a biodegradable monomer.

12. The method of claim 11, wherein the biodegradable monomer is a monosaccharide, disaccharide, polysaccharide, peptide, protein, or protein domain.

13. The method of claim 12, wherein the biodegradable monomer is a protein or protein domain comprising at least one non-natural amino acid.

14. The method of claim 11, wherein the biodegradable monomer is a structural polysaccharide.

15. The method of claim 11, wherein the biodegradable monomer is agar, agarose, alginic acid, alguronic acid, alpha glucan, amylopectin, amylose, arabinoxylan, beta-glucan, callose, capsullan, carrageenan polysaccharide, cellodextrin, cellulin, cellulose, chitin, chitosan, chrysolaminarin, curdlan, cyclodextrin, alpha-cyclodextrin, dextrin, dextran, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage gluxan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof.

16. The method of claim 11, wherein the biodegradable monomer is chitosan or hyaluronan.

17. The method of claim 12, wherein the protein is a structural protein, a domain thereof, or a combination thereof.

18. The method of claim 12, wherein the protein is a proteoglycan, a domain thereof, or a combination thereof.

19. The method of claim 12, wherein the protein is an extracellular matrix component.

20. The method of claim 18, wherein the proteoglycan is decorin, biglycan, testican, bikunin, fibromodulin, lumican, a domain thereof, or a combination thereof.

21. The method of claim 19, wherein the protein is elastin or a proteoglycan.

22. The method of claim 19, wherein the protein is collagen.

23. The method of claim 22, wherein the collagen is collagen type I, collagen type II, collagen type III, a domain thereof or a combination thereof.

24. The method of claim 2, wherein the polymerized monomer of the hydrogel particle is bifunctional.

25. The method of claim 2, wherein the at least one cell surface marker is one of the cell surface markers set forth in Table 4, or a combination thereof.

26. A method for calibrating a cytometric device for analysis of white blood cells, comprising:
  inserting, into a cytometric device, a plurality of hydrogel particles suspended in an aqueous solution, each hydrogel particle of the plurality of hydrogel particles having side scatter, forward scatter, and hydrodynamic properties substantially similar to one of a lymphocyte, monocyte, or granulocyte, each hydrogel particle comprising a polymerized monomer and configured with at least one functionalized surface having at least one cell surface marker;
  measuring the side scatter, forward scatter, and hydrodynamic properties of each hydrogel particle of the plurality of hydrogel particles using the cytometric device; and
  calibrating the cytometric device for analysis of white blood cells based on the measured side scatter, forward scatter, and hydrodynamic properties of the plurality of hydrogel particles.

* * * * *